US010159732B2

(12) United States Patent
Manning et al.

(10) Patent No.: US 10,159,732 B2
(45) Date of Patent: *Dec. 25, 2018

(54) STABLE AQUEOUS FORMULATIONS OF ADALIMUMAB

(71) Applicant: Coherus Biosciences, Inc., Redwood City, CA (US)

(72) Inventors: Mark Manning, Johnstown, CO (US); Robert W. Payne, Fort Collins, CO (US)

(73) Assignee: Coherus Biosciences, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/726,165

(22) Filed: Oct. 5, 2017

(65) Prior Publication Data

US 2018/0043018 A1 Feb. 15, 2018

Related U.S. Application Data

(63) Continuation of application No. 15/360,678, filed on Nov. 23, 2016, now Pat. No. 9,861,695, which is a continuation of application No. 14/020,733, filed on Sep. 6, 2013.

(60) Provisional application No. 61/770,421, filed on Feb. 28, 2013, provisional application No. 61/769,581, filed on Feb. 26, 2013, provisional application No. 61/698,138, filed on Sep. 7, 2012.

(51) Int. Cl.
| | |
|---|---|
| *A61K 39/395* | (2006.01) |
| *A61K 47/12* | (2006.01) |
| *A61K 47/18* | (2017.01) |
| *A61K 47/22* | (2006.01) |
| *A61K 47/26* | (2006.01) |
| *C07K 16/24* | (2006.01) |
| *A61K 47/02* | (2006.01) |
| *A61K 47/10* | (2017.01) |
| *A61K 47/14* | (2017.01) |
| *A61K 47/24* | (2006.01) |
| *A61K 9/08* | (2006.01) |
| *A61K 39/00* | (2006.01) |

(52) U.S. Cl.
CPC .......... *A61K 39/39591* (2013.01); *A61K 9/08* (2013.01); *A61K 39/3955* (2013.01); *A61K 39/39533* (2013.01); *A61K 47/02* (2013.01); *A61K 47/10* (2013.01); *A61K 47/12* (2013.01); *A61K 47/14* (2013.01); *A61K 47/18* (2013.01); *A61K 47/183* (2013.01); *A61K 47/22* (2013.01); *A61K 47/24* (2013.01); *A61K 47/26* (2013.01); *C07K 16/241* (2013.01); *A61K 2039/505* (2013.01); *A61K 2039/542* (2013.01); *A61K 2039/545* (2013.01); *C07K 2317/21* (2013.01); *C07K 2317/24* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,597,966 | A | 7/1986 | Zolton et al. |
| 5,104,651 | A | 4/1992 | Boone et al. |
| 5,789,554 | A | 8/1998 | Leung et al. |
| 5,886,154 | A | 3/1999 | Lebing et al. |
| 5,945,098 | A | 8/1999 | Sarno et al. |
| 6,090,382 | A | 7/2000 | Salfeld et al. |
| 6,171,586 | B1 | 1/2001 | Lam et al. |
| 6,171,686 | B1 | 1/2001 | Lam et al. |
| 6,238,664 | B1 | 5/2001 | Hellerbrand et al. |
| 6,252,055 | B1 | 6/2001 | Relton |
| 6,258,562 | B1 | 6/2001 | Saffeld et al. |
| 6,281,336 | B1 | 8/2001 | Laursen et al. |
| 6,696,056 | B1 | 2/2004 | Cheung et al. |
| 7,250,165 | B2 | 7/2007 | Heavner et al. |
| 7,648,702 | B2 | 1/2010 | Gombotz et al. |
| 8,216,583 | B2 | 7/2012 | Krause |
| 8,420,081 | B2 | 4/2013 | Fraunhofer et al. |
| 8,632,778 | B2 | 1/2014 | Kakuta et al. |
| 8,802,100 | B2 | 8/2014 | Krause et al. |
| 8,821,865 | B2 | 9/2014 | Neu et al. |
| 8,883,146 | B2 | 11/2014 | Fraunhofer et al. |
| 8,889,135 | B2 | 11/2014 | Fischkoff et al. |
| 8,916,157 | B2 | 12/2014 | Krause |
| 9,085,619 | B2 | 7/2015 | Fraunhofer |
| 9,114,166 | B2 | 8/2015 | Krause |
| 9,340,611 | B2 | 5/2016 | Manning et al. |
| 9,340,612 | B2 | 5/2016 | Manning et al. |
| 9,346,880 | B2 | 5/2016 | Manning et al. |
| 9,382,317 | B2 | 7/2016 | Manning et al. |
| 9,682,145 | B2 | 6/2017 | Manning et al. |

(Continued)

FOREIGN PATENT DOCUMENTS

| | | |
|---|---|---|
| CN | 102988984 | 5/2015 |
| EP | 1324776 | 9/2009 |

(Continued)

OTHER PUBLICATIONS

Search Report for corresponding PCT application PCT/US13/58618.

(Continued)

*Primary Examiner* — Yunsoo Kim

(74) *Attorney, Agent, or Firm* — Fish & Richardson P.C.

(57) ABSTRACT

The invention provides aqueous pharmaceutical adalimumab compositions suitable for long-term storage of adalimumab, methods of manufacture of these compositions, methods of administration, and kits containing same.

13 Claims, 28 Drawing Sheets

(26 of 28 Drawing Sheet(s) Filed in Color)

(56) References Cited

U.S. PATENT DOCUMENTS

| | | | |
|---|---|---|---|
| 9,707,293 B2 | 7/2017 | Manning et al. |
| 9,724,414 B2 | 8/2017 | Manning et al. |
| 9,724,415 B2 | 8/2017 | Manning et al. |
| 9,731,008 B2 | 8/2017 | Manning et al. |
| 9,731,009 B2 | 8/2017 | Manning et al. |
| 9,737,600 B2 | 8/2017 | Manning et al. |
| 9,757,454 B2 | 9/2017 | Manning et al. |
| 9,770,507 B2 | 9/2017 | Manning et al. |
| 9,782,479 B2 | 10/2017 | Manning et al. |
| 9,782,480 B2 | 10/2017 | Manning et al. |
| 9,789,185 B2 | 10/2017 | Manning et al. |
| 9,808,525 B2 | 11/2017 | Manning et al. |
| 9,861,695 B2 | 1/2018 | Manning et al. |
| 2002/0004478 A1 | 1/2002 | Danko et al. |
| 2003/0138417 A1 | 7/2003 | Kaisheva et al. |
| 2003/0180287 A1 | 9/2003 | Gombotz et al. |
| 2003/0206898 A1 | 11/2003 | Fischkoff et al. |
| 2004/0022792 A1 | 2/2004 | Klinke |
| 2004/0033228 A1 | 2/2004 | Krause et al. |
| 2004/0033535 A1 | 2/2004 | Boyle et al. |
| 2004/0038878 A1 | 2/2004 | Tanikawa et al. |
| 2004/0170623 A1 | 9/2004 | Arvinte et al. |
| 2006/0149042 A1 | 7/2006 | Konstantinov et al. |
| 2006/0165733 A1 | 7/2006 | Betz et al. |
| 2007/0036779 A1 | 2/2007 | Bardat et al. |
| 2007/0184050 A1 | 8/2007 | Ishikawa |
| 2008/0124326 A1 | 5/2008 | Rehder et al. |
| 2008/0311078 A1 | 12/2008 | Gokarn et al. |
| 2009/0291062 A1 | 11/2009 | Fraunhofer |
| 2010/0278822 A1 | 11/2010 | Fraunhofer |
| 2012/0028877 A1 | 2/2012 | Gokam |
| 2013/0195888 A1 | 8/2013 | Wang et al. |
| 2013/0216522 A1 | 8/2013 | Huille et al. |
| 2013/0216525 A1 | 8/2013 | Chen |
| 2013/0243764 A1 | 9/2013 | Ellis et al. |
| 2013/0273066 A1 | 10/2013 | Gokarn et al. |
| 2013/0273067 A1 | 10/2013 | Gokarn et al. |
| 2013/0336968 A1 | 12/2013 | Danek-Bulius et al. |
| 2014/0141007 A1 | 5/2014 | Fraunhofer et al. |
| 2014/0141008 A1 | 5/2014 | Fraunhofer et al. |
| 2014/0186361 A1 | 7/2014 | Manning et al. |
| 2015/0150982 A1 | 6/2015 | Michael et al. |
| 2015/0190513 A1 | 7/2015 | Manning et al. |
| 2015/0191538 A1 | 7/2015 | Manning et al. |
| 2016/0031982 A1 | 2/2016 | Manning et al. |
| 2016/0039926 A1 | 2/2016 | Manning et al. |
| 2016/0256545 A1 | 9/2016 | Manning et al. |
| 2016/0256547 A1 | 9/2016 | Manning et al. |
| 2016/0263226 A1 | 9/2016 | Manning et al. |
| 2016/0303233 A1 | 10/2016 | Manning et al. |
| 2016/0303234 A1 | 10/2016 | Manning et al. |
| 2016/0304599 A1 | 10/2016 | Manning et al. |
| 2016/0304600 A1 | 10/2016 | Manning et al. |
| 2016/0304601 A1 | 10/2016 | Manning et al. |
| 2016/0319011 A1 | 11/2016 | Gokarn et al. |
| 2016/0339102 A1 | 11/2016 | Gokarn et al. |
| 2016/0362484 A1 | 12/2016 | Gokarn et al. |
| 2016/0362486 A1 | 12/2016 | Gokarn et al. |
| 2017/0143828 A1 | 5/2017 | Fraunhofer et al. |
| 2017/0312361 A1 | 11/2017 | Manning et al. |
| 2018/0021433 A1 | 1/2018 | Manning et al. |
| 2018/0028653 A1 | 2/2018 | Manning et al. |
| 2018/0028654 A1 | 2/2018 | Manning et al. |
| 2018/0028655 A1 | 2/2018 | Manning et al. |
| 2018/0028656 A1 | 2/2018 | Manning et al. |
| 2018/0028657 A1 | 2/2018 | Manning et al. |
| 2018/0043019 A1 | 2/2018 | Manning et al. |
| 2018/0055929 A1 | 3/2018 | Manning et al. |
| 2018/0055930 A1 | 3/2018 | Manning et al. |
| 2018/0140701 A1 | 5/2018 | Manning et al. |

FOREIGN PATENT DOCUMENTS

| | | |
|---|---|---|
| EP | 1528933 | 5/2012 |
| JP | 2001-503781 | 3/2001 |
| JP | 2010-523493 | 7/2010 |
| JP | 2011-509972 | 3/2011 |
| JP | 2011-518110 | 6/2011 |
| WO | WO 1997/029131 | 8/1997 |
| WO | WO 1997/45140 | 12/1997 |
| WO | WO 1998/004281 | 2/1998 |
| WO | WO 1998/056418 | 12/1998 |
| WO | WO 1999/037329 | 7/1999 |
| WO | WO 2000/56772 | 9/2000 |
| WO | WO 2000/067789 | 11/2000 |
| WO | WO 2002/013860 | 2/2002 |
| WO | WO 2002/100330 | 12/2002 |
| WO | WO 2004/091656 | 10/2004 |
| WO | WO 2006/022599 | 3/2006 |
| WO | 2006/138181 A2 | 12/2006 |
| WO | 2007/092772 A2 | 8/2007 |
| WO | 2009/015345 A1 | 1/2009 |
| WO | WO 2009/073569 | 6/2009 |
| WO | WO 2009/073805 | 6/2009 |
| WO | WO 2009/084659 | 7/2009 |
| WO | 2010/062896 A1 | 6/2010 |
| WO | WO 2010/066634 | 6/2010 |
| WO | 2010/129469 A1 | 11/2010 |
| WO | 2011/061712 A1 | 5/2011 |
| WO | WO 2011/080209 | 7/2011 |
| WO | 2011/141926 A2 | 11/2011 |
| WO | WO 2012/037534 | 3/2012 |
| WO | 2012/065072 A2 | 5/2012 |
| WO | 2012/143418 A1 | 10/2012 |
| WO | 2012/165917 A1 | 12/2012 |
| WO | 2013/006454 A1 | 1/2013 |
| WO | WO 2013/011076 | 1/2013 |
| WO | 2013/063510 A1 | 5/2013 |
| WO | 2013/096835 A1 | 6/2013 |
| WO | 2013/164837 A1 | 11/2013 |
| WO | 2013/186230 A1 | 12/2013 |
| WO | 214/039903 A2 | 3/2014 |
| WO | 2014/099636 A1 | 6/2014 |
| WO | WO 2014/130064 | 8/2014 |

OTHER PUBLICATIONS

"Development Pharmaceutics for Biotechnological and Biological Products (Annex to Note for Guidance on Development Pharmaceutics)," by Committee for Proprietary Medicinal Products, The European Agency for the Evaluation of Medicinal Products (Oct. 21, 1999).

Nozaki & Tanford, "Examination of Titration Behavior," Methods Enzymol., 11: 715-734 (1967).

"Note for Guidance on Development Pharmaceutics," by the Committee for Proprietary Medicinal Products (CPMP), The European Agency for the Evaluation of Medicinal Products (Jan. 28, 1998).

Akers et al., "Formulation Development of Protein Dosage Forms," Ch. 2 in Development and Manufacture of Protein Pharmaceuticals, Kluwer Academic/Plenum Publishers: New York, 47-127 (Nail et al., eds., 2002).

Avastin® Label (Feb. 2004).

Butler & Hamilton, "Quantitation of Specific Antibodies: Methods of Express, Standards, Solid-Phase Considerations, and Specific Applications," Ch. 9 in Immunochemistry of Solid-Phase Immunoassay, CRC Press (John E. Butler ed. 1991).

Christensen, "Proteins as buffers," Annals of the New York Academy of Sciences, 133:34-40 (Apr. 1966).

Cleland & Langer, "Formulation and Delivery of Proteins and Peptides: Design and Development Strategies," Ch. 1 in Formulation and Delivery of Proteins and Peptides, ACS Symposium Series 567, 1-19 (1994).

Dean, "Lange's Handbook of Chemistry," McGraw-Hill, p. 8.49, 8.65 (9th ed. 1999).

Enbrel® Label (Nov. 1998).

Enbrel® Label (Sep. 2002).

Flebogamma® Label (Jan. 2004).

Fransson & Espander-Jansson, "Local Tolerance of Subcutaneous Injections," J. Pharm. Pharmacol., 48:1012-1015 (1996).

(56) References Cited

OTHER PUBLICATIONS

Frenken et al., "Identification of the Component Part in an Epoetin Alfa Preparation that Causes Pain after Subcutaneous Injection," American J. of Kidney Diseases, 22(4): 553-556 (1993).
Gamimune® Label (Oct. 2005).
Gammagard Liquid Label (Apr. 2005).
Gamunex® Label (Nov. 2005).
Hanauer, Gastroenterology, vol. 130 p. 323-333 (Feb. 2006).
Gokarn et al., "Excipients for Protein Drugs," Ch. 17 in Excipient Development for Pharmaceutical, Biotechnology, and Drug Delivery Systems (Ashok Katdare & Mahesh V. Chaubal eds., 2006).
Handbook of Pharmaceutical Excipients, Pharmaceutical Press (Raymond C. Rowe, Paul J. Sheskey, & Siân C. Owen eds., 5th ed. 2006).
Humira® Label (Feb. 2007).
Humira® Label (Feb. 2008).
Humira® Label (Jan. 2003).
Humira® Label (Jan 2008).
Humira® Label (Nov. 2006).
Humira® Label (Oct. 2005).
Humira® Label (Oct. 2016).
Jefferis et al., "Recognition Sites on Human IgG for Fcγ Receptors: The Role of Glycosylation," Immunology Letters, 44: 111-117 (1995).
Larsen et al., "Pain Perception after Subcutaneous Injections of Media Containing Different Buffers," Basic & Clinical Pharmacology & Toxicology, 98:218-221 (2006).
Octagam ® Label (Mar. 2004).
Olthuis et al., "Characterization of Proteins by Means of their Buffer Capacity, Measured with an ISFET-based Coulometric Sensor—Actuator System," Biosensors & Bioelectronics, 9:743-751 (1994).
Parslow, "Immunoglobulins & Immunoglobulin Genes," Ch. 7 in Medical Immunology, Appleton & Lange (Daniel P. Stites, Abba I. Terr, & Tristram G. Parslow eds., 9th ed. 1997).
Kempeni, Preliminary results of early clinical trials with the fully human anti-TNFa monoclonal antibody D2E7, Ann Rheum Dis, 58: (Suppl I), 170-172 (1999).
Remicade® Label (Aug. 1998).
Stoner et al., "Protein—Solute Interactions Affect the Outcome of Ultrafiltration/Diafiltration Operations," J. Pharm. Sci., 93:2332-2342 (2004).
Synagis® Label (Jul. 2004).
Tysabri® Label (Nov. 2004).
Van Slyke, "On the Measurement of Buffer Values and on the Relationship of Buffer Value to the Dissociation Constant of the Buffer and the Concentration and Reaction of the Buffer Solution," J. Biol. Chem., 52:525-570 (1922).
Vectibix® Label (Sep. 2006).
Vivaglobin® Label (Jan. 2006).
AbbVie Filing in Support of Opposition Against EP 1324776 B1, Filed Jun. 16, 2010.
Arakawa et al., Protection of Bovine Serum Albumin from Aggregation by Tween 80, J. Pharm. Sci 89(5), 646-651 (May 2000).
Aulton, ed., Pharmaceutics, The Science of Dosage Form Design, 2nd ed., Churchill Livingstone: New York, 317-318, 544-553 (2002).
Bam et al., Tween Protects Recombinant Human Growth Hormone against Agitation-Induced Damage via Hydrophobic Interactions, J. Pharm. Sci., 87(12), 1554-1559 (Dec. 1998).
Barrea et al., Effects of treatment with a fully human anti-tumour necrosis factor a monoclonal antibody on the local and systemic homeostasis of interleukin 1 and TNFa in patients with rheumatoid arthritis, Ann. Rheum. Dis., 60, 660-669 (2001).
Bischoff et al., Deamidation of Asparagine and Glutamine Residues in Proteins and Peptides: Structural Determinants and Analytical Methodology, J. of Chromatography B, 662, 261-278 (1994).
Capasso et al., Effect of the Three-Dimensional Structure on the Deamidation Reaction of Ribonuclease A, J. Peptide Res., 54,377-382 (1999).
Capasso et al., First Evidence of Spontaneous Deamidation of Glutamine Residue via Cyclic Imide to α- and γ-Glutamic Residue under Physiological Conditions, J. Chem. Soc. Chem. Commun., pp. 1667-1668 (1991).
Carpenter and Manning, eds., Rational Design of Stable Protein Formulations. Theory and Practice, Pharmaceutical Biotechnology, vol. 13, Kluwer Academic/Plenum Publishers: New York (2002).
Cleland et al., The Development of Stable protein Formulations: A Close Look at Protein Aggregation, Deamidation, and Oxidation, Critical Reviews in Therapeutic Drug Carrier Systems, 10(4), 307-377 (1993).
Frokjaer et al., eds., Pharmaceutical Formulation development of Peptides and Proteins, Taylor & Francis: London (2000).
Gatlin et al., Formulation and Administration Techniques to Minimize Injection Pain and Tissue Damage Associated with Parenteral Products, Injectable Drug Development Techniques to Reduce Pain and Irritation, pp. 401-425 (1999).
Gennaro, ed., Remington: The Science and Practice of Pharmacy, 20th ed., Solutes, 785-786 (2000).
Goolcharran et al., The Effects of a Histidine Residue on the C-Terminal Side of an Asparaginyl Residue on the Rate of Deamidation Using Model Pentapeptides, J. of Pharmaceutical Sciences, vol. 89, Issue 6, 818-825 (2000).
Jorgensen et al., Pain Assessment of Subcutaneous Injections, Ann. Pharma., 30(7/8), 729-732 (Jul./Aug. 1996).
Krishnamurthy et al., The Stability Factor: Importance in Formulation Development, Curr. Pharm. Biotech, 3, 361-371 (2002).
Levine et al., The Use of Surface Tension Measurements in the Design of Antibody-Based Product Formulations, J. Parenteral Sci. & Tech., 45(3), 160-165 (May/Jun. 1991).
Lorenz, Technology evaluation: Adalimumab, Abbott Laboratories, Current Opinion in Molecular Therapeutics, 4(2), 185-190 (2002).
Manning et al., Stability of Protein Pharmaceuticals, Pharm Res., 6(11), 903-918 (1989).
Nabuchi et al., The Stability and Degradation Pathway of Recombinant Human Parathyroid Hormone: Deamidation of Asparaginyl Residue and Peptide Bond Cleavage at Aspartyl and Asparaginyl Residues, Pharmaceutical Research, vol. 14 Issue 12, 1685-1690 (1997).
Nema et al., Excipients and Their Use in Injectable Products, FDA J. Pharm. Sci. & Tech, 51(4), 166-171 (Jul./Aug. 1997).
Paborji et al., Chemical and Physical Stability of Chimeric L6, a Mouse-Human Monoclonal Antibody, Pharmaceutical Research, vol. 11, Issue 5, 764-771 (1994).
Patel et al., Chemical Pathways of Peptide Degradation. II. Kinetics of Deamidation of an Asparaginyl Residue in a Model Hexapeptide, Pharmaceutical Research, vol. 7, Issue 7, 703-711 (1990).
Santora et al, Characterization of Recombinant human Monoclonal Tissue Necrosis Factor-a Antibody Using Cation-Exchange HPLC and Capillary Isoelectric Focusing, Analytic Biochem, 275, 98-108 (1999).
Schein, Solubility as a Function of Protein Structure and Solvent Components, BioTechnology 8, 308-317 (Apr. 1990).
Scotchler et al., Deamidation of Glutaminyl Residues: Dependence on pH, Temperature, and Ionic Strength, Analytical Biochemistry, 59, 319-322 (1974).
Sorbera et al., Adalimumab, Drugs Fut, 26(7), 639-646 (Jul. 2001).
United States Pharmacopeia and National Formulary (USP 24-NF 19). vol. 2. Rockville, MD: United States Pharmacopeia Convention; 1999: 1971-1977, 2011-2021, 2404-2406.
Wang, Instability, stabilization, and formulation of liquid protein pharmaceuticals, Int. J. Pharma., 185, 129-188 (1999).
Wright et al., Nonenzymatic Deamidation of Asparaginyl and Glutaminyl Residues in Protein, Critical Reviews in Biochemistry and Molecular Biology, 26:1, 1-52 (1991).
Ann L. Daugherty, et al., Formulation and Delivery Issues for Monoclonal Antibody Therapeutics, Adv. Drug Deliv. Rev. 58:686 (2006).
Branden A. Salinas, et al., Understanding and Modulating Opalescence and Viscosity in a Monoclonal Antibody Formulation, 99 J. Pharm. Sci. 82 (2010).
Christine C. Lee, et al., Toward aggregation-resistant antibodies by design, 31 Trends in Biotech. 612 (2013).

(56) References Cited

OTHER PUBLICATIONS

Douglas D. Banks, et al., Native-State Solubility and Transfer Free Energy as Predictive Tools for Selecting Excipients to Include in Protein Formulation Development Studies, 101 J. Pharm. Sci. 2720 (2012).
Edward C. Keystone, et al., Golitnumab, a Human Antibody to Tumor Necrosis Factor-α Given by Monthly Subcutaneous Injections, in Active Rheumatoid Arthritis Despite Methotrexate: The Go-Forward Study, 68 Ann. Rheum. Dis. 789 (2009).
Emily Ha, et al., Peroxide Formation in Polysorbate 80 and Protein Stability, 91 J. Pharm. Sci. 2252 (2002).
Eva Y. Chi, et al., Physical Stability of Proteins in Aqueous Solution: Mechanism and Driving Forces in Nonnative Protein Aggregation, 20 Pharm. Res. 1325 (2003).
Jenny M. Phillips, Manufacture and Quality Control of CAMPATH-1 Antibodies for Clinical Trials, 3 Cytotherapy 233 (2001).
John F. Carpenter, et al., Chapter 7: Freezing- and Drying-Induced Perturbations of Protein Structure and Mechanisms of Protein Protection by Stabilizing Additives, in Freeze-Drying/Lyophilization of Pharmaceutical and Biological Products 167 (2d ed. 2004).
John F. Carpenter, et at., Inhibition of Stress-Induced Aggregation of Protein Therapeutics, 309 Methods in Enzymology 236 (1999).
John F. Carpenter, et al., Rational Design of Stable Lyophilized Protein Formulations: Some Practical Advice, Pharm. Res., 14(8):969 (1997).
Jose Baselga, et al., Phase II Study of Weekly Intravenous Recombinant Humanized Anti-p185HER2 Monoclonal Antibody in Patients with HER2/neu-overexpressing Metastatic Breast Cancer, 14 J. Clin. Oncol. 738 (1996).
Joseph M. Perehiacca et al., Engineering Aggregation-resistant Antibodies, 3 Annu. Rev. Chem. Biomol. Eng. 263 (2012).
Larry R. Helms, et al., Destabilizing Loop Swaps in the CDRs of an Immunoglobulin VL Domain, 4 Protein Sci. 2073 (1995).
Lene Jørgensen, et al., Recent Trends in Stabilising Peptides and Proteins in Pharmaceutical Formulation—Considerations in the Choice of Excipients, 6 Expert Opin. Drug Deliv. 1219 (2009).
Marco van de Weert & Theodore W. Randolph, Chapter 6: Physical Instability of Peptides and Proteins, in Pharmaceutical Formulation Development of Peptides and Proteins 107 (2012).
Masako Ohnishi & Hiromichi Sagitani, The Effect of Nonionic Surfactant Structure on Hemolysis, 70 J. Am. Oil Chemists' Soc'Y 679 (1993).
Michael J. Treuheit, et al., Inverse Relationship of Protein Concentration and Aggregation, 19 Pharm. Res. 511 (2002).
Robert G. Hamilton, The Human IGG Subclasses (2001).
Robert Ritzel, et al., Pharmacokinetic, Insulinotropic, and Glucagonostatic Properties of GLP-I [7-36 amide] after Subcutaneous Injection in Healthy Volunteers. Dose-response-relationships, 38 Diabetologia 720 (1995).
Sampathkumar Krishnan, et al., Chapter 16: Development of Formulations for Therapeutic Monoclonal Antibodies and Fc Fusion Proteins, in Formulation and Process Development Strategies for Manufacturing Biopharmaceuticals 383 (2010).
Stefan Ewert, et al., Biophysical Properties of Human Antibody Variable Domains, 325 J. Mol. Biol. 531 (2003).
Theodore W. Randolph & John F. Carpenter, Engineering Challenges of Protein Formulations, 53 Am. Inst. Chem. Eng. J. 1902 (2007).
Tim J. Kamerzell, et al., Increasing IgG Concentration Modulates the Conformational Heterogeneity and Bonding Network that Influence Solution Properties, 113 J. Phys. Chem. B 6109 (2009).
Enbrel® Summary Basis of Approval (1998).
Gloff et al., "Pharmacokinetics & Protein Therapeutics," Advanced Drug Delivery Reviews, 4 (1990) 359-386.
Golimumab/Simponi® label (Revised Dec. 2011).
Guidance for Industry, Clinical Development Programs for Drugs, Devices and Biological Products for the Treatment of Rheumatoid Arthritis (1999).
Infliximab/Remicade® label (Nov. 1999).
Remicade® Summary Basis of Approval (1999).
Van Gestel et al., "Development and Validation of the European League Against Rheumatism Response Criteria for Rheumatoid Arthritis," Arthritis & Rheumatism, vol. 39, No. 1, Jan. 1996, pp. 34-40.
Wang et al. "Antibody structure, instability, and formulation" Minirevew, accepted Jun. 4, 2006.
U.S. Appl. No. 60/690,582, filed Jun. 14, 2005.
Australian Examination Report No. 1 in Australian Appln. No. 2013312300, dated Jul. 28, 2017, 4 pages.
Carpenter et al., "Overlooking Subvisible Particles in Therapeutic Protein Products: Gaps That May Compromise Product Quality," J. Pharm Sci, Apr. 2009, 98(4): 1201-1205.
Chinese Office Action in Chinese Appln. No. 20130058126.8, dated Nov. 16, 2015, 14 pages. (with machine translation).
Eurasian Office Action in Eurasion Appln. No. 201590518, dated Mar. 10, 2016, 5 pages.
European Search Report (extended) in European Appln. No. 13835291, dated Mar. 15, 2016, 6 pages.
Gilbert and Cothran, "SC versus IV delivery: Reducing costs while increasing patient satisfaction," Hemotology & Oncology News & Issues, Dec. 2005, 25-29.
Hawe et al., "Taylor Dispersion Analysis Compared to Dynamic Light Scattering for the Size Analysis of Therapeutic Peptides and Proteins and Their Aggregates," Pharm Res, May 2011, 28: 2302-2310.
Humira, product information sheet, p. 1-16, 2002, Abbott Lab.
International Preliminary Report on Patentability in International Appln. No. PCT/US2013/58618, dated Mar. 10, 2015, 10 pages.
Israel Office Action in Israeli Appln. No. 2336545, dated Jan. 21, 2018, 5 pages. (w/ English Translation).
Japanese Office Action in Japanese Appln. No. 2015-531261, dated Apr. 25, 2018, 6 pages (with machine translation).
Japanese Office Action in Japanese Appln. No. 2015-531261, dated Jun. 21, 2017, 15 pages (with machine translation).
Kavanaugh et al., "Treatment with Adalimumab (D2E7) does not Affect Normal Immune Responsiveness," Arthritis & Rheumatism, Sep. 2002, 46(9): S132.
Kaymakcalan et al., "Development of a Fully Human Anti-TNF Monoclonal Antibody," J Interferon & Cytokine Research, Abstact 6.16, May 1998, 18(5): A-125.
Keystone et al, "Adalmumab (D2E7), A Fully Human Anti-TNF-α Monoclonal Antibody, Inhibits the Progression of Structural Joint Damage in Patients with Active RA Despite Doncomitant Methotrexate Therapy," Arthritis & Rheumatism, Sep. 2002, 46(9): S205.
Maggio, "Use of excipients to control aggregation in peptide and protein formulations," J Excipients and Food Chem, Aug. 2010, 1(2): 40-49.
Singh and Singh, "Effect of Polyols on the Conformational Stability and Biological Activity of a Model Protein Lysozyme," AAPS PharmSciTech, Article 42, Jul. 2003, 4(3): 9 pages.
Taiwanese Office Action in Taiwanese Appln. No. 102132360, dated Oct. 25, 2017, 8 pages (with English translation).
Warne, "Development of high concentration protein biopharmaceuticals: The use of platform approaches in formulation development," European J Pharmaceutics and Biopharmaceutics, Mar. 2011 78(2): 208-212.
U.S. Appl. No. 14/020,733.
U.S. Appl. No. 15/653,228.
U.S. Appl. No. 15/677,857.
U.S. Appl. No. 15/726,195.
U.S. Appl. No. 15/726,215.
U.S. Appl. No. 15/729,243.
U.S. Appl. No. 15/729,295.
U.S. Appl. No. 15/730,399.
U.S. Appl. No. 15/730,425.
U.S. Appl. No. 15/730,445.
U.S. Appl. No. 15/799,851.
U.S. Appl. No. 15/866,154.
U.S. Appl. No. 16/023,046, filed Jun. 29, 2018, Fraunhofer et al.
U.S. Appl. No. 16/023,152, filed Jun. 29, 2018, Fraunhofer et al.
U.S. Appl. No. 16/023,161, filed Jun. 29, 2018, Fraunhofer et al.
U.S. Appl. No. 16/023,205, filed Jun. 29, 2018, Fraunhofer et al.

(56) References Cited

OTHER PUBLICATIONS

U.S. Appl. No. 61/004,992, filed Nov. 30, 2007, Fraunhofer et al.

Alon et al., "Lidocaine for the Alleviation of Pain Associated with Subcutaneous Erythropoietin Injection," Journal of the American Soc. of Nephrology, vol. 5, No. 4, 1161-1162, 1994.

"Annex A Humira Story", AbbVie Biotechnology Limited, submitted to European Patent Office by owner of EP1406656B on Dec. 22, 2014.

Atgam® Label (Nov. 2005).

Bahrenburg et al., "Buffer-free therapeutic antibody preparations provided a viable alternative to conventionally buffered solutions: From protein buffer capacity prediction to bioprocess applications," Bio. J. 10:610-622, 2015.

Karow et al., "Buffer capacity of biologics-from buffer salts to buffering by antibodies," Biotechnol. Prog., vol. 29, No. 2, 480-492, 2013.

Brazeau et al., "Current perspectives on pain upon injection of drugs," Journal of Pharm. Sci., vol. 87, No. 6, 667-677, 1998.

Campath (Alemtuzumab), Genzyme Corporation, 2006.

Gokarn et al., "Self-buffering antibody formulations," J. of Pharm. Sci., vol. 97, No. 8, 3051-3066, 2008.

Granolleras et al., "Experience of pain after subcutaneous administration of different preparations of recombinant human erythropoietin: a randomized, double-blind crossover study," Clin. Nephrol., vol. 36, No. 6, 294-298, 1991.

Harris et al., "Commerical Manufacturing Scale Formulation and Analytical Characterization of Therapeutic Recombinant Antibodies," Drug Development Research 61:137-154, 2004.

Humira® Label (Sep. 2007).

Humira.com [online], "Injection Assistance," Humira®, Mar. 2005, [retrieved on Jan. 12, 2017], Retrieved from the Internet URL: http://web.archive.org/web/20050317083331/http://www.humira.com/hu/hustore/cgibin/ProdSubEV_Cat_205043_SubCat_210170_NavRoot_205042_NavID_301.htm, 2 pages.

McCue et al., "Three Generations of Immunoglobulin G Preparations for Clinical Use," Reviews of Infectious Diseases, vol. 8, Suppl. 4, s374-s381, 1986.

Napke et al., "Excipients and additives: hidden hazards in drug products and in product substitution," Can. Med. Assoc. J., vol. 131, 1449-1452, 1984.

Nash et al., "Randomized Crossover Comparison of Injection Site Pain with 40 mg/0.4 or 0.8 mL Formulations of Adalimumab in Patients with Rheumatoid Arthritis," Rheu. Ther. 3:257-270, 2016.

Octagam® Label (Mar. 2007).

Privigen® Label (Jul. 2007).

Tindall et al., "Mobile Phase Buffers, Part II," LC, GC Europe, 2-4, 2003.

Veys et al., "Pain at the injection site of subcutaneously administered erythropoietin: phosphate-buffered epoetin alpha compared to cirate-buffered epoetin alpha and epoetin beta," Clin. Nephrol., vol. 49, No. 1, 41-44, 1998.

Effect of citrate and phosphate

Effect of NaCl and polysorbate 80 (PS 80)

Effect of citrate and phosphate

Effect of Arg and Gly

Effect of PS 80 and mannitol

Effect of EDTA and NaCl

Effect of Arg and Gly

Effect of PS 80 and NaCl

STABLE AQUEOUS FORMULATIONS OF ADALIMUMAB

FIELD OF THE INVENTION

The present invention relates to aqueous pharmaceutical compositions suitable for long-term storage of adalimumab (including antibody proteins considered or intended as "biosimilar" or "bio-better" variants of commercially available adalimumab), methods of manufacture of the compositions, methods of their administration, and kits containing the same.

BACKGROUND OF THE INVENTION

Tumor necrosis factor alpha (TNFα) is a naturally occurring mammalian cytokine produced by various cell types, including monocytes and macrophages in response to endotoxin or other stimuli. TNFα is a major mediator of inflammatory, immunological, and pathophysiological reactions (Grell, M., et al. (1995) Cell, 83: 793-802).

Soluble TNFα is formed by the cleavage of a precursor transmembrane protein (Kriegler, et al. (1988) Cell 53: 45-53), and the secreted 17 kDa polypeptides assemble to soluble homotrimer complexes (Smith, et al. (1987), J. Biol. Chem. 262: 6951-6954; for reviews of TNF, see Butler, et al. (1986), Nature 320:584; Old (1986), Science 230: 630). These complexes then bind to receptors found on a variety of cells. Binding produces an array of pro-inflammatory effects, including (i) release of other pro-inflammatory cytokines such as interleukin (IL)-6, IL-8, and IL-1, (ii) release of matrix metalloproteinases and (iii) up-regulation of the expression of endothelial adhesion molecules, further amplifying the inflammatory and immune cascade by attracting leukocytes into extravascular tissues.

There are many disorders associated with elevated levels of TNFα. For example, TNFα has been shown to be up-regulated in a number of human diseases, including chronic diseases such as rheumatoid arthritis (RA), inflammatory bowel disorders, including Crohn's disease and ulcerative colitis, sepsis, congestive heart failure, asthma bronchiale and multiple sclerosis. TNFα is also referred to as a pro-inflammatory cytokine.

Physiologically, TNFα is also associated with protection from particular infections (Cerami. et al. (1988), Immunol. Today 9:28). TNFα is released by macrophages that have been activated by lipopolysaccharides of Gram-negative bacteria. As such, TNFα appears to be an endogenous mediator of central importance involved in the development and pathogenesis of endotoxic shock associated with bacterial sepsis.

Adalimumab (Humira®, AbbVie, Inc.) is a recombinant human IgG1 monoclonal antibody specific for human TNF. This antibody is also known as D2E7. Adalimumab consists of 1330 amino acids and has a molecular weight of approximately 148 kilodaltons. Adalimumab has been described and claimed in U.S. Pat. No. 6,090,382, the disclosure of which is hereby incorporated by reference in its entirety. Adalimumab is usually produced by recombinant DNA technology in a mammalian cell expression system, such as, for example, Chinese Hamster Ovary cells. Adalimumab binds specifically to TNFα and neutralizes the biological function of TNF by blocking its interaction with the p55 and p75 cell surface TNF receptors.

Various formulations of adalimumab are known in the art. See, for example, U.S. Pat. Nos. 8,216,583 and 8,420,081.

There is still need for stable liquid formulations of adalimumab that allow its long term storage without substantial loss in efficacy.

SUMMARY OF THE INVENTION

The invention provides stable aqueous formulations comprising adalimumab that allow its long term storage.

In a first embodiment, the invention provides a stable aqueous pharmaceutical composition comprising adalimumab; a stabilizer comprising at least one member selected from the group consisting of a polyol and a surfactant; and a buffer selected from the group consisting of citrate, phosphate, succinate, histidine, tartrate and maleate, wherein said composition has a pH of about 4 to about 8 and preferably about 5 to about 6, and wherein said buffer does not comprise a combination of citrate and phosphate, and preferably does not comprise any citrate buffer. In this embodiment, the stabilizer preferably comprises both polyol and surfactant.

In a second embodiment, utilizing a single buffer system, the invention provides a stable aqueous pharmaceutical composition comprising adalimumab, a polyol, a surfactant, and a buffer system comprising a single buffering agent, said single buffering agent being selected from citrate, phosphate, succinate, histidine, tartrate or maleate, but not including combinations of the foregoing; wherein the formulation has a pH of about 4 to 8, and preferably about 5 to about 6. Histidine and succinate are particularly preferred for use as single buffering agents. As used herein the term buffer, buffer system, or buffering agent, and like terminology, is intended to denoted buffer components that introduce buffer capacity in the formulation in addition to any buffering capacity offered by the protein itself, hence the term "buffer", etc, is not intended to include the protein itself as a self buffering entity.

In a third embodiment, the invention provides a stable aqueous pharmaceutical composition comprising adalimumab, a stabilizer comprising at least one member selected from a polyol and a surfactant, wherein said composition has a pH of about 4 to about 8, and preferably about 5 to about 6, and wherein said composition is substantially free of a buffer.

In a fourth embodiment, the invention provides a stable aqueous pharmaceutical composition comprising adalimumab, a polyol, and a buffer selected from the group consisting of citrate, phosphate, succinate, histidine, tartrate and maleate, wherein said composition has a pH of about 4 to about 8 and preferably about 5 to about 6, and wherein said composition is free or substantially free of a surfactant. Preferably, the composition (i) does not contain the buffer combination of citrate and phosphate; and (ii) the buffer is at least one member selected from the group consisting of histidine and succinate; and (iii) the polyol is selected from the group consisting of mannitol, sorbitol and trehalose.

In a fifth embodiment, the invention provides a stable aqueous pharmaceutical composition comprising adalimumab, a surfactant, and a buffer selected from the group consisting of citrate, phosphate, succinate, histidine, tartrate and maleate, wherein said composition has a pH of about 4 to 8 and preferably about 5 to about 6, and wherein said composition is substantially free of polyol. Preferably, the composition (i) does not contain the buffer combination of citrate and phosphate; and (ii) the buffer is at least one member selected from the group consisting of histidine and succinate, including combinations thereof.

In each of the five embodiments discussed above, the composition may optionally further comprise a stabilizer selected from the group consisting of an amino acid, a salt, ethylenediaminetetraacetic acid (EDTA) and a metal ion. The amino acid stabilizer may be selected from the group consisting of glycine, alanine, glutamate, arginine and methionine. The salt stabilizer may be selected from the group consisting of sodium chloride and sodium sulfate. The metal ion stabilizer may be selected from the group consisting of zinc, magnesium and calcium. Preferably, adalimumab formulations containing the stabilizers mentioned above also do not contain buffer systems in which phosphate buffer and citrate buffer are present in combination, and, most preferably contains buffer systems free or substantially free of citrate buffer. In particularly preferred embodiments, (i) the optional additional stabilizer present in this embodiment is not sodium chloride, or comprises sodium chloride present in amounts not to exceed about 100 mM, and comprises at least one of arginine and glycine, including combinations of the two amino acids; (ii) the buffer, when present, contains no citrate, or at least no citrate and phosphate combination, but is instead at least one of histidine and succinate, including combinations thereof; and (iii) the stabilizer when it includes a polyol is preferably mannitol in amounts exceeding about 150 mM.

In further embodiments the invention is directed to an aqueous, buffered pharmaceutical composition comprising adalimumab and a buffer, wherein (i) the composition is free or substantially free of a buffer combination that comprises both a citrate buffer and a phosphate buffer; and (ii) the composition exhibits long term stability.

Another embodiment of the invention concerns an aqueous, buffered pharmaceutical composition exhibiting long term stability, said composition comprising: (i) adalimumab; (ii) a buffer selected from the group consisting of histidine buffer, succinate buffer, and combinations thereof; (iii) a polysorbate or poloxamer surfactant, or combinations thereof; and (iv) one or both of the following: (a) a stabilizer selected from the group consisting of glycine, alanine, glutamate, arginine, methionine, EDTA, sodium chloride, sodium sulfate, metal ions, and combinations thereof; and (b) a polyol selected from sorbitol, mannitol, and trehalose, or combinations thereof. Optionally, the formulation may also include a sugar, such as sucrose.

In a further embodiment the invention is an aqueous, buffered pharmaceutical composition comprising adalimumab and a buffer, wherein (i) the composition is free or substantially free of a polyol; and (ii) the composition exhibits long term stability.

In still a further embodiment the invention is directed to an aqueous, buffered pharmaceutical composition comprising adalimumab and a buffer, wherein (i) the composition is free or substantially free of surfactant; and (ii) the composition exhibits long term stability.

Another embodiment of the inventions concerns an aqueous pharmaceutical composition comprising adalimumab wherein: (i) the composition is free or substantially free of buffer; and (ii) the composition exhibits long term stability.

In another embodiment, the adalimumab formulation of the present invention comprises, consists of, or consists essentially of, adalimumab, histidine buffer as the sole buffer in the formulation, glycine (or arginine, or combinations thereof) as the sole stabilizer among the non-surfactant stabilizers referenced earlier, and polysorbate 80. In this formulation, the amount of adalimumab is 20 to 150 mg/ml, the amount of histidine buffer is up to about 50 mM; the amount of glycine is up to about 300 mM; and the amount of polysorbate 80 is in the range of about 0.01 to about 0.2 wt %. Optionally, this formulation may include up to about 100 mM NaCl. The present invention also contemplates modification of this formulation to combine the histidine buffer with one or more of citrate, acetate, phosphate, maleate, tartrate buffers.

In yet another embodiment, the adalimumab formulation of the present invention comprises, consists of, or consists essentially of, adalimumab, histidine buffer as the sole buffer, mannitol (or sorbitol or trehelose), and polysorbate 80, and further being free or substantially free of the non-surfactant stabilizers (e.g. glycine, arginine, etc.) referenced above. In this formulation, the amount of adalimumab is 20 to 150 mg/ml; the amount of histidine buffer is up to about 50 mM; the amount of polyol is up to about 300 mM; and the amount of polysorbate 80 is in the range of about 0.01 to about 0.2 wt %. Optionally, this formulation may include up to about 100 mM NaCl. The present invention also contemplates modification of this formulation to combine the histidine buffer with one or more of citrate, acetate, phosphate, maleate, tartrate buffers.

In a method aspect, the invention is directed to a method for enhancing long term stability in an aqueous, buffered adalimumab formulation, comprising one or more of the steps of: (a) incorporating histidine buffer, succinate buffer, or a combination thereof, in the formulation based on empirical data indicating that such buffers contribute to the stability of the formulation to a greater extent than other buffers or buffer combinations; or (b) incorporating glycine, arginine or a combination thereof as stabilizers in the formulation, based upon empirical data indicating that such stabilizer contribute to the stability of the formulation to a greater extent than other stabilizers; or (c) substantially excluding the presence of buffer or buffer combinations comprising citrate buffer (especially buffer combinations comprising both citrate and phosphate) based upon empirical data indicating that such buffer or buffer combinations perform poorly in terms of stabilizing the formulation in comparison to other buffers. The method may further comprise the selection of PS 80 as a surfactant based on empirical data indicating that PS 80 imparts better thermal stability to the adalimumab formulation than other surfactants, including PS 20. The method is useful to obtain a formulation of adalimumab that exhibits long term stability comparable to or better than commercially available adalimumab formulations marketed under the trademark Humira®.

In a further method aspect, the invention is directed to a method for treating an inflammatory condition in a subject which comprises administering to such subject any of the adalimumab formulation embodiments as described herein.

In the foregoing embodiments, where the above referenced stabilizers may be included in the formulations, it is further discovered that satisfactory stabilization can be attained when such stabilizers are used in place of both polyol and surfactant and hence stabilized formulations of the present invention can be free or substantially free of both polyol and surfactant. Accordingly, in a sixth embodiment, the invention provides a stable aqueous pharmaceutical composition comprising adalimumab, optionally a buffer, a stabilizer selected from the group consisting of an amino acid, a salt, EDTA, and a metal ion, and wherein said composition has a pH of about 4 to about 8, and preferably 5 to about 6, and wherein said composition is either substantially free of both polyol and surfactant. When buffer is present in this embodiment, it is especially preferred that (i) the buffer not include the combination of citrate and phosphate; (ii) the buffer is selected from the group consisting of histidine and succinate; and (iii) the stabilizer does not comprise sodium chloride, but instead is at least one member selected from the group consisting of arginine and glycine.

Important aspects of the present invention in certain embodiments include (i) that sorbitol and trehalose are discovered to be significantly better stabilizers of adalimumab formulations than mannitol, unless mannitol is used at concentrations in excess of about 200-300 mM in which case the three are generally equivalent; (ii) arginine and glycine (and combinations) are discovered to be significantly better stabilizers of adalimumab formulations than sodium chloride; and; (iii) when buffers are used in the formulation, it is discovered that the combination of citrate and phosphate is surprisingly significantly poorer in stabilizing adalimumab than other buffers such as succinate, histidine, phosphate and tartrate. The relatively poor performance of the buffer combination of citrate and phosphate is rather unexpected considering the apparent importance attributed to the use of a citrate/phosphate combined buffer in U.S. Pat. No. 8,216,583. To the contrary, we have now found that a phosphate/citrate buffer combination is not an optimal choice for obtaining a stabilized adalimumab formulation, and in fact, an element of our invention is the discovery that this combination should be avoided altogether in favor of other buffer systems.

Preferably, a polyol is a sugar alcohol; and even more preferably, the sugar alcohol is selected from the group consisting of mannitol, sorbitol and trehalose. However, as between mannitol and sorbitol, the invention has discovered, as noted above, a distinct stabilization advantage in using sorbitol or trehalose instead of mannitol, unless mannitol is used at concentrations in excess of about 200 mM, in which case mannitol, sorbitol and trehalose are generally equivalent. At concentrations below about 200 mM, mannitol has been found to be a poorer stabilizer than sorbitol or trehalose in an adalimumab formulation.

Preferably, a surfactant is a polysorbate or poloxamer; and even more preferably PS 80, PS 40, PS20, Pluronic F-68 and combinations. We have discovered a distinct and surprising thermal stabilization advantage in selecting PS 80 instead of PS-20.

These and other aspects will become apparent from the following description of the various embodiments, although variations and modifications therein may be affected without departing from the spirit and scope of the novel concepts of the disclosure.

It is to be understood that both the foregoing general description and the following detailed description are exemplary and explanatory only and are not restrictive of the invention, as claimed. Further representative embodiments are set forth in the numerous formulation studies reported in the detailed description, as well as the various embodiments listed in Appendices A, B and C attached hereto and made a part hereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
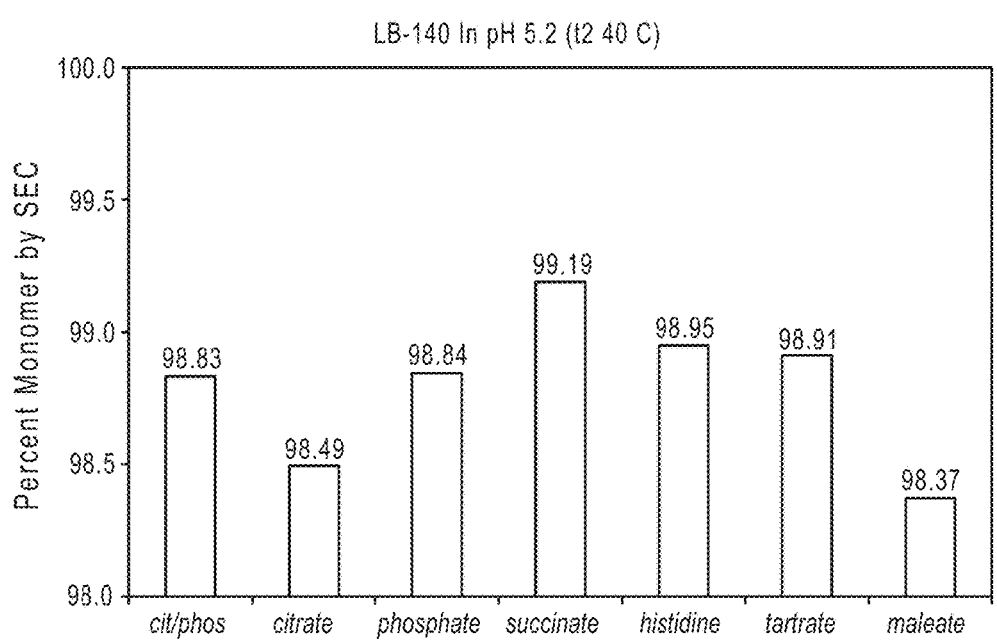
FIG. 1 is a bar chart of stability of various adalimumab formulations as determined by size exclusion chromatography (SEC).

Various embodiments of the invention are now described in detail. As used in the description and throughout the claims, the meaning of "a", "an", and "the" includes plural reference unless the context clearly dictates otherwise. Also, as used in the description and throughout the claims, the meaning of "in" includes "in" and "on" unless the context clearly dictates otherwise. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. The invention is not limited to the various embodiments given in this specification.

Unless otherwise defined, all technical and scientific terms used herein have the same meaning as commonly understood by one of ordinary skill in the art to which this invention pertains. In the case of conflict, the present document, including definitions will control.

"Around," "about" or "approximately" shall generally mean within 20 percent, within 10 percent, within 5, 4, 3, 2 or 1 percent of a given value or range. Numerical quantities given are approximate, meaning that the term "around," "about" or "approximately" can be inferred if not expressly stated.

The term "adalimumab" is synonymous with the active pharmaceutical ingredient in Humira® as well as protein considered or intended as biosimilar or bio-better variants thereof. Adalimumab is a recombinant human IgG1 monoclonal antibody specific for human TNF. Adalimumab is also known as D2E7. Adalimumab has two light chains, each with a molecular weight of approximately 24 kilodaltons (kDa) and two IgG1 heavy chains each with a molecular weight of approximately 49 kDa. Each light chain consists of 214 amino acid residues and each heavy chain consists of 451 amino acid residues. Thus, adalimumab consists of 1330 amino acids and has a total molecular weight of approximately 148 kDa. The term adalimumab is also intended to encompass so-called bio-similar or bio-better variants of the adalimumab protein used in commercially available Humira®. For example, a variant of commercial Humira® may be acceptable to the FDA when it has essentially the same pharmacological effects as commercially available Humira®, even though it may exhibit certain physical properties, such as glycosylation profile, that may be similar if not identical to Humira®.

For the purposes of the present application, the term "adalimumab" also encompasses adalimumab with minor modifications in the amino acid structure (including deletions, additions, and/or substitutions of amino acids) or in the glycosylation properties, which do not significantly affect the function of the polypeptide. The term "adalimumab" encompasses all forms and formulations of Humira®, including but not limited to concentrated formulations, injectable ready-to-use formulations; formulations reconstituted with water, alcohol, and/or other ingredients, and others.

The term "human TNFα" (which may be abbreviated as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) Nature 312:724-729; Davis, J. M., et al. (1987) Biochemistry 26:1322-1326; and Jones, E. Y., et al. (1989) Nature 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.).

The term "antibody", as used herein, refers to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In one embodiment of the invention, the formulation contains an antibody with CDR1, CDR2, and CDR3 sequences like those described in U.S. Pat. Nos. 6,090,382; 6,258,562, and 8,216,583.

An antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

The term "isolated antibody", as used herein, refers to an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may, however, have cross-reactivity to other antigens, such as TNFα molecules from other species. Moreover, an isolated antibody may be substantially free of other cellular material and/or chemicals.

The term "glycine" refers to an amino acid whose codons are GGT, GGC, GGA, and GGG.

The term "arginine" refers to an α-amino acid whose codons are CCU, CCC, CCA, and CCG.

The term "alanine" refers to an amino acid whose codons are GCT, GCC, GCA, and GCG.

The term "methionine" refers to an amino acid whose codon is ATG.

The term "glutamate" refers to an amino acid whose codons are GAA and GAG.

The term "sugar" refers to monosaccharides, disacharides, and polysaccharides. Examples of sugars include, but are not limited to, sucrose, glucose, dextrose, and others.

The term "polyol" refers to an alcohol containing multiple hydroxyl groups. Examples of polyols include, but are not limited to, mannitol, sorbitol, and others.

The term "metal ion" refers to a metal atom with a net positive or negative electric charge. For the purposes of the present application, the term "metal ion" also includes sources of metal ions, including but not limited to metal salts.

The term "long-term storage" or "long term stability" is understood to mean that the pharmaceutical composition can be stored for three months or more, for six months or more, and preferably for one year or more, most preferably a minimum stable shelf life of at least two years. Generally speaking, the terms "long term storage" and "long term stability" further include stable storage durations that are at least comparable to or better that the stable shelf typically required for currently available commercial formulations of adalimumab, without losses in stability that would render the formulation unsuitable for its intended pharmaceutical application. Long-term storage is also understood to mean that the pharmaceutical composition is stored either as a liquid at 2-8° C., or is frozen, e.g., at −20° C., or colder. It is also contemplated that the composition can be frozen and thawed more than once.

The term "stable" with respect to long-term storage is understood to mean that adalimumab contained in the pharmaceutical compositions does not lose more than 20%, or more preferably 15%, or even more preferably 10%, and most preferably 5% of its activity relative to activity of the composition at the beginning of storage.

The term "substantially free" means that either no substance is present or only minimal, trace amounts of the substance are present which do not have any substantial impact on the properties of the composition. If reference is made to no amount of a substance, it should be understood as "no detectable amount".

The term "mammal" includes, but is not limited to, a human.

The term "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed and is compatible with other ingredients of the formulation.

The term "composition" refers to a mixture that usually contains a carrier, such as a pharmaceutically acceptable carrier or excipient that is conventional in the art and which is suitable for administration into a subject for therapeutic, diagnostic, or prophylactic purposes. It may include a cell culture in which the polypeptide or polynucleotide is present in the cells or in the culture medium. For example, compositions for oral administration can form solutions, suspensions, tablets, pills, capsules, sustained release formulations, oral rinses or powders.

The terms "pharmaceutical composition" and "formulation" are used interchangeably.

The term "treatment" refers to any administration or application of remedies for disease in a mammal and includes inhibiting the disease, arresting its development, relieving the disease, for example, by causing regression, or restoring or repairing a lost, missing, or defective function; or stimulating an inefficient process. The term includes obtaining a desired pharmacologic and/or physiological effect, covering any treatment of a pathological condition or disorder in a mammal. The effect may be prophylactic in terms of completely or partially preventing a disorder or symptom thereof and/or may be therapeutic in terms of a partial or complete cure for a disorder and/or adverse affect attributable to the disorder. It includes (1) preventing the disorder from occurring or recurring in a subject who may be predisposed to the disorder but is not yet symptomatic, (2) inhibiting the disorder, such as arresting its development, (3) stopping or terminating the disorder or at least its associated symptoms, so that the host no longer suffers from the disorder or its symptoms, such as causing regression of the disorder or its symptoms, for example, by restoring or repairing a lost, missing or defective function, or stimulating an inefficient process, or (4) relieving, alleviating or ameliorating the disorder, or symptoms associated therewith, where ameliorating is used in a broad sense to refer to at least a reduction in the magnitude of a parameter, such as inflammation, pain and/or tumor size.

The term "disease" refers to any condition, infection, disorder or syndrome that requires medical intervention or for which medical intervention is desirable. Such medical intervention can include treatment, diagnosis and/or prevention.

The term "therapeutically effective amount" refers to an amount which, when administered to a living subject, achieves a desired effect on the living subject. For example, an effective amount of the polypeptide of the invention for administration to the living subject is an amount that prevents and/or treats an integrin $\alpha v \beta 3$-mediated disease. The exact amount will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art.

Embodiments of the Invention

When pharmaceutical compositions containing adalimumab (Humira®), including aqueous and lyophilized formulations of adalimumab are stored on a long-term basis, the activity of adalimumab can be lost or decreased due to aggregation and/or degradation. Thus, the present invention provides aqueous formulations of adalimumab that allow stable long-term storage of adalimumab, so that adalimumab is stable over the course of storage either in liquid or frozen states. The provided formulations do not require any extra steps such as rehydrating.

Numerous embodiments of the present invention are explained in a greater detail below.

Adalimumab

All of the compositions of the present invention comprise adalimumab. As explained in the Background section of this application, adalimumab is a recombinant human IgG1 monoclonal antibody specific for human tumor necrosis factor (TNF). This antibody is also known as D2E7. Adalimumab consists of 1330 amino acids and has a molecular weight of approximately 148 kilodaltons. Adalimumab has been described and claimed in U.S. Pat. No. 6,090,382. The term "adalimumab" is also intended to mean so-called "bio-similar" and "bio-better" versions of the active adalimumab protein present in commercially available Humira®.

Adalimumab suitable for storage in the present pharmaceutical composition can be produced by standard methods known in the art. For example, U.S. Pat. Nos. 6,090,382 and 8,216,583 describe various methods that a skilled artisan could use to prepare adalimumab protein for use in the formulations of the present invention. These methods are incorporated by reference herein. For example, adalimumab can be prepared by recombinant expression of immunoglobulin light and heavy chain genes in a host cell.

Purification of the expressed adalimumab can be performed by any standard method. When adalimumab is produced intracellularly, the particulate debris is removed, for example, by centrifugation or ultrafiltration. When adalimumab is secreted into the medium, supernatants from such expression systems can be first concentrated using standard polypeptide concentration filters. Protease inhibitors can also be added to inhibit proteolysis and antibiotics can be included to prevent the growth of microorganisms.

Adalimumab can be purified using, for example, hydroxyapatite chromatography, gel electrophoresis, dialysis, and affinity chromatography, and any combination of known or yet to be discovered purification techniques, including but not limited to Protein A chromatography, fractionation on an ion-exchange column, ethanol precipitation, reverse phase HPLC, chromatography on silica, chromatography on heparin SEPHAROSET®, an anion or cation exchange resin chromatography (such as a polyaspartic acid column), chromatofocusing, SDS-PAGE, and ammonium sulfate precipitation.

I Formulations of Adalimumab with a Polyol and/or Surfactant, but without a Citrate/Phosphate Buffer In a first embodiment, the invention provides a stable aqueous pharmaceutical composition comprising adalimumab; a stabilizer comprising at least one member selected from the group consisting of a polyol and a surfactant; and a buffer selected from the group consisting of citrate, phosphate, succinate, histidine, tartrate and maleate, wherein said composition has a pH of about 4 to about 8, and preferably about 5 to about 6, and wherein said buffer does not comprise a combination of citrate and phosphate. In this embodiment, the stabilizer preferably comprises both polyol and surfactant. The pharmaceutical composition can comprise one, or any combination of two or more buffers, as long as it does not comprise both citrate and phosphate. The surfactant may be any pharmaceutically acceptable surfactant, preferably polysorbates (e.g., polysorbate 80) or poloxamers (e.g., Pluronic F-68).

II Formulations of Adalimumab Using a Single Buffer System

In a second embodiment, utilizing a single buffer system, the invention provides a stable aqueous pharmaceutical composition comprising adalimumab, a polyol, a surfactant, and a buffer system comprising a single buffering agent, said single buffering agent being selected from citrate, phosphate, succinate, histidine, tartrate or maleate, but not including combinations of the foregoing; wherein the formulation has a pH of about 4 to 8, and preferably about 5 to about 6. Histidine and succinate are particularly preferred for use as single buffering agents. It was surprisingly discovered that adalimumab compositions which comprise only one buffer (as opposed to two or more buffers) are more stable than adalimumab compositions comprising both a citrate buffer and a phosphate buffer. In the single buffer embodiment, adalimumab can be present at a concentration from about 20 to about 150 mg/ml, more preferably from about 20 to about 100 mg/ml, and even more preferably from about 30 to about 50 mg/ml. The buffer is present at a concentration from about 5 mM to about 50 mM. The pH of the compositions is between about 5 and about 6. The single buffer compositions of the invention may further comprise a stabilizer selected from the group consisting of an amino acid, a salt, ethylenediaminetetraacetic acid (EDTA) and a metal ion. The amino acid is selected from the group consisting of glycine, alanine, glutamate, arginine and methionine, most preferably glycine, arginine and methionine. The salt is selected from the group consisting of sodium chloride and sodium sulfate. The metal ion is selected from the group consisting of zinc, magnesium and calcium. The compositions of the invention may further comprise a surfactant. The surfactant is a polysorbate surfactant or a poloxamer surfactant. Polysorbate surfactants include polysorbate 80, polysorbate 40 and polysorbate 20. A preferred polysorbate surfactant is polysorbate 80. Poloxamer surfactants include poloxamer 188 (also available commercially as Pluronic F-68). Most preferably, the surfactant is polysorbate 80. The single buffer composition may further comprise a polyol. Preferably, the polyol is a sugar alcohol; and even more preferably, the sugar alcohol is mannitol, sorbitol or trehalose. The single buffer adalimumab composition may also comprise a sugar, preferably sucrose, glucose or dextrose.

In one embodiment of a single buffer adalimumab formulation, the invention provides a stable aqueous pharmaceutical composition comprising adalimumab at a concentration from about 20 and about 150 mg/ml, polysorbate 80 at a concentration from about 1 to 50 μM, and succinate at a concentration from about 5 mM and about 50 mM, wherein said composition has a pH of about 5 to about 5.5, and wherein said composition is substantially free of any other buffers.

In another embodiment of a single buffer adalimumab formulation, the invention provides a stable aqueous pharmaceutical composition comprising adalimumab at a concentration from about 20 and about 150 mg/ml, polysorbate 80 at a concentration from about 1 to 50 μM, and histidine at a concentration from about 5 mM and about 50 mM, wherein said composition has a pH of about 5 to about 5.5, and wherein said composition is substantially free of any other buffers.

In a further embodiment of a single buffer adalimumab formulation, the invention provides a stable aqueous pharmaceutical composition comprising adalimumab at a concentration from about 20 and about 150 mg/ml, polysorbate 80 at a concentration from about 1 to 50 μM, and either tartrate, maleate or acetate at a concentration from about 5 mM and about 50 mM, wherein said composition has a pH of about 5 to about 5.5, and wherein said composition is substantially free of any other buffers.

III Formulations of Adalimumab which Exclude Buffer

In a third embodiment, the invention provides a stable aqueous pharmaceutical composition comprising adalimumab, a stabilizer comprising at least one member selected from a polyol and a surfactant, wherein said composition has a pH of about 4 to about 8 and preferably about 5 to about 6, and wherein said composition is substantially free of a buffer. The term "free of buffer" should be understood to allow inclusion of the inherent buffering effect of the protein itself. In a buffer free formulation, the stabilizers referenced above may also be present (e.g. glycine, arginine and combinations thereof).

IV Formulations of Adalimumab which Exclude Surfactant

In a fourth embodiment, the invention provides a stable aqueous pharmaceutical composition comprising adalimumab, a polyol, and a buffer selected from the group consisting of citrate, phosphate, succinate, histidine, tartrate and maleate, wherein said composition has a pH of about 4 to about 8 and preferably about 5 to about 6, and wherein said composition is free or substantially free of a surfactant. Preferably, the composition (i) does not contain the buffer combination of citrate and phosphate; and (ii) the buffer is at least one member selected from the group consisting of histidine and succinate; and (iii) the polyol is not mannitol at concentrations less than about 150 mM, but instead is selected from the group consisting of mannitol at concentrations exceeding about 150 mM, sorbitol and trehalose.

V Formulations of Adalimumab which Exclude Polyol

In a fifth embodiment, the invention provides a stable aqueous pharmaceutical composition comprising adalimumab, a surfactant, and a buffer selected from the group consisting of citrate, phosphate, succinate, histidine, tartrate and maleate, wherein said composition has a pH of about 4 to about 8, and preferably about 5 to about 6, and wherein said composition is substantially free of polyol. Preferably, the composition (i) does not contain the buffer combination of citrate and phosphate; and (ii) the buffer is at least one member selected from the group consisting of histidine and succinate.

Additional Stabilizers Useful in Embodiments I Through V.

Optionally, in each of the five embodiments summarized above, the composition may further comprise a stabilizer selected from the group consisting of an amino acid, a salt, ethylenediaminetetraacetic acid (EDTA) and a metal ion. The amino acid stabilizer may be selected from the group consisting of glycine, alanine, glutamate, arginine and methionine. The salt stabilizer may be selected from the group consisting of sodium chloride and sodium sulfate. The metal ion stabilizer may be selected from the group consisting of zinc, magnesium and calcium. Preferably, adalimumab formulations containing the stabilizers mentioned above also do not contain buffer systems in which phosphate buffer and citrate buffer are present in combination. Most preferably (i) the optional additional stabilizer present in this embodiment is not sodium chloride, and comprises at least one or both of arginine and glycine; (ii) the buffer, when present, contains no citrate and phosphate combination but is instead at least one of histidine and succinate; and (iii) the stabilizer when it includes a polyol is not mannitol unless in amounts greater than about 150 mM, and may also include trehalose and sorbitol. Preferably the amount of mannitol is greater than about 150 mM, and most preferably greater than about 200 mM.

VI Formulations of Adalimumab Replacing Both Surfactant and Polyol with Other Stabilizers It has been further discovered that satisfactory stabilization can be attained when the stabilizers mentioned above are used in place of both polyol and surfactant, accordingly, in a sixth embodiment, the invention provides a stable aqueous pharmaceutical composition comprising adalimumab, optionally a buffer, a stabilizer selected from the group consisting of an amino acid, a salt, EDTA, and a metal ion, and wherein said composition has a pH of about 4 to about 8, and preferably about 5 to about 6, and wherein said composition is free or substantially free of a polyol and surfactant. When buffer is present in this embodiment, it is especially preferred that (i) the buffer not include the combination of citrate and phosphate; (ii) the buffer is selected from the group consisting of histidine and succinate; and (iii) the stabilizer does not comprise sodium chloride, but instead is at least one member selected from the group consisting of arginine and glycine. It is also preferred that the buffer is free or substantially free of citrate buffer, as we have discovered that it is generally poorer in terms of stability contribution than other buffers, such as histidine and succinate.

In each of the embodiments above at least one of the following advantageous conditions can be optionally present (unless stated as being required): (i) the buffer preferably does not contain a combination of citrate and phosphate, or is free or substantially free of citrate buffer (ii) the buffer preferably is at least one member selected from the group consisting of histidine and succinate; and (iii) the stabilizer preferably does not include sodium chloride, or if present is controlled to levels less than about 100 mM; (iv) the stabilizer is at least one member selected from the group consisting of arginine and glycine, including combinations thereof; and (v) the polyol is preferably not mannitol (unless mannitol is present in amounts greater than about 150 mM and preferably greater than about 200 mM) but may include sorbitol and trehalose. When using polyols for stabilization, mannitol is discovered herein to be destabilizing in comparison to sorbitol and trehalose unless the mannitol is present in amounts generally above about 150 to 200 mM. When using other stabilizers, it is discovered herein that sodium chloride is destabilizing compared to arginine or glycine, but we observe some stabilization when the levels of sodium chloride are controlled to less than about 100 mM and preferably less than about 75 mM.

Preferably, adalimumab is present in the composition of the present invention at a concentration from about 20 to about 150 mg/ml, more preferably from about 20 to about 100 mg/ml, and even more preferably from about 30 to about 50 mg/ml.

Buffer, if present, is present at a concentration from about 5 mM to about 50 mM.

Surfactant, if present, is preferably a polysorbate (PS). In an even more preferred embodiment, the polysorbate is polysorbate 80 (PS 80). Poloxamer surfactants are also suitable (e.g., Pluronic® F-68).

The polyol, if present, is a sugar alcohol. In an even more preferred embodiment, the sugar alcohol is selected from the group consisting of mannitol, sorbitol and trehalose, and most preferably sorbitol and trehalose.

Preferably, the polyol is at a concentration from about 1 to about 10%, more preferably, from about 2 to about 6%, and even more preferably from about 3 to 5%, wherein said values are weight by volume (w/v) of the total composition.

A stabilizer, when present, can be selected from the group consisting of an amino acid, a salt, ethylenediaminetetraacetic acid (EDTA) and a metal ion. The amino acid can be selected from the group consisting of glycine, alanine, glutamate, arginine and methionine. The salt may be selected from the group consisting of sodium chloride and sodium sulfate. The metal ion may be selected from the group consisting of zinc, magnesium and calcium. Glycine and arginine are particularly preferred stabilizers.

Zinc, magnesium and calcium, when present for stabilization, may be at a concentration from about 1 mM to about 100 mM, and more preferably from about 1 to about 10 mM.

Glycine, or arginine, or combinations thereof, if present for stabilization, is at a total concentration of up to about 300 mM, and preferably about 150 to 300 mM.

Methionine, if present for stabilization, is present at a concentration from about 1 to about 10 mg/ml, more preferably from about 1 mg/ml to about 5 mg/ml.

Sodium chloride, if present for stabilization, is at a concentration from about 5 to about 150 mM, more preferably, from about 20 to about 140 mM, and even more preferably less than about 100 mM.

Sodium sulfate, if present if present for stabilization, is at a concentration from about 5 to about 150 mM, more preferably, from about 20 to about 120 mM, and even more preferably from about 60 to about 100 mM.

EDTA, if present for stabilization, is present at a concentration from about 0.01% to about 0.05%, more preferably from about 0.05% to about 0.25%, and even more preferably from about 0.08% to about 0.2%.

Preferably, the pH of the composition is from about 5 to about 5.5; and even more preferably is about 5.2 to 5.4.

In an example of Embodiment I and II, above, the invention provides a stable aqueous pharmaceutical composition comprising adalimumab at a concentration from about 20 and about 150 mg/ml, sorbitol or trehalose at a concentration from about 1 to 10% weight by volume, polysorbate 80 at a concentration from about 1 to 50 µM, and at least one of succinate, histidine, phosphate, tartrate, maleate or citrate buffer, at a concentration from about 5 mM to about 50 mM, wherein said composition has a pH of about 5 to about 5.5, and provided said composition is free or substantially free of citrate/phosphate buffer combination. Further, we rank citrate as the poorest of buffers, and preferably avoid it although it is still within the scope of the invention to formulate stable formulations of adalimumab that include citrate buffer, if not the combination thereof with phosphate.

In an example of Embodiment IV, the invention provides a stable aqueous pharmaceutical composition comprising adalimumab at a concentration from about 20 and about 150 mg/ml, sorbitol or trehalose at a concentration from about 1 to 10% weight by volume, and at least one of succinate, histidine, phosphate, tartrate, maleate or citrate buffer, at a concentration from about 5 mM to about 50 mM, wherein said composition has a pH of about 5 to about 5.5, and wherein said composition is substantially free of a surfactant and, optionally, and preferably, free or substantially free of citrate/phosphate buffer combination.

In an example of Embodiment VI, the invention provides a stable aqueous pharmaceutical composition comprising adalimumab at a concentration from about 20 and about 150 mg/ml, glycine at a concentration from about 20 to about 200 mM, and at least one of succinate, histidine, phosphate, tartrate, maleate or citrate buffer, at a concentration from about 5 mM to about 50 mM, wherein said composition has a pH of about 5 to about 5.5, and wherein said composition is free or substantially free polyol; surfactant (e.g. PS8) is preferably, but optionally present; and the composition is, optionally, and preferably, free or substantially free of citrate/phosphate buffer combination.

In a further example of Embodiment VI, the invention provides a stable aqueous pharmaceutical composition comprising adalimumab at a concentration from about 20 and about 150 mg/ml, arginine or glycine at a concentration from about 1 to about 250 mM, and at least one of succinate, histidine, phosphate, tartrate, maleate or citrate buffer, at a concentration from about 5 mM and about 50 mM wherein said composition has a pH of about 5 to about 5.5, and wherein said composition is substantially free of polyol. Surfactant (e.g. PS80) is preferably but optionally present, and the composition is, optionally, and preferably, free or substantially free of citrate/phosphate buffer combination.

In a further example of Embodiment VI, the invention provides a stable aqueous pharmaceutical composition comprising adalimumab at a concentration from about 20 and about 150 mg/ml, sodium chloride at a concentration from about 5 to about 150 mM, and at least one of succinate, histidine, phosphate, tartrate, maleate or citrate buffer, at a concentration from about 5 mM and about 50 mM wherein said composition has a pH of about 5 to about 5.5, and wherein said composition is free or substantially free of a polyol. Surfactant (e.g. PS80) is preferably but optionally present; and the composition is, optionally, and preferably, free or substantially free of citrate/phosphate buffer combination.

In an example of Embodiment V, the invention provides a stable aqueous pharmaceutical composition comprising adalimumab at a concentration from about 20 and about 150 mg/ml, sodium chloride at a concentration from about 5 to about 150 mM, polysorbate 80 at a concentration from about 1 to 50 µM, and at least one of succinate, histidine, phosphate, tartrate, maleate or citrate buffer, at a concentration from about 5 mM and about 50 mM wherein said composition has a pH of about 5 to about 5.5, and wherein said composition is free or substantially free of a polyol and, optionally, and preferably, free or substantially free of citrate/phosphate buffer.

In an example of Embodiments I and II, with additional stabilization, the invention provides a stable aqueous pharmaceutical composition comprising adalimumab at a concentration from about 20 and about 150 mg/ml, polysorbate 80 at a concentration from about 1 to about 50 µM, sorbitol or trehalose at a concentration from about 1 to about 10% weight by volume, EDTA at a concentration from about 0.01% to about 0.5%, and at least one of succinate, histidine, phosphate, tartrate, maleate or citrate, as a sole buffer, at a concentration from about 5 mM and about 50 mM wherein said composition has a pH of about 5 to about 5.5, and wherein the composition is free, or substantially free of citrate/phosphate buffer combination.

In a further example of Embodiments I and II, with additional stabilization, the invention provides a stable aqueous pharmaceutical composition comprising adalimumab at a concentration from about 20 and about 150 mg/ml, polysorbate 80 at a concentration from about 1 to about 50 µM, sorbitol or trehalose at a concentration from about 1 to about 10% weight by volume, methionine at a concentration from about 1 to about 10 mg/ml, %, and at least one of succinate, histidine, phosphate, tartrate, maleate or citrate at a concentration from about 5 mM and about 50 mM wherein said composition has a pH of about 5 to about 5.5, wherein the composition is free or substantially free of any citrate/phosphate buffer combination.

In a further example of Embodiments I and II, with additional amino acid stabilization, the invention provides a stable aqueous pharmaceutical composition comprising adalimumab at a concentration from about 20 and about 150 mg/ml, polysorbate 80 at a concentration from about 1 to about 50 µM, mannitol, sorbitol or trehalose (preferably sorbitol) at a concentration from about 1 to about 10% weight by volume, and amino acid that is preferably one and not both of (a) arginine at a concentration from about 1 to about 250 mg/ml, and (b) glycine at a concentration of about 20 to 200 mg/ml, and histidine buffer or succinate buffer at a concentration from about 5 mM and about 50 mM, and wherein said composition has a pH of about 5 to about 5.5; and wherein the composition is free or substantially free of any citrate/phosphate buffer combination.

In a further example of Embodiment IV, with additional amino acid stabilization, the invention provides a stable aqueous pharmaceutical composition comprising adalimumab at a concentration from about 20 and about 150 mg/ml, polysorbate 80 at a concentration from about 1 to about 50 µM, arginine at a concentration from about 1 to about 250 mg/ml, glycine at a concentration of about 20 to 200 mg/ml, and histidine buffer or succinate buffer at a concentration from about 5 mM to about 50 mM, and wherein said composition has a pH of about 5 to about 5.5 and is free or substantially free of polyol; and, optionally, wherein the composition is preferably free of any citrate/phosphate buffer combination.

Numerous embodiments of the adalimumab formulations of the present invention were prepared in eight separate blocks of experiments, referred to herein as "Block A" through "Block H." Each block had 12 to 16 different formulations that were exposed to accelerated storage conditions, 1 week at 40° C. and 2 weeks at 25° C. For each time point the chemical and physical stability of the adalimumab protein was measured by SEC, RP, UV, pH, CE-IEF and CE-SDS.

Materials and Methods

1. Equipment Used in the Formulation Studies

| Equipment | Manufacture | Model | Serial Number |
| --- | --- | --- | --- |
| Balance | Sartorius | CPA124S | 23350022 |
| pH meter | Denver Instrument | Model 250 | E25006B100 |
| UV | Cary | Bio 100 | EL07103025 |
| HPLC | Dionex 3 | Ultimate 3000 UPLC | 8047439 |
| HPLC | Dionex 2 | Ultimate 3000, UPLC | 8036991 |
| Beckman CE | Beckman | P/ACE | 455436 |
| Agilent CE | Agilent | 3DCE 1600A | 3546G00736 |
| Rocker Plate | Labnet | Orbit P4 | 8091840 |

2. Chemicals and Materials Used in the Formulation Studies

| Chemical/Materials | Producer | Purity | Lot Number: |
| --- | --- | --- | --- |
| Citrate | Mallinckrodt | ACS | H28475 |
| Phosphate | Fisher | FCC | 103372 |
|  | Fisher | ACS | 113670 |
| Succinate | Spectrum | Reagent | ZM0462 |
| Histidine | Spectrum | USP | XV0239 |
|  | Spectrum | USP | ZG0216 |
| Tartrate | Spectrum | FCC | 1BC0152 |
| Maleate | TCI | >99% | 206-738-1 |
| Mannitol | BDH | USP | 57910 |
| Glycine | Spectrum | FCC | YM3312 |
|  | Spectrum | FCC | 1BJ0243 |
|  | Fisher | Tissue Grade | 070082 |
| Arginine | Spectrum | USP | 2AK0238 |
|  | Spectrum | USP | 1CB0771 |
| Sodium Chloride | Mallinckrodt | ACS | J52619 |
|  | Macron | USP | 26434 |
| Polysorbate 80 | Sigma-Aldrich | Low Peroxide | 028K5309 |
| Sorbitol | Spectrum | NF | 1AH0521 |
| Trehalose | Spectrum | N/A | 1AE0739 |
| Acetate | Mallinckrodt | FCC | H31613 |
| EDTA | Sigma | 98.5% | 057K00071 |
| Methionine | Spectrum | USP | ZF0377 |
| F-68 | Sigma | Cell Culture | 057K00331 |
| Polysorbate 20 | Spectrum | NF | 1AE0882 |
| Sodium dodecyl sulfate | Fluka | ACS | 1344034 |
| Tris base | Fisher | ACS | S61374 |
| 2-mercaptoethanol | Fisher | Electrophoresis | 107667 |

| Material/Reagents | Part Number | Supplier |
| --- | --- | --- |
| Slide-A-Lyzers 7K cutoff | 66373 | Thermo |
| Mini Dialysis Units | 69550 | Thermo |
| Millex ®-GV 0.22 μM, Filter | SLGV004SL | Millipore |
| 1 mL Vials | 4500050375 | SCHOTT |
| cIEF Gel Polymer Solution | 477497 | Beckman Coulter |
| pI Marker Kit | A58481 | Beckman Coulter |
| Pharmalyte 3-10 ampholyte | 17-0456-01 | GE Healthcare |
| Fused silica capillary (50 μm i.d.) | TSP050375 | Polymicro |
| SDS-MW gel buffer | A10663 | Beckman |
| 10 kD internal standard | A26487 | Beckman |

3. HPLC Columns Used in the Formulation Studies

| Column | Company | Part # | Lot |
| --- | --- | --- | --- |
| Poroshell 300SB-C8, 2.1 × 75 mm, 5 um | Agilent | 660750-906 | USZW003083 |
| Poroshell 300SB-C8, 2.1 × 75 mm, 5 um | Agilent | 660750-906 | USZW003073 |
| ACQUITY UPLC BEH200 SEC, 1.7 um Column, 4.6 × 150 mm | Waters | 186005225 | 138123331 |
| ACQUITY UPLC BEH200 SEC, 1.7 um Column, 4.6 × 150 mm | Waters | 186005225 | 01471130951 |

Processing of Humira®.

Block A experiments used adalimumab present in commercially available Humira®. Humira® material was dialyzed as follows: 100 μL of Humira® was placed into Mini Dialysis units with a 3.5 MWCO and dialyzed in 1 L of formulation buffer for 24 hours at 4 to 8° C. A few samples did experience a small increase in volume due to the dialysis, but never to extent that the concentration of the polysorbate 80 dropped below the CMC (critical micelle concentration).

The protein concentration for each formulation was measured by UV absorbance spectroscopy, using an calculated experimental molar absorptivity based on reported concentration of Humira®, 50 mg/mL. For a number of the formulations the protein concentration was adjusted by using a spin concentrator. The sample was placed in the spin concentrator and rotated at 14,000 RPM for 30 to 60 secs. The protein concentration was then checked with UV. After the targeted protein concentration around 50 mg/mL was reached the samples were filtered through a 0.22 μM sterile filter into sterile vials in a biosafety hood. The samples were then placed on stability at 40° C. for one and two weeks.

Processing of a Proprietary Adalimumab Protein.

The formulation studies described herein used a proprietary adalimumab biosimilar protein which did not contain polysorbate 80. The material was dialyzed using 7,000 MWCO Slide-A-Lyzers in different formulation buffers for 24 hours at a temperature range between 4 to 8° C. After dialysis the protein concentration was measured by UV and sample pH was measured. The target concentration of samples was 50±2.5 mg/mL, which was adjusted if the sample concentration fell out of the above range. Some of the samples did experience an increase in sample volume do to dilution, requiring the concentration of the protein to increase. For these samples the protein concentration was increased by using spin concentrators, usually at 14,000 rpm for 30 to 60 secs. The pH of a number of samples were adjusted using 1M NaOH or 1M HCl to reach the target pH of 5.2.

After the targeted protein concentration and pH of the samples were determined to be within experimental parameters, the samples were filtered through a 0.22 µM sterile filter into sterile vials in a biosafety hood. The samples were then placed on stability at 40° C. for one week and 25° C. for two weeks.

Freeze-Thaw Conditions:

The freeze thaw samples were prepared on the day of analysis to match with t=0. The samples were frozen at −80° C. between 3 to 7 minutes. The frozen sample was then thawed at room temperature until all the ice had thawed. The freeze and thaw cycle was repeated 5 times for each sample.

Agitation Studies.

The samples were aggregated at 150 rpm for 24 hours at 4° C. on a rockerplate. A control was prepared and placed next to the rocker plate for each sample that underwent agitation.

pH Measurements.

The pH each sample was measured using a micro-pH probe. Before the start of analysis the pH probe was calibrated with three pH standards ordered from fisher. The pH values of the stability samples were measured by transferring 604 of each stability sample to 100 µL PCR tube. The micro-pH probe was then submerged into the sample and after the value stabilized it was recorded.

UV Absorbance Spectroscopy.

UV spectroscopy was used to measure the protein concentration in the samples. The mole extinction coefficient at 280 nm for bulk substance was 1.6355 mg/mL, which was determined experiential. The protein concentrations of the all formulations for LB-140 were measured using a cell path length of 0.0096 cm. Below is the analysis parameters used for LB-140.

Scan Range: 400 to 200 nm
Average Time (min): 0.1
Date Interval (nm): 1
Scan Rate (nm/min): 600
Cycle Count: 5

Size Exclusion Chromatography (SEC) Method.

The SEC method used to analyze the LB-140 stability samples was developed at Legacy BioDesign. Below is a brief summary of the SEC method parameter used for the analysis of the LB-140 samples.

Method Parameters
Column Information: ACQUITY UPLC BEH200 SEC, 1.7 um Column, 4.6×150 mm
Analysis Buffer: 50 mM Phosphate, 250 mM NaCl, pH 6.8
Flow rate: 0.3 mL/min
Column temperature: 30° C.
Detection: 280 nm
Injection volume: 2 µL
Sample temperature: Approx. 5° C.

RP HPLC Method.

The RP HPLC method was found to be stability indicating and was used to analyze LB-140 stability samples. Below is a summary of the RP method parameter used for the analysis of the LB-140.

Method Parameters
Column Information: Poroshell 300SB-C8, 2.1×75 mm, 5 um
Mobile Phase A: 98% (v/v) H2O/2% (v/v) IPA/0.1% (v/v) TFA
Mobile Phase B: 10% (v/v) H2O/70% (v/v) IPA/20% (v/v) ACN/0.1% (v/v) TFA
Flow rate: 0.25 mL/min
Column temperature: 80° C.
Detection: 225 nm
Injection volume: 1 µL
Sample temperature: Approx. 5° C.
Run time: 15 minutes
Gradient:

| Time | % A | % B |
| --- | --- | --- |
| 0 | 100 | 0 |
| 10 | 50 | 50 |
| 10.1 | 100 | 0 |
| 15 | 100 | 0 |

CE-IEF Analysis.

Capillary isoelectric focusing (cIEF) was conducted as described in the PA 800 plus Application Guide published by Beckman Coulter. A more detailed description can be found in a research article published by Mack et al[1]. All analyses were conducted using a Beckman Coulter P/ACE MDQ system (Beckman Coulter, Inc.; Brea, Calif.) operated at ambient temperature with a 30 cm total length (20 cm effective) neutral capillary. The neutral capillary was prepared by immobilizing poly(acrylamide) to the capillary wall using a method described by Gao et al.[2] cIEF samples were prepared by mixing the protein of interest at 0.25 mg/mL with a mixture of 3M urea-cIEF gel containing ampholyte, cathodic stabilizer, anodic stabilizer, and pI markers. Sample was pressure injected at 9.5 psi into the capillary for 4.1 min, after which time it was focused by applying a voltage of 25 kV for 15 min between analyte and catholyte. This step was followed by chemical mobilization at 30 kV for 30 min between analyte and chemical mobilizer. The pI markers and the protein of interest were detected with absorbance at 280 nm during the mobilization step. The pI of the protein was calculated from the resultant regression equation of pI vs. first peak moment obtained from the pI standards.

CE-SDS Analysis.

Analysis by CE-SDS was conducted under reducing conditions utilizing a method adapted from the SOP published by Beckman-Coulter for determining IgG purity/heterogeneity. Briefly, the antibody was diluted with DDI water to 6 mg/mL, denatured by adding sample buffer (0.1 M Tris/ 1.0% SDS, pH 8.0), and reduced via addition of 2-mercaptoethanol; the final antibody concentration was 1.2 mg/mL. Denaturing and reduction was facilitated by heating the sample at 70° C. for 10 min. The sample was cooled for 10 min at room temperature prior to analysis. A centrifuge step (300 g, 5 min) was employed prior to heating the sample and directly after the cooling it. CE analysis was conducted using a Beckman Coulter P/ACE MDQ system operated at ambient temperature with a 30 cm total length (20 cm effective, 50 µm i.d.) capillary. Prior to sample introduction, the capillary was sequentially rinsed with 0.1 M NaOH, 0.1M HCL, DDI water, and SDS-gel buffer solution. Sample was injected electrokinetically at 5 kV for 30 s followed by separation at 30 kV for 30 min. For both injection and separation, the instrument was operated in reverse polarity mode. Antibody fragments were detected using absorbance at 214 nm (4 Hz acquisition) and time-normalized areas reported for measured peaks.

Block A Formulation Studies

The Block A studies examined different buffer systems and used a commercially available adalimumab material which was reprocessed for these studies. We note that U.S. Pat. No. 8,216,583 references stability of an adalimumab formulation in relation to use of a citrate/phosphate buffer system at pH 5.2, and in fact the patent required the use of such a buffer combination. The work we have done, reflected here, indicates that citrate/phosphate is in fact a rather poor buffer choice in comparison to others such as histidine and succinate. In the Block A studies below, pH was kept constant at 5.2. The concentrations of mannitol and polysorbate 80 were also held constant. Samples were kept at 40° C. for two weeks. The study design is summarized in the Table below.

TABLE A

BLOCK A STUDY DESIGN

| Form No. | API | Citrate (mM) | Phosphate (mM) | Succinate (mM) | Histidine (mM) | Tartrate (mM) | Maleate (mM) | Mannitol (mM) | PS 80 (%) |
|---|---|---|---|---|---|---|---|---|---|
| 1 | Humira ® | 8 | 18 | 0 | 0 | 0 | 0 | 12 | 0.1 |
| 2 | Humira ® | 10 | 0 | 0 | 0 | 0 | 0 | 12 | 0.1 |
| 3 | Humira ® | 0 | 10 | 0 | 0 | 0 | 0 | 12 | 0.1 |
| 4 | Humira ® | 0 | 0 | 10 | 0 | 0 | 0 | 12 | 0.1 |
| 5 | Humira ® | 0 | 0 | 0 | 10 | 0 | 0 | 12 | 0.1 |
| 6 | Humira ® | 0 | 0 | 0 | 0 | 10 | 0 | 12 | 0.1 |
| 7 | Humira ® | 0 | 0 | 0 | 0 | 0 | 10 | 12 | 0.1 |

Analysis by SEC showed that the formulation with citrate alone performed more poorly than the buffer combination (Table A), indicating that the phosphate was the primary stabilizer in that combination. This was surprising and unexpected, as this pH is outside of the nominal buffering capacity range of phosphate, but well within the buffering range for citrate. Furthermore, succinate, histidine, and tartrate did as well or better than the citrate/phosphate combination, indicating that other buffer systems would provide equal or superior stability for adalimumab. Accordingly, the present invention in one of its embodiments is directed to adalimumab formulations exhibiting long term stability, wherein a buffer combination of citrate and phosphate is avoided in favor of at least one buffer selected from the group consisting of histidine, phosphate, succinate and tartrate. Acetate is also a suitable replacement for the citrate phosphate buffer combination.

Figure 2:
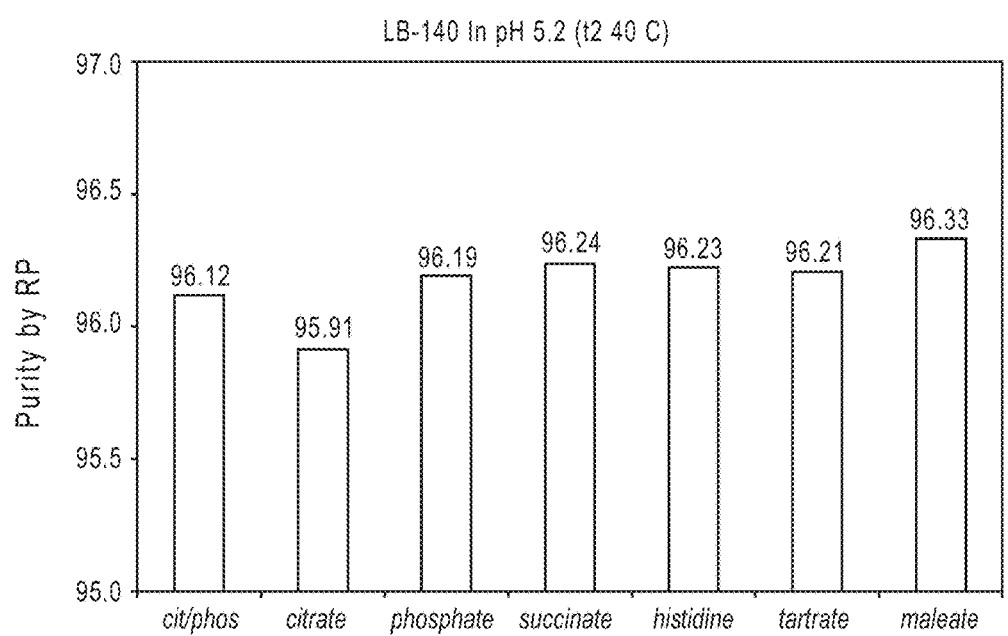
FIG. 2 is a bar chart of stability of various adalimumab formulations as determined by reversed phase (RP) high performance liquid chromatography (HPLC).

The purity of these stored samples was checked using RP HPLC (FIG. 2). As with SEC, the citrate formulation exhibited the poorest stability, while all of the other buffers did as well or better than the buffer combination found in commercially available adalimumab (Humira®). These results demonstrate our discovery that changing the buffer (i.e. avoiding the citrate/phosphate buffer combination of the commercial adalimumab) could improve the stability profile of adalimumab.

Block B Formulation Studies

A second study ("BLOCK B") was conducted examining just changes in the buffer species, where the pH (5.2) was not changed, as outlined in the table below labeled "BLOCK B Study Design. In this case, the commercially available formulation for Humira® was used as a control, while all of the other formulations employed a proprietary adalimumab biosimilar protein. Table B-1, below summarizes the percent monomer for the Block B formulations (as well the percentage amount of an impurity determined to be a fragment of the adalimumab protein).

TABLE B

BLOCK B STUDY DESIGN

| Form No. | API | Citrate (mM) | Phosphate (mM) | Succinate (mM) | Histidine (mM) | Tartrate (mM) | Maleate (mM) | Mannitol (mM) | PS 80 (%) |
|---|---|---|---|---|---|---|---|---|---|
| 1 | Humira ® | 8 | 18 | 0 | 0 | 0 | 0 | 12 | 0.1 |
| 2 | Adalimumab biosimilar | 10 | 0 | 0 | 0 | 0 | 0 | 12 | 0.1 |
| 3 | Adalimumab biosimilar | 0 | 10 | 0 | 0 | 0 | 0 | 12 | 0.1 |
| 4 | Adalimumab biosimilar | 0 | 0 | 10 | 0 | 0 | 0 | 12 | 0.1 |
| 5 | Adalimumab biosimilar | 0 | 0 | 0 | 10 | 0 | 0 | 12 | 0.1 |
| 6 | Adalimumab biosimilar | 0 | 0 | 0 | 0 | 10 | 0 | 12 | 0.1 |
| 7 | Adalimumab biosimilar | 0 | 0 | 0 | 0 | 0 | 10 | 12 | 0.1 |

TABLE B-1

Percent monomer for Block B formulations at t0 and after two weeks at 40 C. (t2)

| Form No. | API | Buffer | Monomer (t0) | Monomer (t2) | Fragment (t0) | Fragment (t2) |
|---|---|---|---|---|---|---|
| 1 | Humira ® | Citrate/phosphate | 99.34 | | 0.26 | |
| 2 | Adalimumab biosimilar | citrate | 98.71 | 97.92 | 0.62 | 0.40 |
| 3 | Adalimumab biosimilar | phosphate | 99.21 | 98.07 | 0.05 | 0.30 |
| 4 | Adalimumab biosimilar | succinate | 99.19 | 98.04 | 0.04 | 0.31 |
| 5 | Adalimumab biosimilar | histidine | 99.19 | 98.41 | 0.07 | 0.23 |
| 6 | Adalimumab biosimilar | tartrate | 99.13 | 98.10 | 0.04 | 0.29 |
| 7 | Adalimumab biosimilar | maleate | 98.91 | 97.90 | 0.36 | 0.76 |

As can be seen from Table B-1 above, upon storage for two weeks at 40 C, the monomer content decreases by more than 1% for all of the samples in Block B, except for the one containing histidine (His) buffer (Table B-1). From this study we discovered the likelihood that His would be a superior buffer system for adalimumab. (We note that the fragment level measured by SEC reported for Formulation 2 appears to be incorrect as all of the other initial fragment s levels are less than 0.1%.)

Block C Formulation Studies

A large-scale formulation screening study was carried out in the studies conducted in Block C (See Table C, below). Samples were stored for one week at 40 C (hereinafter referenced as "t1") or two weeks at 25 C (hereinafter referenced as "t2"). These conditions were used throughout the remainder of our studies, so this terminology will be employed throughout the present detailed discussion. Block C was designed to expand on the buffer assessment conducted in Block B. In addition, it examined glycine (Gly) and/or arginine (Arg) as possible stabilizers in place of mannitol and/or NaCl (Table C). Note that the buffer system used in the Humira® product employs the 8 mM citrate/18 mM phosphate buffer, which is the composition of Formulation 1 of Block C. In this case, a proprietary adalimumab biosimilar protein was used for formulation 1 of Block C, instead of adalimumab protein obtained from commercially available Humira®.

TABLE C

BLOCK C STUDY DESIGN

| Form No. | API | citrate | phosphate | succinate | histidine | glycine | arginine | mannitol | NaCl |
|---|---|---|---|---|---|---|---|---|---|
| 1 | Adalimumab biosimilar | 8 | 18 | 0 | 0 | 0 | 0 | 65 | 100 |
| 2 | Adalimumab biosimilar | 18 | 8 | 0 | 0 | 0 | 0 | 65 | 100 |
| 3 | Adalimumab biosimilar | 20 | 0 | 0 | 0 | 0 | 0 | 65 | 100 |
| 4 | Adalimumab biosimilar | 20 | 0 | 0 | 0 | 65 | 0 | 0 | 100 |
| 5 | Adalimumab biosimilar | 0 | 20 | 0 | 0 | 65 | 0 | 0 | 100 |
| 6 | Adalimumab biosimilar | 20 | 0 | 0 | 0 | 0 | 65 | 0 | 100 |
| 7 | Adalimumab biosimilar | 0 | 20 | 0 | 0 | 0 | 65 | 0 | 100 |
| 8 | Adalimumab biosimilar | 0 | 0 | 20 | 0 | 65 | 0 | 0 | 100 |
| 9 | Adalimumab biosimilar | 0 | 0 | 20 | 0 | 0 | 65 | 0 | 100 |
| 10 | Adalimumab biosimilar | 0 | 0 | 0 | 20 | 65 | 0 | 0 | 100 |
| 11 | Adalimumab biosimilar | 0 | 0 | 0 | 20 | 0 | 65 | 0 | 100 |
| 12 | Adalimumab biosimilar | 0 | 20 | 0 | 0 | 0 | 130 | 0 | 35 |
| 13 | Adalimumab biosimilar | 0 | 0 | 20 | 0 | 0 | 130 | 0 | 35 |
| 14 | Adalimumab biosimilar | 0 | 0 | 0 | 20 | 0 | 130 | 0 | 35 |
| 15 | Adalimumab biosimilar | 0 | 20 | 0 | 0 | 130 | 0 | 0 | 60 |

TABLE C-continued

BLOCK C STUDY DESIGN

| Form No. | API | citrate | phosphate | succinate | histidine | glycine | arginine | mannitol | NaCl |
|---|---|---|---|---|---|---|---|---|---|
| 16 | Adalimumab biosimilar | 0 | 20 | 0 | 20 | 130 | 0 | 0 | 60 |

TABLE C-1

Measured pH for Block C formulations at t0 and t1 (one week, 40° C.)

| Form No. | citrate | phosphate | succinate | histidine | glycine | arginine | mannitol | NaCl | pH t0 | pH t2 |
|---|---|---|---|---|---|---|---|---|---|---|
| 1 | 8 | 18 | 0 | 0 | 0 | 0 | 65 | 100 | 5.51 | 5.57 |
| 2 | 18 | 8 | 0 | 0 | 0 | 0 | 65 | 100 | 5.46 | 5.43 |
| 3 | 20 | 0 | 0 | 0 | 0 | 0 | 65 | 100 | 5.28 | 5.27 |
| 4 | 20 | 0 | 0 | 0 | 65 | 0 | 0 | 100 | 5.27 | 5.24 |
| 5 | 0 | 20 | 0 | 0 | 65 | 0 | 0 | 100 | 5.43 | 5.44 |
| 6 | 20 | 0 | 0 | 0 | 0 | 65 | 0 | 100 | 5.29 | 5.29 |
| 7 | 0 | 20 | 0 | 0 | 0 | 65 | 0 | 100 | 5.28 | 5.32 |
| 8 | 0 | 0 | 20 | 0 | 65 | 0 | 0 | 100 | 5.22 | 5.17 |
| 9 | 0 | 0 | 20 | 0 | 0 | 65 | 0 | 100 | 5.19 | 5.16 |
| 10 | 0 | 0 | 0 | 20 | 65 | 0 | 0 | 100 | 5.28 | 5.30 |
| 11 | 0 | 0 | 0 | 20 | 0 | 65 | 0 | 100 | 5.26 | 5.29 |
| 12 | 0 | 20 | 0 | 0 | 0 | 130 | 0 | 35 | 5.24 | 5.24 |
| 13 | 0 | 0 | 20 | 0 | 0 | 130 | 0 | 35 | 5.18 | 5.16 |
| 14 | 0 | 0 | 0 | 20 | 0 | 130 | 0 | 35 | 5.28 | 5.35 |
| 15 | 0 | 20 | 0 | 0 | 130 | 0 | 0 | 60 | 5.31 | 5.31 |
| 16 | 0 | 20 | 0 | 20 | 130 | 0 | 0 | 60 | 5.36 | 5.40 |

TABLE C-2

Monomer content by SEC for formulations in Block C at t0, t1 (one week at 40° C.), and t2 (two weeks at 25° C.)

| Form No. | citrate | phosphate | succinate | His | Gly | Arg | mannitol | NaCl | t0 | t1 | t2 |
|---|---|---|---|---|---|---|---|---|---|---|---|
| 1 | 8 | 18 | 0 | 0 | 0 | 0 | 65 | 100 | 98.75 | 97.90 | 98.06 |
| 2 | 18 | 8 | 0 | 0 | 0 | 0 | 65 | 100 | 99.26 | 98.22 | 98.80 |
| 3 | 20 | 0 | 0 | 0 | 0 | 0 | 65 | 100 | 99.28 | 98.32 | 98.78 |
| 4 | 20 | 0 | 0 | 0 | 65 | 0 | 0 | 100 | 99.36 | 98.45 | 99.03 |
| 5 | 0 | 20 | 0 | 0 | 65 | 0 | 0 | 100 | 99.25 | 98.20 | 98.77 |
| 6 | 20 | 0 | 0 | 0 | 0 | 65 | 0 | 100 | 99.42 | 98.68 | 99.10 |
| 7 | 0 | 20 | 0 | 0 | 0 | 65 | 0 | 100 | 99.39 | 98.59 | 99.13 |
| 8 | 0 | 0 | 20 | 0 | 65 | 0 | 0 | 100 | 99.41 | 98.51 | 99.04 |
| 9 | 0 | 0 | 20 | 0 | 0 | 65 | 0 | 100 | 99.36 | 98.52 | 98.96 |
| 10 | 0 | 0 | 0 | 20 | 65 | 0 | 0 | 100 | 99.41 | 98.66 | 99.15 |
| 11 | 0 | 0 | 0 | 20 | 0 | 65 | 0 | 100 | 99.37 | 98.70 | 99.15 |
| 12 | 0 | 20 | 0 | 0 | 0 | 130 | 0 | 35 | 99.41 | 98.66 | 99.14 |
| 13 | 0 | 0 | 20 | 0 | 0 | 130 | 0 | 35 | 99.42 | 98.71 | 99.17 |
| 14 | 0 | 0 | 0 | 20 | 0 | 130 | 0 | 35 | 99.40 | 98.75 | 99.26 |
| 15 | 0 | 20 | 0 | 0 | 130 | 0 | 0 | 60 | 99.32 | 98.53 | 99.05 |
| 16 | 0 | 20 | 0 | 20 | 130 | 0 | 0 | 60 | 99.40 | 98.66 | 99.19 |

TABLE C-3

Percent purity by RP HPLC for formulations in Block C at t0, t1 (one week at 40° C.), and t2 (two weeks at 25° C.)

| Form No. | citrate | phosphate | succinate | His | Gly | Arg | mannitol | NaCl | t0 | t1 | t2 |
|---|---|---|---|---|---|---|---|---|---|---|---|
| 1 | 8 | 18 | 0 | 0 | 0 | 0 | 65 | 100 | 98.04 | 97.92 | 98.10 |
| 2 | 18 | 8 | 0 | 0 | 0 | 0 | 65 | 100 | 97.94 | 97.83 | 98.03 |
| 3 | 20 | 0 | 0 | 0 | 0 | 0 | 65 | 100 | 98.03 | 97.92 | 98.00 |

TABLE C-3-continued

Percent purity by RP HPLC for formulations in Block C at t0, t1 (one week at 40° C.), and t2 (two weeks at 25° C.)

| Form No. | citrate | phosphate | succinate | His | Gly | Arg | mannitol | NaCl | t0 | t1 | t2 |
|---|---|---|---|---|---|---|---|---|---|---|---|
| 4 | 20 | 0 | 0 | 0 | 65 | 0 | 0 | 100 | 97.94 | 97.75 | 97.98 |
| 5 | 0 | 20 | 0 | 0 | 65 | 0 | 0 | 100 | 97.98 | 97.69 | 97.95 |
| 6 | 20 | 0 | 0 | 0 | 0 | 65 | 0 | 100 | 97.89 | 97.72 | 97.92 |
| 7 | 0 | 20 | 0 | 0 | 0 | 65 | 0 | 100 | 97.80 | 97.70 | 97.91 |
| 8 | 0 | 0 | 20 | 0 | 65 | 0 | 0 | 100 | 97.98 | 97.77 | 98.01 |
| 9 | 0 | 0 | 20 | 0 | 0 | 65 | 0 | 100 | 97.98 | 97.73 | 97.94 |
| 10 | 0 | 0 | 0 | 20 | 65 | 0 | 0 | 100 | 97.98 | 97.76 | 98.00 |
| 11 | 0 | 0 | 0 | 20 | 0 | 65 | 0 | 100 | 97.87 | 97.78 | 97.97 |
| 12 | 0 | 20 | 0 | 0 | 0 | 0 | 130 | 35 | 97.88 | 97.71 | 97.95 |
| 13 | 0 | 0 | 20 | 0 | 0 | 0 | 130 | 35 | 97.95 | 97.62 | 97.93 |
| 14 | 0 | 0 | 0 | 20 | 0 | 0 | 130 | 35 | 97.98 | 97.72 | 98.04 |
| 15 | 0 | 20 | 0 | 0 | 130 | 0 | 0 | 60 | 97.91 | 97.72 | 97.96 |
| 16 | 0 | 20 | 0 | 20 | 130 | 0 | 0 | 60 | 98.00 | 97.79 | 97.78 |

TABLE C-4

Percentage of main bands seen in the cIEF profile of formulations in Block C at t0, t1 (one week at 40° C.), and t2 (two weeks at 25° C.)

| Form No. | pH | t0 | t1 | t2 |
|---|---|---|---|---|
| 1 | 8.59 | 1.94 | 1.97 | 1.82 |
|  | 8.43 | 11.76 | 11.30 | 12.49 |
|  | 8.27 | 58.29 | 49.88 | 51.54 |
|  | 8.20 |  | 7.18 | 7.59 |
|  | 8.05 | 21.49 | 22.38 | 19.79 |
|  | 7.86 | 6.53 | 5.35 | 4.66 |
| 2 | 8.60 | 1.96 |  | 1.84 |
|  | 8.44 | 12.08 |  | 10.89 |
|  | 8.29 | 51.70 |  | 47.63 |
|  | 8.22 | 9.74 |  | 12.32 |
|  | 8.09 | 16.29 |  | 18.25 |
|  | 7.91 | 3.50 |  | 3.64 |
| 3 | 8.60 | 1.83 | 1.82 | 1.12 |
|  | 8.43 | 11.58 | 9.67 | 10.40 |
|  | 8.27 | 45.80 | 32.99 | 44.04 |
|  | 8.20 | 12.44 | 22.27 | 18.68 |
|  | 8.01 | 17.57 | 16.21 | 14.40 |
|  | 7.86 | 4.39 |  | 3.61 |
| 4 | 8.57 | 2.31 | 2.04 | 2.13 |
|  | 8.41 | 12.94 | 11.51 | 12.62 |
|  | 8.25 | 33.37 | 59.98 | 61.97 |
|  | 8.20 | 23.03 |  |  |
|  | 8.02 | 15.21 | 18.33 | 16.07 |
|  | 7.88 | 3.45 | 5.32 | 3.70 |
| 5 | 8.58 | 2.40 | 2.00 | 2.30 |
|  | 8.41 | 13.01 | 11.02 | 12.34 |
|  | 8.25 | 42.09 | 46.32 | 37.30 |
|  | 8.21 | 15.58 | 10.65 | 15.80 |
|  | 8.03 | 18.48 | 20.58 | 16.80 |
|  | 7.86 | 3.74 | 6.13 | 4.83 |
| 6 | 8.57 |  |  | 2.83 |
|  | 8.38 | 13.17 |  | 13.23 |
|  | 8.23 | 32.66 |  | 31.18 |
|  | 8.18 | 17.52 |  | 18.54 |
|  | 8.02 | 17.48 |  | 13.82 |
|  | 7.91 | 5.30 |  | 5.83 |
| 7 | 8.58 | 2.08 | 2.41 | 2.64 |
|  | 8.44 | 13.42 | 12.64 | 12.63 |
|  | 8.27 | 56.79 | 52.48 | 54.76 |
|  | 8.16 | 5.36 | 6.16 | 6.38 |
|  | 8.04 | 16.91 | 20.09 | 18.45 |
|  | 7.94 | 5.44 | 4.12 | 5.15 |
| 8 | 8.57 | 1.76 | 2.37 | 1.55 |
|  | 8.44 | 14.41 | 12.13 | 11.61 |
|  | 8.29 | 60.01 | 48.87 | 52.94 |
|  | 8.19 |  | 7.07 | 10.66 |
|  | 8.10 | 16.22 | 16.55 | 17.10 |
|  | 7.95 | 7.61 | 5.02 | 4.55 |
| 9 | 8.58 | 2.19 | 2.06 | 0.99 |
|  | 8.41 | 11.69 | 10.64 | 12.73 |
|  | 8.26 | 50.07 | 44.21 | 60.33 |
|  | 8.19 | 10.66 | 10.39 |  |
|  | 8.01 | 15.62 | 21.51 | 17.79 |
|  | 7.87 | 4.67 | 5.37 | 8.16 |
| 10 | 8.57 | 1.78 | 2.64 | 1.62 |
|  | 8.41 | 10.55 | 10.95 | 8.11 |
|  | 8.25 | 43.82 | 42.93 | 36.11 |
|  | 8.21 | 15.96 | 15.24 | 17.66 |
|  | 8.02 | 14.63 | 14.58 | 14.22 |
|  | 7.88 | 3.82 | 4.21 | 3.95 |
| 11 | 8.58 | 1.59 | 1.81 | 1.89 |
|  | 8.41 | 12.98 | 11.58 | 12.86 |
|  | 8.23 | 62.74 | 29.63 | 12.00 |
|  | 8.19 |  | 22.86 | 34.77 |
|  | 8.02 | 17.15 | 19.52 | 17.06 |
|  | 7.87 | 5.54 | 5.56 | 4.77 |
| 12 | 8.61 | 0.35 | 1.57 | 1.47 |
|  | 8.35 | 13.24 | 13.41 | 8.83 |
|  | 8.19 | 43.18 | 60.12 | 26.52 |
|  | 8.15 | 15.43 | 20.46 | 25.60 |
|  | 7.98 | 16.74 |  | 17.38 |
|  | 7.88 | 4.96 | 4.44 | 4.99 |
| 13 | 8.58 | 1.71 |  | 1.67 |
|  | 8.41 | 11.63 |  | 10.01 |
|  | 8.26 | 49.19 |  | 42.65 |
|  | 8.20 | 14.25 |  | 16.64 |
|  | 8.03 | 17.35 |  | 18.12 |
|  | 7.86 | 4.28 |  | 4.18 |
| 14 | 8.56 | 1.64 | 1.79 | 1.73 |
|  | 8.39 | 13.17 | 10.45 | 10.96 |
|  | 8.25 | 58.68 | 46.06 | 45.60 |
|  | 8.21 |  | 11.03 | 13.34 |
|  | 8.07 | 14.10 | 20.24 | 14.50 |
|  | 7.92 | 2.10 | 5.13 | 4.28 |
| 15 | 8.57 | 1.74 | 1.22 | 1.60 |
|  | 8.41 | 10.49 | 15.21 | 10.78 |
|  | 8.25 | 46.06 | 55.05 | 44.98 |
|  | 8.20 | 14.46 |  | 13.79 |
|  | 8.02 | 13.90 | 20.31 | 10.79 |
|  | 7.89 | 4.23 | 4.90 | 3.43 |
| 16 | 8.56 | 1.96 | 1.08 |  |
|  | 8.40 | 9.25 | 12.23 | 12.58 |
|  | 8.24 | 38.08 | 31.03 | 58.61 |
|  | 8.20 | 19.02 | 22.08 | 21.50 |

TABLE C-4-continued

Percentage of main bands seen in the cIEF profile of formulations in Block C at t0, t1 (one week at 40° C.), and t2 (two weeks at 25° C.)

| Form No. | pH | t0 | t1 | t2 |
|---|---|---|---|---|
|  | 8.03 | 12.00 | 13.24 | 7.31 |
|  | 7.89 | 4.73 | 4.82 |  |

TABLE C-5

Percentage of bands for light chain (LC), heavy chain (HC), non-glycosylated HC, and other species for formulations in Block C at t0, t1 (one week at 40° C.), and t2 (two weeks at 25° C.)

| Form No. | Time | LC | HC | ngHC | Other |
|---|---|---|---|---|---|
| 1 | t0 | 35.87 | 63.20 | 0.51 | 0.42 |
|  | t1 | 29.71 | 63.08 | 0.37 | 6.84 |
|  | t2 | 31.01 | 67.83 | 0.54 | 0.61 |
| 2 | t0 | 29.50 | 69.57 | 0.56 | 0.37 |
|  | t1 | 30.51 | 67.28 | 0.56 | 1.65 |
|  | t2 | 32.32 | 65.51 | 0.56 | 1.61 |
| 3 | t0 | 32.53 | 66.45 | 0.54 | 0.47 |
|  | t1 | 33.04 | 65.34 | 0.55 | 1.07 |
|  | t2 | 31.94 | 66.60 | 0.57 | 0.90 |
| 4 | t0 | 33.40 | 64.90 | 0.46 | 1.24 |
|  | t1 | 30.96 | 67.16 | 0.52 | 1.36 |
|  | t2 | 32.08 | 65.84 | 0.56 | 1.52 |
| 5 | t0 | 34.17 | 63.89 | 0.49 | 1.45 |
|  | t1 | 33.60 | 64.27 | 0.56 | 1.57 |
|  | t2 | 32.15 | 66.20 | 0.48 | 1.17 |
| 6 | t0 | 37.91 | 60.35 | 0.54 | 1.19 |
|  | t1 | 34.80 | 62.88 | 0.73 | 1.59 |
|  | t2 | 32.90 | 65.62 | 0.50 | 0.99 |
| 7 | t0 | 32.17 | 66.80 | 0.55 | 0.49 |
|  | t1 | 29.83 | 68.33 | 0.59 | 1.25 |
|  | t2 | 33.32 | 65.97 | 0.55 | 0.15 |
| 8 | t0 | 33.83 | 65.51 | 0.49 | 0.17 |
|  | t1 | 30.37 | 68.48 | 0.58 | 0.57 |
|  | t2 | 32.86 | 66.40 | 0.55 | 0.19 |
| 9 | t0 | 30.69 | 69.31 | 0.00 | 0.00 |
|  | t1 | 34.30 | 64.24 | 0.52 | 0.94 |
|  | t2 | 29.08 | 69.87 | 0.62 | 0.43 |
| 10 | t0 | 38.68 | 59.95 | 0.57 | 0.80 |
|  | t1 | 36.52 | 58.65 | 0.00 | 4.83 |
|  | t2 | 43.68 | 54.39 | 1.92 | 0.00 |
| 11 | t0 | 35.25 | 59.00 | 1.75 | 4.00 |
|  | t1 | 30.71 | 67.58 | 0.66 | 1.05 |
|  | t2 | 30.18 | 67.14 | 0.47 | 2.21 |
| 13 | t0 | 44.58 | 55.42 | 0.00 | 0.00 |
|  | t1 | 37.73 | 60.75 | 0.25 | 1.28 |
|  | t2 | 38.05 | 61.44 | 0.52 | 0.00 |
| 14 | t0 | 32.50 | 66.66 | 0.60 | 0.24 |
|  | t1 | 30.91 | 67.77 | 0.61 | 0.70 |
|  | t2 | 29.14 | 70.32 | 0.23 | 0.31 |
| 15 | t0 | 30.07 | 68.95 | 0.63 | 0.35 |
|  | t1 | 30.14 | 68.49 | 0.62 | 0.75 |
|  | t2 | 31.57 | 67.55 | 0.62 | 0.26 |
| 16 | t0 | 30.54 | 68.61 | 0.63 | 0.22 |
|  | t1 | 29.81 | 68.81 | 0.63 | 0.75 |
|  | t2 | 29.46 | 69.14 | 0.59 | 0.81 |

Discussion of Block C Results

Referring to Table C-1 above, the pH was measured and found to be relatively stable for all of the formulations. However, the initial pH values were slightly higher for the citrate/phosphate formulations. The least stable formulation by SEC analysis appears to be Formulation 1, the one using the Humira® buffer system. By comparison we discovered that formulations using His as the buffer and/or formulations containing Gly or Arg exhibited the greatest stability (See Table C-2). Similar trends are seen when the purity by RP HPLC is considered (See Table C-3). It appears that SEC may be a better stability-indicating method than RP HPLC, although, when taken as a whole, the RP HPLC method does appear to be stability-indicating. Based on the Block C data summarized above, we have discovered that Histidine is suitable as a preferred buffer in terms of formulation stability, and that glycine or arginine, or combinations thereof, are also stability enhancing components for inclusion in an adalimumab formulation.

The stored samples were further analyzed by cIEF at t1 and t2 (Table C-4 above). A proprietary adalimumab material exhibit four to five peaks with integrated intensities above 1% or so. In general, there are some small decreases in the intensity of the main peak upon storage. These losses are usually greater at t1 than at t2. Still, no significant new peaks are observed, suggesting that there is minimal chemical degradation occurring that would lead to changes in the overall charge on the protein. The variance in the data indicates that this method, while useful for characterization, does not appear to be stability-indicating.

The final analytical method used to evaluate the stability of adalimumab formulation is CE-SDS, which is essentially the CE version of SDS-PAGE slab gels. This method indicates that the relative areas of the LC peak do decrease when stored at elevated temperatures (Table C-5), while the amount of new peaks (cumulatively called 'Other') increases. Altogether, these changes are usually less than 2% for any of the formulations. There are some samples where the percentage of 'Other' is in the 4-6% range, but these are likely artifacts.

Block D Formulation Studies

Another set of formulations were evaluated as "Block D." Sixteen formulations were designed to evaluate other stabilizers as alternatives to mannitol, such as sorbitol and trehalose (See Table D). Block D also examined using mannitol or NaCl as the sole tonicity agent, instead of using a mixture of the two excipients. The pH stability of the formulations was quite good, although the actual initial pH values were slightly lower than the target values for some formulations (Table D-1).

TABLE D

BLOCK D STUDY DESIGN

| Form No. | API | citrate | phosphate | sorbitol | trehalose | mannitol | NaCl | PS 80 |
|---|---|---|---|---|---|---|---|---|
| 1 | Adalimumab biosimilar | 8 | 18 | 0 | 0 | 65 | 100 | 0.1 |

TABLE D-continued

BLOCK D STUDY DESIGN

| Form No. | API | citrate | phosphate | sorbitol | trehalose | mannitol | NaCl | PS 80 |
|---|---|---|---|---|---|---|---|---|
| 2 | Adalimumab biosimilar | 8 | 18 | 0 | 0 | 65 | 100 | 0 |
| 3 | Adalimumab biosimilar | 20 | 0 | 0 | 0 | 65 | 100 | 0.1 |
| 4 | Adalimumab biosimilar | 20 | 0 | 0 | 0 | 65 | 100 | 0 |
| 5 | Adalimumab biosimilar | 0 | 20 | 0 | 0 | 65 | 100 | 0.1 |
| 6 | Adalimumab biosimilar | 0 | 20 | 0 | 0 | 65 | 100 | 0 |
| 7 | Adalimumab biosimilar | 8 | 18 | 65 | 0 | 0 | 100 | 0.1 |
| 8 | Adalimumab biosimilar | 8 | 18 | 0 | 65 | 0 | 100 | 0.1 |
| 9 | Adalimumab biosimilar | 0 | 20 | 65 | 0 | 0 | 100 | 0.1 |
| 10 | Adalimumab biosimilar | 0 | 10 | 0 | 0 | 240 | 0 | 0.1 |
| 11 | Adalimumab biosimilar | 0 | 10 | 240 | 0 | 0 | 0 | 0.1 |
| 12 | Adalimumab biosimilar | 0 | 10 | 0 | 240 | 0 | 0 | 0.1 |
| 13 | Adalimumab biosimilar | 10 | 0 | 0 | 0 | 0 | 150 | 0.1 |
| 14 | Adalimumab biosimilar | 10 | 0 | 0 | 0 | 0 | 150 | 0 |
| 15 | Adalimumab biosimilar | 0 | 10 | 0 | 0 | 0 | 150 | 0.1 |
| 16 | Adalimumab biosimilar | 0 | 10 | 0 | 0 | 0 | 150 | 0 |

TABLE D-1

Measured pH for Block D formulations at t0 and t1 (one week, 40° C.)

| Form No. | API | citrate | phosphate | sorbitol | trehalose | mannitol | NaCl | PS 80 | t0 | t1 | t2 |
|---|---|---|---|---|---|---|---|---|---|---|---|
| 1 | Adalimumab biosimilar | 8 | 18 | 0 | 0 | 65 | 100 | 0.1 | 5.09 | 5.17 | 5.12 |
| 2 | Adalimumab biosimilar | 8 | 18 | 0 | 0 | 65 | 100 | 0 | 5.12 | 5.16 | 5.16 |
| 3 | Adalimumab biosimilar | 20 | 0 | 0 | 0 | 65 | 100 | 0.1 | 5.11 | 5.16 | 5.14 |
| 4 | Adalimumab biosimilar | 20 | 0 | 0 | 0 | 65 | 100 | 0 | 5.13 | 5.17 | 5.18 |
| 5 | Adalimumab biosimilar | 0 | 20 | 0 | 0 | 65 | 100 | 0.1 | 5.19 | 5.25 | 5.24 |
| 6 | Adalimumab biosimilar | 0 | 20 | 0 | 0 | 65 | 100 | 0 | 5.16 | 5.24 | 5.17 |
| 7 | Adalimumab biosimilar | 8 | 18 | 65 | 0 | 0 | 100 | 0.1 | 5.14 | 5.17 | 5.18 |
| 8 | Adalimumab biosimilar | 8 | 18 | 0 | 65 | 0 | 100 | 0.1 | 5.15 | 5.21 | 5.16 |
| 9 | Adalimumab biosimilar | 0 | 20 | 65 | 0 | 0 | 100 | 0.1 | 5.19 | 5.29 | 5.28 |
| 10 | Adalimumab biosimilar | 0 | 10 | 0 | 0 | 240 | 0 | 0.1 | 5.23 | 5.28 | 5.27 |
| 11 | Adalimumab biosimilar | 0 | 10 | 240 | 0 | 0 | 0 | 0.1 | 5.45 | 5.35 | 5.33 |
| 12 | Adalimumab biosimilar | 0 | 10 | 0 | 240 | 0 | 0 | 0.1 | 5.44 | 5.32 | 5.31 |
| 13 | Adalimumab biosimilar | 10 | 0 | 0 | 0 | 0 | 150 | 0.1 | 5.30 | 5.25 | 5.23 |
| 14 | Adalimumab biosimilar | 10 | 0 | 0 | 0 | 0 | 150 | 0 | 5.39 | 5.20 | 5.18 |
| 15 | Adalimumab biosimilar | 0 | 10 | 0 | 0 | 0 | 150 | 0.1 | 5.35 | 5.30 | 5.22 |
| 16 | Adalimumab biosimilar | 0 | 10 | 0 | 0 | 0 | 150 | 0 | 5.41 | 5.33 | 5.28 |

TABLE D-2

Monomer content by SEC for formulations in Block D at t0, t1 (one week at 40° C.), and t2 (two weeks at 25° C.)

| Form No. | API | citrate | phosphate | sorbitol | trehalose | mannitol | NaCl | PS 80 | t0 | t1 | t2 |
|---|---|---|---|---|---|---|---|---|---|---|---|
| 1 | Adalimumab biosimilar | 8 | 18 | 0 | 0 | 65 | 100 | 0.1 | 99.28 | 98.21 | 98.96 |
| 2 | Adalimumab biosimilar | 8 | 18 | 0 | 0 | 65 | 100 | 0 | 99.25 | 98.11 | 98.85 |
| 3 | Adalimumab biosimilar | 20 | 0 | 0 | 0 | 65 | 100 | 0.1 | 99.25 | 98.16 | 98.86 |
| 4 | Adalimumab biosimilar | 20 | 0 | 0 | 0 | 65 | 100 | 0 | 99.27 | 98.26 | 98.92 |
| 5 | Adalimumab biosimilar | 0 | 20 | 0 | 0 | 65 | 100 | 0.1 | 99.24 | 98.16 | 98.84 |
| 6 | Adalimumab biosimilar | 0 | 20 | 0 | 0 | 65 | 100 | 0 | 99.21 | 98.23 | 98.82 |
| 7 | Adalimumab biosimilar | 8 | 18 | 65 | 0 | 0 | 100 | 0.1 | 99.30 | 98.19 | 98.94 |
| 8 | Adalimumab biosimilar | 8 | 18 | 0 | 65 | 0 | 100 | 0.1 | 99.28 | 98.14 | 98.85 |
| 9 | Adalimumab biosimilar | 0 | 20 | 65 | 0 | 0 | 100 | 0.1 | 99.29 | 98.23 | 98.90 |
| 10 | Adalimumab biosimilar | 0 | 10 | 0 | 0 | 240 | 0 | 0.1 |  | 97.93 | 98.54 |
| 11 | Adalimumab biosimilar | 0 | 10 | 240 | 0 | 0 | 0 | 0.1 | 99.32 | 98.65 | 99.00 |
| 12 | Adalimumab biosimilar | 0 | 10 | 0 | 240 | 0 | 0 | 0.1 | 99.32 | 98.53 | 98.96 |
| 13 | Adalimumab biosimilar | 10 | 0 | 0 | 0 | 0 | 150 | 0.1 | 99.29 | 98.12 | 98.84 |
| 14 | Adalimumab biosimilar | 10 | 0 | 0 | 0 | 0 | 150 | 0 | 99.28 | 98.28 | 98.90 |
| 15 | Adalimumab biosimilar | 0 | 10 | 0 | 0 | 0 | 150 | 0.1 | 99.26 | 97.99 | 98.83 |
| 16 | Adalimumab biosimilar | 0 | 10 | 0 | 0 | 0 | 150 | 0 | 99.20 | 97.76 | 98.62 |

TABLE D-3

Percent purity by RP HPLC for formulations in Block D at t0, t1 (one week at 40° C.), and t2 (two weeks at 25° C.)

| Form No. | API | citrate | phosphate | sorbitol | trehalose | mannitol | NaCl | PS 80 | t0 | t1 | t2 |
|---|---|---|---|---|---|---|---|---|---|---|---|
| 1 | Adalimumab biosimilar | 8 | 18 | 0 | 0 | 65 | 100 | 0.1 | 98.17 | 97.75 | 98.02 |
| 2 | Adalimumab biosimilar | 8 | 18 | 0 | 0 | 65 | 100 | 0 | 98.09 | 97.84 | 98.08 |
| 3 | Adalimumab biosimilar | 20 | 0 | 0 | 0 | 65 | 100 | 0.1 | 98.03 | 97.81 | 98.19 |
| 4 | Adalimumab biosimilar | 20 | 0 | 0 | 0 | 65 | 100 | 0 | 98.17 | 97.85 | 98.06 |
| 5 | Adalimumab biosimilar | 0 | 20 | 0 | 0 | 65 | 100 | 0.1 | 98.11 | 97.88 | 98.18 |
| 6 | Adalimumab biosimilar | 0 | 20 | 0 | 0 | 65 | 100 | 0 | 98.21 | 97.77 | 98.10 |
| 7 | Adalimumab biosimilar | 8 | 18 | 65 | 0 | 0 | 100 | 0.1 | 98.11 | 97.80 | 98.14 |
| 8 | Adalimumab biosimilar | 8 | 18 | 0 | 65 | 0 | 100 | 0.1 | 98.06 | 97.73 | 98.03 |
| 9 | Adalimumab biosimilar | 0 | 20 | 65 | 0 | 0 | 100 | 0.1 | 98.09 | 97.80 | 98.07 |
| 10 | Adalimumab biosimilar | 0 | 10 | 0 | 0 | 240 | 0 | 0.1 | 98.13 | 97.82 | 98.08 |
| 11 | Adalimumab biosimilar | 0 | 10 | 240 | 0 | 0 | 0 | 0.1 | 98.10 | 97.90 | 98.06 |
| 12 | Adalimumab biosimilar | 0 | 10 | 0 | 240 | 0 | 0 | 0.1 | 98.13 | 97.95 | 98.14 |
| 13 | Adalimumab biosimilar | 10 | 0 | 0 | 0 | 0 | 150 | 0.1 | 98.07 | 97.79 | 98.02 |
| 14 | Adalimumab biosimilar | 10 | 0 | 0 | 0 | 0 | 150 | 0 | 98.13 | 97.78 | 98.14 |

TABLE D-3-continued

Percent purity by RP HPLC for formulations in Block D at t0, t1 (one week at 40° C.), and t2 (two weeks at 25° C.)

| Form No. | API | citrate | phosphate | sorbitol | trehalose | mannitol | NaCl | PS 80 | t0 | t1 | t2 |
|---|---|---|---|---|---|---|---|---|---|---|---|
| 15 | Adalimumab biosimilar | 0 | 10 | 0 | 0 | 0 | 150 | 0.1 | 98.17 | 97.80 | 98.10 |
| 16 | Adalimumab biosimilar | 0 | 10 | 0 | 0 | 0 | 150 | 0 | 98.14 | 97.79 | 98.06 |

TABLE D-4

Percentage of main bands seen in the cIEF profile of formulations in Block D at t0, t1 (one week at 40° C.), and t2 (two weeks at 25° C.)

| Form No. | pH | t0 | t1 | t2 |
|---|---|---|---|---|
| 1 | 8.56 | 2.26 |  | 1.81 |
|  | 8.41 | 13.84 | 12.88 | 11.73 |
|  | 8.25 | 62.27 | 59.80 | 56.15 |
|  | 8.14 |  |  | 6.48 |
|  | 8.04 | 15.71 | 22.93 | 13.73 |
|  | 7.99 | 5.92 | 4.39 | 4.13 |
| 2 | 8.55 | 2.08 |  | 1.58 |
|  | 8.40 | 12.89 |  | 12.58 |
|  | 8.24 | 60.15 |  | 53.24 |
|  | 8.14 | 5.98 |  | 6.69 |
|  | 8.03 | 11.92 |  | 9.72 |
|  | 7.98 | 3.65 |  | 5.67 |
| 3 | 8.57 | 1.58 | 2.10 | 1.89 |
|  | 8.41 | 11.87 | 11.83 | 11.99 |
|  | 8.26 | 54.93 | 54.45 | 54.51 |
|  | 8.16 | 9.10 | 6.31 | 8.24 |
|  | 8.05 | 9.21 | 11.16 | 10.22 |
|  | 7.91 | 7.60 | 4.16 | 5.26 |
| 4 | 8.57 | 3.57 | 1.82 | 1.05 |
|  | 8.40 | 11.12 | 10.66 | 10.83 |
|  | 8.24 | 49.37 | 47.85 | 42.34 |
|  | 8.14 | 3.01 | 1.83 | 3.68 |
|  | 8.03 | 10.11 | 10.06 | 17.12 |
|  | 7.90 | 2.78 | 4.72 | 3.84 |
| 5 | 8.55 | 2.30 | 2.18 | 2.13 |
|  | 8.40 | 7.63 | 8.86 | 8.63 |
|  | 8.25 | 33.90 | 14.41 | 16.64 |
|  | 8.20 | 23.41 | 33.90 | 33.75 |
|  | 8.03 | 10.14 | 20.39 | 19.42 |
|  | 7.99 | 6.76 | 5.42 | 4.63 |
| 6 | 8.59 | 1.87 |  | 1.39 |
|  | 8.42 | 11.25 | 11.18 | 11.89 |
|  | 8.27 | 50.07 | 61.72 | 64.17 |
|  | 8.20 | 12.43 | 22.08 | 19.18 |
|  | 8.03 | 10.20 |  |  |
|  | 7.91 | 2.70 | 5.01 | 3.38 |
| 7 | 8.55 |  |  |  |
|  | 8.40 |  |  |  |
|  | 8.25 |  |  |  |
|  | 8.20 |  |  |  |
|  | 8.03 |  |  |  |
|  | 7.99 |  |  |  |
| 8 | 8.59 | 1.46 | 2.64 | 1.16 |
|  | 8.39 | 13.52 | 13.62 | 7.37 |
|  | 8.22 | 60.79 | 50.83 | 55.40 |
|  | 8.08 | 5.21 | 11.28 | 9.78 |
|  | 8.02 | 15.24 | 8.55 | 11.94 |
|  | 7.91 | 3.79 | 3.02 | 5.18 |
| 9 | 8.53 | 2.64 | 3.25 | 1.94 |
|  | 8.38 | 13.83 | 12.72 | 11.67 |
|  | 8.25 | 64.97 | 51.32 | 54.14 |
|  | 8.17 | 8.33 | 11.21 | 8.61 |
|  | 8.06 | 11.75 | 9.98 | 9.03 |
|  | 8.01 | 5.79 | 4.80 | 7.31 |
| 10 | 8.54 | 1.78 | 3.26 |  |
|  | 8.38 | 13.04 | 11.19 |  |
|  | 8.21 | 60.53 | 44.83 |  |
|  | 8.15 | 19.60 | 10.95 |  |
|  | 7.99 |  | 9.41 |  |
|  | 7.90 | 5.05 | 4.27 |  |
| 11 | 8.52 | 1.95 | 2.11 | 1.89 |
|  | 8.36 | 11.24 | 12.43 | 12.43 |
|  | 8.21 | 48.64 | 54.10 | 59.90 |
|  | 8.13 | 11.69 |  | 6.31 |
|  | 8.00 | 10.30 | 21.14 | 11.14 |
|  | 8.01 | 5.27 | 5.64 | 8.32 |
| 12 | 8.51 | 1.85 |  |  |
|  | 8.29 | 11.31 | 11.38 |  |
|  | 8.18 | 63.11 | 45.14 |  |
|  | 8.14 | 2.54 |  |  |
|  | 8.05 | 16.16 | 22.03 |  |
|  | 7.94 | 5.03 | 6.88 |  |
| 13 | 8.62 | 3.51 |  | 3.05 |
|  | 8.44 | 12.44 |  | 12.30 |
|  | 8.29 | 65.10 |  | 51.44 |
|  | 8.21 |  |  | 12.18 |
|  | 8.06 | 15.37 |  | 17.25 |
|  | 7.91 | 3.58 |  | 3.77 |
| 14 | 8.61 |  | 2.74 | 1.73 |
|  | 8.43 |  | 10.60 | 12.19 |
|  | 8.27 |  | 46.23 | 41.11 |
|  | 8.21 |  | 13.97 | 10.49 |
|  | 8.05 |  | 18.56 | 17.52 |
|  | 7.91 |  | 5.15 |  |
| 15 | 8.62 |  |  |  |
|  | 8.35 | 12.40 | 10.91 | 8.34 |
|  | 8.21 | 31.87 | 30.32 | 36.39 |
|  | 8.20 | 41.14 | 25.57 | 30.62 |
|  | 8.02 | 12.42 | 13.72 | 18.26 |
|  | 7.89 | 2.18 | 5.44 | 3.86 |
| 16 | 8.61 |  |  |  |
|  | 8.48 | 12.96 | 12.86 | 13.19 |
|  | 8.34 | 34.40 | 31.45 | 39.25 |
|  | 8.31 | 27.74 | 20.29 | 18.81 |
|  | 8.05 |  | 22.76 | 19.35 |
|  | 7.89 | 8.17 | 7.69 | 4.83 |

TABLE D-5

Percentage of bands for light chain (LC), heavy chain (HC), non-glycosylated HC, and other species for formulations in Block D at t0, t1 (one week at 40° C.), and t2 (two weeks at 25° C.)

| Form No. | Time | LC | HC | ngHC | Other |
|---|---|---|---|---|---|
| 1 | t0 |  |  |  |  |
|  | t1 | 34.11 | 62.58 | 0.58 | 2.73 |
|  | t2 | 33.19 | 64.28 | 0.60 | 1.92 |
| 2 | t0 | 30.25 | 66.81 | 0.64 | 2.31 |
|  | t1 | 30.61 | 65.79 | 0.54 | 3.07 |
|  | t2 | 29.22 | 67.04 | 0.64 | 3.10 |

TABLE D-5-continued

Percentage of bands for light chain (LC), heavy chain (HC), non-glycosylated HC, and other species for formulations in Block D at t0, t1 (one week at 40° C.), and t2 (two weeks at 25° C.)

| Form No. | Time | LC | HC | ngHC | Other |
|---|---|---|---|---|---|
| 3 | t0 | 27.48 | 68.51 | 0.59 | 3.42 |
|  | t1 | 30.84 | 67.27 | 0.54 | 1.35 |
|  | t2 | 30.30 | 68.13 | 0.58 | 0.99 |
| 4 | t0 | 30.88 | 68.33 | 0.60 | 0.19 |
|  | t1 | 29.76 | 68.32 | 0.57 | 1.34 |
|  | t2 | 31.49 | 66.95 | 0.55 | 1.01 |
| 5 | t0 | 33.77 | 64.50 | 0.56 | 1.17 |
|  | t1 | 31.59 | 66.54 | 0.52 | 1.34 |
|  | t2 | 29.19 | 69.16 | 0.59 | 1.06 |
| 6 | t0 | 30.90 | 68.08 | 0.56 | 0.47 |
|  | t1 | 29.32 | 69.88 | 0.54 | 0.26 |
|  | t2 | 31.08 | 67.58 | 0.54 | 0.79 |
| 7 | t0 | 30.41 | 68.60 | 0.56 | 0.43 |
|  | t1 | 30.87 | 66.95 | 0.55 | 1.63 |
|  | t2 | 30.14 | 68.28 | 0.55 | 1.03 |
| 8 | t0 | 31.68 | 67.41 | 0.60 | 0.31 |
|  | t1 |  |  |  |  |
|  | t2 |  |  |  |  |
| 9 | t0 | 29.62 | 68.12 | 0.51 | 1.75 |
|  | t1 |  |  |  |  |
|  | t2 | 29.46 | 68.10 | 0.61 | 1.83 |
| 10 | t0 | 29.80 | 67.99 | 0.58 | 1.64 |
|  | t1 | 30.04 | 65.53 | 0.45 | 3.98 |
|  | t2 | 30.41 | 66.27 | 0.53 | 2.80 |
| 11 | t0 | 29.85 | 67.63 | 0.61 | 1.91 |
|  | t1 | 29.02 | 68.18 | 0.60 | 2.20 |
|  | t2 | 30.44 | 67.14 | 0.58 | 1.84 |
| 12 | t0 | 29.38 | 68.11 | 0.55 | 1.96 |
|  | t1 | 30.16 | 65.55 | 0.49 | 3.80 |
|  | t2 | 28.20 | 69.19 | 0.59 | 2.02 |
| 13 | t0 | 31.38 | 66.28 | 0.55 | 1.79 |
|  | t1 | 33.67 | 64.10 | 0.56 | 1.67 |
|  | t2 | 29.72 | 67.99 | 0.58 | 1.71 |
| 14 | t0 | 37.34 | 60.53 | 0.52 | 1.62 |
|  | t1 | 33.03 | 63.46 | 0.53 | 2.97 |
|  | t2 | 34.39 | 63.62 | 0.54 | 1.45 |
| 15 | t0 | 30.20 | 68.42 | 0.59 | 0.79 |
|  | t1 | 28.67 | 69.42 | 0.58 | 1.33 |
|  | t2 | 29.96 | 68.24 | 0.56 | 1.24 |
| 16 | t0 | 31.62 | 66.95 | 0.58 | 0.85 |
|  | t1 | 30.48 | 66.36 | 0.55 | 2.61 |
|  | t2 | 27.94 | 70.17 | 0.60 | 1.29 |

Results of Block D

The pH stability was quite good for these formulations (Table D-1). Once again, the commercial adalimumab (Humira®) formulation was used as a control (but using a proprietary adalimumab biosimilar protein as the API). The commercial formulation again showed poorer stability by SEC than those using single buffers like phosphate and His (See Table D-2). Of the two buffers used in Humira®, we have now discovered that phosphate is the better stabilizer. This is surprising, as phosphate has virtually no buffer capacity at pH 5.2, while citrate buffers well at this pH. This suggests that the differences in stability profile may be due to direct interaction of the buffer with the protein, a phenomenon that, in the case of the commercial Humira® formulation, we believe was not previously understood or appreciated. Accordingly, the comparative benefit of selecting phosphate as a buffer in an adalimumab formulation, due to superior stability in the formulation versus the selection of a citrate/phosphate combination constitutes one of the important aspects of our invention.

Both sorbitol and trehalose display better stability profiles than mannitol when used as the sole tonicity agent in these formulations. It also appears that removal of the polysorbate 80 (PS 80) decreases stability somewhat. The best stability profile by SEC appears to be for Formulations 10 and 11, which contain high concentrations of sorbitol or trehalose in place of mannitol/NaCl (Table D-2). These results indicate to us that removing NaCl from the formulation, or limiting its concentration below certain targeted levels (for example less than about 100 mM), will be beneficial for stability. (We note that mannitol does appear to be a stabilizing ingredient, but at levels preferably above 150.)

The RP data indicates that either citrate or phosphate provides better stability than the combination used in Humira® (Table D-3). Again, the avoidance of the citrate/phosphate combination represents an important feature of our invention. It could not have been known or predicted that citrate alone, or phosphate alone would provide better formulation stability than the commercial buffer system comprising a combination of citrate and phosphate.

The cIEF analyses were run for Block D samples (Table D-4 above). As before, there is some decrease in the intensity of the main peak, but no new peaks are observed. In some cases, there is some small increase in the intensity of the more acidic peaks. The decreases in the main peak appear to be greater at t1 than at t2, suggesting that degradation at 5° C. would be almost imperceptible. Still, overall it looks like less than 5% (and probably much less than 5%) is degrading as measured by cIEF (Table D-4). Likewise, little degradation is seen by CE-SDS (Table D-5). At most 2 to 4% degradation is seen, but the variability in the method makes it difficult to determine if these are real changes. There does appear to be higher impurity levels (Other) for Formulations 1 and 2 and 10 through 14.

Block E Formulation Studies

This block of formulations was designed to evaluate the stability of formulations at different pH levels. If a buffer is not specified, acetate buffer (10 mM) was employed (Table E). A secondary objective was to evaluate Gly and Arg at higher concentrations and in combination as alternative stabilizers to mannitol and NaCl.

TABLE E

BLOCK E STUDY DESIGN

| Form No. | API | pH | citrate | phosphate | sorbitol | Gly | Arg | mannitol | NaCl | PS 80 |
|---|---|---|---|---|---|---|---|---|---|---|
| 1 | Adalimumab biosimilar | 5.2 | 8 | 18 | 0 | 0 | 0 | 65 | 100 | 0.1 |
| 2 | Adalimumab biosimilar | 3.5 | 8 | 18 | 0 | 0 | 0 | 65 | 100 | 0.1 |
| 3 | Adalimumab biosimilar | 5.2 | 0 | 0 | 0 | 0 | 0 | 65 | 100 | 0.1 |
| 4 | Adalimumab biosimilar | 3.5 | 0 | 0 | 0 | 0 | 0 | 65 | 100 | 0.1 |

TABLE E-continued

BLOCK E STUDY DESIGN

| Form No. | API | pH | citrate | phosphate | sorbitol | Gly | Arg | mannitol | NaCl | PS 80 |
|---|---|---|---|---|---|---|---|---|---|---|
| 5 | Adalimumab biosimilar | 3.5 | 0 | 0 | 65 | 0 | 0 | 0 | 100 | 0.1 |
| 6 | Adalimumab biosimilar | 3.5 | 0 | 0 | 0 | 0 | 130 | 0 | 0 | 0.1 |
| 7 | Adalimumab biosimilar | 3.5 | 0 | 0 | 0 | 0 | 130 | 0 | 0 | 0 |
| 8 | Adalimumab biosimilar | 3.5 | 0 | 0 | 0 | 240 | 0 | 0 | 0 | 0 |
| 9 | Adalimumab biosimilar | 5.2 | 0 | 0 | 0 | 240 | 0 | 0 | 0 | 0 |
| 10 | Adalimumab biosimilar | 3.5 | 0 | 0 | 0 | 100 | 100 | 0 | 0 | 0 |
| 11 | Adalimumab biosimilar | 5.2 | 0 | 0 | 0 | 100 | 100 | 0 | 0 | 0 |
| 12 | Adalimumab biosimilar | 3.5 | 0 | 0 | 0 | 150 | 50 | 0 | 0 | 0 |

TABLE E-1

Measured pH for Block E formulations at t0 and t1 (one week, 40° C.)

| Form No. | pH | citrate | phosphate | sorbitol | Gly | Arg | mannitol | NaCl | PS 80 | t0 | t1 | t2 |
|---|---|---|---|---|---|---|---|---|---|---|---|---|
| 1 | 5.2 | 8 | 18 | 0 | 0 | 0 | 65 | 100 | 0.1 | 5.15 | 5.11 | 5.21 |
| 2 | 3.5 | 8 | 18 | 0 | 0 | 0 | 65 | 100 | 0.1 | 3.36 | 3.49 | 3.50 |
| 3 | 5.2 | 0 | 0 | 0 | 0 | 0 | 65 | 100 | 0.1 | 5.13 | 5.24 | 5.24 |
| 4 | 3.5 | 0 | 0 | 0 | 0 | 0 | 65 | 100 | 0.1 | 3.31 | 3.43 | 3.45 |
| 5 | 3.5 | 0 | 0 | 65 | 0 | 0 | 0 | 100 | 0.1 | 3.30 | 3.48 | 3.42 |
| 6 | 3.5 | 0 | 0 | 0 | 0 | 130 | 0 | 0 | 0.1 | 3.24 | 3.52 | 3.42 |
| 7 | 3.5 | 0 | 0 | 0 | 0 | 130 | 0 | 0 | 0 | 3.27 | 3.59 | 3.48 |
| 8 | 3.5 | 0 | 0 | 0 | 240 | 0 | 0 | 0 | 0 | 3.27 | 3.33 | 3.39 |
| 9 | 5.2 | 0 | 0 | 0 | 240 | 0 | 0 | 0 | 0 | 5.05 | 5.25 | 5.20 |
| 10 | 3.5 | 0 | 0 | 0 | 100 | 100 | 0 | 0 | 0 | 3.30 | 3.45 | 3.41 |
| 11 | 5.2 | 0 | 0 | 0 | 100 | 100 | 0 | 0 | 0 | 5.20 | 5.38 | 5.39 |
| 12 | 3.5 | 0 | 0 | 0 | 150 | 50 | 0 | 0 | 0 | 3.24 | 3.38 | 3.37 |

TABLE E-2

Monomer content by SEC for formulations in Block E at t0, t1 (one week at 40° C.), and t2 (two weeks at 25° C.)

| Form No. | pH | citrate | phosphate | sorbitol | Gly | Arg | mannitol | NaCl | PS 80 | t0 | t1 | t2 |
|---|---|---|---|---|---|---|---|---|---|---|---|---|
| 1 | 5.2 | 8 | 18 | 0 | 0 | 0 | 65 | 100 | 0.1 | 99.23 | 98.20 | 98.85 |
| 2 | 3.5 | 8 | 18 | 0 | 0 | 0 | 65 | 100 | 0.1 | 98.82 | 44.15 | 86.37 |
| 3 | 5.2 | 0 | 0 | 0 | 0 | 0 | 65 | 100 | 0.1 | 99.30 | 98.37 | 99.02 |
| 4 | 3.5 | 0 | 0 | 0 | 0 | 0 | 65 | 100 | 0.1 | 95.85 | 33.51 | 76.21 |
| 5 | 3.5 | 0 | 0 | 65 | 0 | 0 | 0 | 100 | 0.1 | 97.37 | 26.21 | 77.80 |
| 6 | 3.5 | 0 | 0 | 0 | 0 | 130 | 0 | 0 | 0.1 | 97.79 | 35.67 | 65.83 |
| 7 | 3.5 | 0 | 0 | 0 | 0 | 130 | 0 | 0 | 0 | 99.00 | 55.51 | 90.60 |
| 8 | 3.5 | 0 | 0 | 0 | 240 | 0 | 0 | 0 | 0 | 99.24 | 75.60 | 98.24 |
| 9 | 5.2 | 0 | 0 | 0 | 240 | 0 | 0 | 0 | 0 | 99.08 | 98.63 | 99.18 |
| 10 | 3.5 | 0 | 0 | 0 | 100 | 100 | 0 | 0 | 0 | 99.28 | 51.03 | 91.66 |
| 11 | 5.2 | 0 | 0 | 0 | 100 | 100 | 0 | 0 | 0 | 99.32 | 98.54 | 99.09 |
| 12 | 3.5 | 0 | 0 | 0 | 150 | 50 | 0 | 0 | 0 | 99.29 | 45.86 | 93.06 |

TABLE E-3

Percent purity by RP HPLC for formulations in Block E at t0, t1 (one week at 40° C.), and t2 (two weeks at 25° C.)

| Form No. | pH | citrate | phosphate | sorbitol | Gly | Arg | mannitol | NaCl | PS 80 | t0 | t1 | t2 |
|---|---|---|---|---|---|---|---|---|---|---|---|---|
| 1 | 5.2 | 8 | 18 | 0 | 0 | 0 | 65 | 100 | 0.1 | 98.58 | 96.88 | 96.91 |
| 2 | 3.5 | 8 | 18 | 0 | 0 | 0 | 65 | 100 | 0.1 | 98.51 | 90.29 | 95.99 |

TABLE E-3-continued

Percent purity by RP HPLC for formulations in Block E at t0, t1 (one week at 40° C.), and t2 (two weeks at 25° C.)

| Form No. | pH | citrate | phosphate | sorbitol | Gly | Arg | mannitol | NaCl | PS 80 | t0 | t1 | t2 |
|---|---|---|---|---|---|---|---|---|---|---|---|---|
| 3 | 5.2 | 0 | 0 | 0 | 0 | 0 | 65 | 100 | 0.1 | 98.50 | 96.90 | 96.83 |
| 4 | 3.5 | 0 | 0 | 0 | 0 | 0 | 65 | 100 | 0.1 | 98.56 | 91.18 | 95.55 |
| 5 | 3.5 | 0 | 0 | 65 | 0 | 0 | 0 | 100 | 0.1 | 98.45 | 90.96 | 95.71 |
| 6 | 3.5 | 0 | 0 | 0 | 0 | 130 | 0 | 0 | 0.1 | 98.71 | 93.28 | 95.38 |
| 7 | 3.5 | 0 | 0 | 0 | 0 | 130 | 0 | 0 | 0 | 98.40 | 90.65 | 96.54 |
| 8 | 3.5 | 0 | 0 | 0 | 240 | 0 | 0 | 0 | 0 | 98.03 | 93.94 | 96.82 |
| 9 | 5.2 | 0 | 0 | 0 | 240 | 0 | 0 | 0 | 0 | 98.23 | 97.19 | 97.12 |
| 10 | 3.5 | 0 | 0 | 0 | 100 | 100 | 0 | 0 | 0 | 98.13 | 91.10 | 96.67 |
| 11 | 5.2 | 0 | 0 | 0 | 100 | 100 | 0 | 0 | 0 | 98.13 | 97.17 | 97.12 |
| 12 | 3.5 | 0 | 0 | 0 | 150 | 50 | 0 | 0 | 0 | 98.07 | 93.40 | 96.48 |

TABLE E-4

Percentage of bands for light chain (LC), heavy chain (HC), non-glycosylated HC, and other species for formulations in Block E at t0, t1 (one week at 40° C.), and t2 (two weeks at 25° C.)

| Form No. | Time | LC | HC | ngHC | Other |
|---|---|---|---|---|---|
| 1 | t0 | 29.97 | 68.80 | 0.59 | 0.64 |
| | t1 | 28.49 | 70.07 | 0.60 | 0.81 |
| | t2 | 28.21 | 70.29 | 0.59 | 0.90 |
| 2 | t0 | 28.50 | 68.67 | 0.52 | 2.31 |
| | t1 | 29.69 | 50.92 | 0.30 | 19.09 |
| | t2 | 28.76 | 69.64 | 0.60 | 1.00 |
| 3 | t0 | 24.30 | 74.01 | 0.60 | 1.09 |
| | t1 | 28.27 | 69.63 | 0.60 | 1.51 |
| | t2 | 28.17 | 69.89 | 0.54 | 1.40 |
| 4 | t0 | 29.45 | 68.73 | 0.56 | 1.26 |
| | t1 | 29.52 | 51.33 | 0.30 | 18.86 |
| | t2 | 27.92 | 65.73 | 0.52 | 5.83 |
| 5 | t0 | 35.59 | 63.85 | 0.56 | 0.00 |
| | t1 | 32.47 | 48.72 | 0.30 | 18.52 |
| | t2 | 34.98 | 60.88 | 0.46 | 3.68 |
| 6 | t0 | 34.33 | 63.39 | 0.51 | 1.77 |
| | t1 | | | | |
| | t2 | 35.32 | 61.31 | 0.45 | 2.92 |
| 7 | t0 | 30.13 | 68.87 | 0.60 | 0.40 |
| | t1 | 28.13 | 54.79 | 0.59 | 16.49 |
| | t2 | 34.39 | 63.32 | 0.53 | 1.76 |
| 8 | t0 | 33.27 | 64.97 | 0.55 | 1.21 |
| | t1 | 33.20 | 52.62 | 0.33 | 13.85 |
| | t2 | 33.25 | 65.26 | 0.58 | 0.92 |
| 9 | t0 | 32.28 | 66.34 | 0.57 | 0.81 |
| | t1 | 31.81 | 65.76 | 0.57 | 1.86 |
| | t2 | 31.23 | 66.81 | 0.57 | 1.39 |
| 10 | t0 | 35.66 | 63.36 | 0.43 | 0.56 |
| | t1 | 24.96 | 58.61 | 0.33 | 16.10 |
| | t2 | 33.44 | 66.03 | 0.53 | 0.00 |
| 11 | t0 | 29.75 | 69.08 | 0.60 | 0.57 |
| | t1 | 27.67 | 70.83 | 0.61 | 0.89 |
| | t2 | 28.81 | 69.86 | 0.59 | 0.73 |
| 12 | t0 | 30.23 | 49.07 | 0.26 | 20.44 |
| | t1 | 28.14 | 70.11 | 0.58 | 1.18 |
| | t2 | 29.75 | 69.08 | 0.60 | 0.57 |

TABLE E-5

Percentage of main bands seen in the cIEF profile of formulations in Block E at t0, t1 (one week at 40° C.), and t2 (two weeks at 25° C.

| Form No. | pH | t0 | t1 | t2 |
|---|---|---|---|---|
| 1 | 8.56 | | | |
| | 8.37 | | 12.52 | 12.65 |
| | 8.23 | | 51.77 | 50.04 |
| | 8.14 | | | |
| | 8.03 | | 21.54 | 12.40 |
| | 7.93 | | 14.17 | 16.26 |
| 2 | | | 1.88 | 1.49 |
| | 8.37 | 10.07 | 17.66 | 14.15 |
| | 8.21 | 37.52 | 32.26 | 33.88 |
| | 8.13 | 19.03 | 9.96 | |
| | 8.01 | 16.57 | | 28.70 |
| | 7.93 | 4.12 | 7.45 | |
| 4 | 8.54 | 1.04 | 2.67 | |
| | 8.38 | 10.50 | 9.32 | |
| | 8.21 | 68.34 | 31.91 | |
| | 8.13 | | 28.52 | |
| | 8.02 | 16.55 | 10.05 | |
| | 7.88 | 3.57 | 8.67 | |
| 5 | | | | |
| 6 | | | | |
| 7 | | | | |
| 8 | | | | |
| 9 | 8.60 | 1.40 | 2.60 | 3.26 |
| | 8.43 | 10.04 | 12.33 | 12.03 |
| | 8.26 | 62.39 | 63.19 | 63.89 |
| | 8.14 | | | |
| | 8.03 | 15.00 | 16.95 | 16.57 |
| | 7.88 | 7.08 | 4.93 | 4.25 |

Results of Block E Studies

The pH stability was modest, with increases in pH occurring at t1 for many of the formulations, especially those buffered with acetate at low pH (Table E-1 above). Two of the samples (Formulations 6 and 12) gelled at t1.

There were sizable losses in monomer content for the pH3.5 samples (Table E-3), whereas the pH 5.2 samples displayed stability comparable to what was seen in the preceding Blocks. It was also clear that the degradation was much more pronounced at 40 C than at 25, despite being stored for twice the length of time. In fact, Formulation 8 lost less than 1% monomer at t2 (Table E-2). The Gly and Arg formulations all displayed good stability, provided the pH was held 5.2. The data in this block of studies confirm our discovery that glycine or arginine, or a mixture thereof are good stabilizers in an adalimumab formulation.

The RP HPLC data shows large decreases in purity, although not nearly as great as for monomer loss by SEC (Table E-3). This suggests that chemical instability is less than physical instability. As with the SEC results, the loss of stability is more pronounced at t1 than at t2.

The CE-SDS results show large increases in new peaks, with the Other category increasing to 15-20% for low pH samples at t1 (Table E-4). The most stable formulation by CE-SDS appears to be Formulation 11, which contains both Gly and Arg as the tonicity modifiers/stabilizers.

We encountered difficulties running the cIEF for many of the Block E samples. However, given the clearly inferior stability at pH 3.5, it is unlikely that cIEF would provide any new information on those stability profiles. For example, Formulation 4 (pH 3.5) shows a splitting of the main peak at t1.

Block F Formulation Studies

The Block F studies were intended to investigate the stability for His-containing formulation using either mannitol, Gly or Arg as the sole tonicity modifier (Table F below). It also served as an opportunity to evaluate additives such as EDTA and methionine (Met), which can be effective at slowing oxidation. In addition, one high citrate concentration and one high phosphate concentration formulation were examined.

TABLE F

BLOCK F STUDY DESIGN

| Form No. | API | pH | citrate | phosphate | His | Gly | Arg | mannitol | NaCl | PS 80 | EDTA | Met |
|---|---|---|---|---|---|---|---|---|---|---|---|---|
| 1 | Adalimumab biosimilar | 5.2 | 8 | 18 | 0 | 0 | 0 | 65 | 100 | 0.1 | 0 | 0 |
| 2 | Adalimumab biosimilar | 5.2 | 8 | 18 | 0 | 0 | 0 | 65 | 100 | 0.1 | 0.5 | 0 |
| 3 | Adalimumab biosimilar | 5.2 | 0 | 0 | 10 | 0 | 150 | 0 | 0 | 0 | 0.1 | 0 |
| 4 | Adalimumab biosimilar | 5.2 | 0 | 0 | 10 | 0 | 150 | 0 | 0 | 0 | 0.5 | 0 |
| 5 | Adalimumab biosimilar | 5.2 | 0 | 0 | 10 | 0 | 0 | 240 | 0 | 0 | 0 | 0 |
| 6 | Adalimumab biosimilar | 5.2 | 0 | 0 | 10 | 0 | 0 | 240 | 0 | 0 | 0 | 10 |
| 7 | Adalimumab biosimilar | 5.2 | 0 | 0 | 10 | 0 | 0 | 240 | 0 | 0 | 0 | 50 |
| 8 | Adalimumab biosimilar | 5.2 | 30 | 0 | 0 | 240 | 0 | 0 | 0 | 0 | 0 | 0 |
| 9 | Adalimumab biosimilar | 5.2 | 0 | 30 | 0 | 240 | 0 | 0 | 0 | 0 | 0 | 0 |
| 10 | Adalimumab biosimilar | 5.2 | 0 | 0 | 30 | 240 | 0 | 0 | 0 | 0 | 0 | 0 |
| 11 | Adalimumab biosimilar | 5.2 | 0 | 0 | 20 | 0 | 25 | 120 | 0 | 0.1 | 0 | 0 |
| 12 | Adalimumab biosimilar | 5.2 | 0 | 0 | 20 | 0 | 25 | 120 | 0 | 0.1 | 0 | 0 |

TABLE F-1

Measured pH for Block F formulations at t0 and t1 (one week, 40° C.)

| Form No. | citrate | phosphate | His | Gly | Arg | mannitol | NaCl | PS 80 | EDTA | Met | t0 | t1 | t2 |
|---|---|---|---|---|---|---|---|---|---|---|---|---|---|
| 1 | 8 | 18 | 0 | 0 | 0 | 65 | 100 | 0.1 | 0 | 0 | 4.67 | 4.88 | 4.77 |
| 2 | 8 | 18 | 0 | 0 | 0 | 65 | 100 | 0.1 | 0.5 | 0 | 5.05 | 5.15 | 5.20 |
| 3 | 0 | 0 | 10 | 0 | 150 | 0 | 0 | 0 | 0.1 | 0 | 5.11 | 5.22 | 5.27 |
| 4 | 0 | 0 | 10 | 0 | 150 | 0 | 0 | 0 | 0.5 | 0 | 4.95 | 5.06 | 5.15 |
| 5 | 0 | 0 | 10 | 0 | 0 | 240 | 0 | 0 | 0 | 0 | 5.12 | 5.25 | 5.29 |
| 6 | 0 | 0 | 10 | 0 | 0 | 240 | 0 | 0 | 0 | 10 | 4.45 | 4.74 | 4.67 |
| 7 | 0 | 0 | 10 | 0 | 0 | 240 | 0 | 0 | 0 | 50 | 5.03 | 5.24 | 5.24 |
| 8 | 30 | 0 | 0 | 240 | 0 | 0 | 0 | 0 | 0 | 0 | 5.09 | 5.18 | 5.22 |
| 9 | 0 | 30 | 0 | 240 | 0 | 0 | 0 | 0 | 0 | 0 | 5.13 | 5.25 | 5.32 |
| 10 | 0 | 0 | 30 | 240 | 0 | 0 | 0 | 0 | 0 | 0 | 5.08 | 5.24 | 5.24 |
| 11 | 0 | 0 | 20 | 0 | 25 | 120 | 0 | 0.1 | 0 | 0 | 5.01 | 5.17 | 5.18 |
| 12 | 0 | 0 | 20 | 0 | 25 | 120 | 0 | 0.1 | 0 | 0 | 5.06 | 5.20 | 5.19 |

TABLE F-2

Monomer content by SEC for formulations in Block F at t0, t1 (one week at 40° C.), and t2 (two weeks at 25° C.)

| Form No. | citrate | phosphate | His | Gly | Arg | mannitol | NaCl | PS 80 | EDTA | Met | t0 | t1 | t2 |
|---|---|---|---|---|---|---|---|---|---|---|---|---|---|
| 1 | 8 | 18 | 0 | 0 | 0 | 65 | 100 | 0.1 | 0 | 0 | 97.69 | 94.75 | 96.06 |
| 2 | 8 | 18 | 0 | 0 | 0 | 65 | 100 | 0.1 | 0.5 | 0 | 99.25 | 98.14 | 98.92 |
| 3 | 0 | 0 | 10 | 0 | 150 | 0 | 0 | 0 | 0.1 | 0 | 99.30 | 98.54 | 99.16 |

TABLE F-2-continued

Monomer content by SEC for formulations in Block F at t0, t1 (one week at 40° C.), and t2 (two weeks at 25° C.)

| Form No. | citrate | phosphate | His | Gly | Arg | mannitol | NaCl | PS 80 | EDTA | Met | t0 | t1 | t2 |
|---|---|---|---|---|---|---|---|---|---|---|---|---|---|
| 4 | 0 | 0 | 10 | 0 | 150 | 0 | 0 | 0 | 0.5 | 0 | 99.28 | 98.31 | 99.14 |
| 5 | 0 | 0 | 10 | 0 | 0 | 240 | 0 | 0 | 0 | 0 | 99.17 | 98.64 | 99.14 |
| 6 | 0 | 0 | 10 | 0 | 0 | 240 | 0 | 0 | 0 | 10 | 99.07 | 98.50 | 99.07 |
| 7 | 0 | 0 | 10 | 0 | 0 | 240 | 0 | 0 | 0 | 50 | 99.29 | 98.92 | 99.24 |
| 8 | 30 | 0 | 0 | 240 | 0 | 0 | 0 | 0 | 0 | 0 | 99.28 | 98.40 | 99.04 |
| 9 | 0 | 30 | 0 | 240 | 0 | 0 | 0 | 0 | 0 | 0 | 99.30 | 98.50 | 99.08 |
| 10 | 0 | 0 | 30 | 240 | 0 | 0 | 0 | 0 | 0 | 0 | 99.31 | 98.60 | 99.23 |
| 11 | 0 | 0 | 20 | 0 | 25 | 120 | 0 | 0.1 | 0 | 0 | 99.27 | 98.64 | 99.16 |
| 12 | 0 | 0 | 20 | 0 | 25 | 120 | 0 | 0.1 | 0 | 0 | 99.29 | 98.51 | 99.17 |

TABLE F-3

Percent purity by RP HPLC for formulations in Block F at t0, t1 (one week at 40° C.), and t2 (two weeks at 25° C.)

| Form No. | citrate | phosphate | His | Gly | Arg | mannitol | NaCl | PS 80 | EDTA | Met | t0 | t1 | t2 |
|---|---|---|---|---|---|---|---|---|---|---|---|---|---|
| 1 | 8 | 18 | 0 | 0 | 0 | 65 | 100 | 0.1 | 0 | 0 | 97.47 | 96.89 | 97.98 |
| 2 | 8 | 18 | 0 | 0 | 0 | 65 | 100 | 0.1 | 0.5 | 0 | 97.33 | 97.02 | 97.99 |
| 3 | 0 | 0 | 10 | 0 | 150 | 0 | 0 | 0 | 0.1 | 0 | 97.64 | 97.14 | 98.04 |
| 4 | 0 | 0 | 10 | 0 | 150 | 0 | 0 | 0 | 0.5 | 0 | 97.59 | 97.00 | 97.97 |
| 5 | 0 | 0 | 10 | 0 | 0 | 240 | 0 | 0 | 0 | 0 | 97.11 | 97.30 | 98.03 |
| 6 | 0 | 0 | 10 | 0 | 0 | 240 | 0 | 0 | 0 | 10 | 97.61 | 97.27 | 98.03 |
| 7 | 0 | 0 | 10 | 0 | 0 | 240 | 0 | 0 | 0 | 50 | 97.55 | 97.37 | 98.08 |
| 8 | 30 | 0 | 0 | 240 | 0 | 0 | 0 | 0 | 0 | 0 | 97.48 | 97.51 | 98.05 |
| 9 | 0 | 30 | 0 | 240 | 0 | 0 | 0 | 0 | 0 | 0 | 97.64 | 97.58 | 98.03 |
| 10 | 0 | 0 | 30 | 240 | 0 | 0 | 0 | 0 | 0 | 0 | 97.68 | 97.41 | 98.06 |
| 11 | 0 | 0 | 20 | 0 | 25 | 120 | 0 | 0.1 | 0 | 0 | 97.67 | 97.18 | 98.03 |
| 12 | 0 | 0 | 20 | 0 | 25 | 120 | 0 | 0.1 | 0 | 0 | 97.68 | 97.33 | 98.02 |

TABLE F-4

Percentage of bands for light chain (LC), heavy chain (HC), non-glycosylated HC, and other species for formulations in Block F at t0, t1 (one week at 40° C.), and t2 (two weeks at 25° C.)

| Form No. | Time | LC | HC | ngHC | Other |
|---|---|---|---|---|---|
| 1 | t0 | 27.36 | 71.86 | 0.60 | 0.17 |
|   | t1 | 25.34 | 73.18 | 0.63 | 0.86 |
|   | t2 |  |  |  |  |
| 2 | t0 | 27.80 | 71.07 | 0.60 | 0.53 |
|   | t1 | 28.29 | 71.08 | 0.63 | 0.00 |
|   | t2 | 27.53 | 70.97 | 0.64 | 0.86 |
| 3 | t0 | 27.78 | 70.62 | 0.65 | 0.95 |
|   | t1 | 28.26 | 70.85 | 0.66 | 0.23 |
|   | t2 | 28.26 | 70.50 | 0.63 | 0.61 |
| 4 | t0 | 28.20 | 70.24 | 0.60 | 0.96 |
|   | t1 | 29.17 | 69.30 | 0.74 | 0.80 |
|   | t2 | 29.17 | 70.27 | 0.56 | 0.00 |
| 5 | t0 | 27.50 | 70.74 | 0.59 | 1.17 |
|   | t1 | 29.56 | 65.79 | 0.41 | 4.24 |
|   | t2 | 28.24 | 69.90 | 0.58 | 1.28 |
| 6 | t0 | 29.10 | 68.84 | 0.54 | 1.52 |
|   | t1 | 28.58 | 69.18 | 0.54 | 1.70 |
|   | t2 | 27.47 | 70.39 | 0.54 | 1.60 |
| 7 | t0 | 27.87 | 70.28 | 0.55 | 1.30 |
|   | t1 |  |  |  |  |
|   | t2 |  |  |  |  |
| 8 | t0 | 34.72 | 64.87 | 0.41 | 0.00 |
|   | t1 | 34.94 | 64.53 | 0.53 | 0.00 |
|   | t2 | 33.21 | 65.76 | 0.50 | 0.52 |
| 9 | t0 | 31.96 | 68.04 | 0 | 0 |
|   | t1 | 48.51 | 51.49 | 0 | 0 |
|   | t2 | 33.15 | 65.82 | 0.57 | 0.46 |
| 10 | t0 | 27.81 | 71.27 | 0.51 | 0.40 |
|   | t1 | 29.59 | 68.46 | 0.53 | 1.43 |
|   | t2 | 31.25 | 67.89 | 0.50 | 0.36 |
| 11 | t0 | 27.33 | 70.80 | 0.61 | 1.26 |
|   | t1 | 26.54 | 71.00 | 0.64 | 1.82 |
|   | t2 | 29.46 | 69.85 | 0.69 | 0.00 |
| 12 | t0 | 24.18 | 71.21 | 0 | 4.61 |
|    | t1 |  |  |  |  |
|    | t2 | 28.95 | 68.98 | 0.59 | 1.46 |

TABLE F-5

Percentage of main bands seen in the cIEF profile of formulations in Block F at t0, t1 (one week at 40° C.), and t2 (two weeks at 25° C.

| Form No. | pH | t0 | t1 | t2 |
|---|---|---|---|---|
| 1 | 8.65 |  |  | 2.11 |
|   | 8.31 | 13.07 | 11.43 | 34.17 |
|   | 8.24 | 64.66 | 67.99 | 28.67 |
|   | 8.14 |  |  | 2.29 |
|   | 8.08 | 16.13 | 17.73 | 15.98 |
|   | 7.95 | 6.14 |  | 4.80 |

TABLE F-5-continued

Percentage of main bands seen in the cIEF profile of formulations in Block F at t0, t1 (one week at 40° C.), and t2 (two weeks at 25° C.

| Form No. | pH | t0 | t1 | t2 |
|---|---|---|---|---|
| 2 | 8.60 | 1.56 | 1.93 | 1.12 |
|   | 8.48 | 12.95 | 11.26 | 11.12 |
|   | 8.24 | 58.99 | 55.85 | 60.37 |
|   | 8.13 | 20.98 | 22.43 | 18.77 |
|   | 7.93 | 3.56 | 6.41 | 6.09 |
|   | 8.60 | 1.56 | 1.93 | 1.12 |
| 3 | 8.56 |  | 1.56 | 1.69 |
|   | 8.34 | 10.88 | 12.85 | 10.83 |
|   | 8.18 | 66.93 | 55.35 | 62.00 |
|   | 8.02 | 17.28 | 19.04 | 20.13 |
|   | 7.89 | 4.91 | 11.21 | 5.35 |
| 4 | 8.58 | 1.86 | 1.68 |  |
|   | 8.45 | 13.79 | 10.61 | 12.84 |
|   | 8.27 | 65.06 | 51.89 | 61.94 |
|   | 8.06 | 19.29 | 18.85 | 25.22 |
|   | 7.96 | 6.28 | 4.91 |  |
| 5 | 8.60 | 1.35 | 1.78 | 1.45 |
|   | 8.45 | 12.35 | 13.63 | 8.59 |
|   | 8.27 | 60.12 | 55.07 | 64.28 |
|   | 8.07 | 20.50 | 20.35 | 19.73 |
|   | 7.94 | 5.69 | 9.17 | 5.95 |
| 6 | 8.55 | 1.30 | 1.30 | 1.08 |
|   | 8.43 | 13.29 | 13.26 | 13.23 |
|   | 8.24 | 54.83 | 56.88 | 61.67 |
|   | 8.08 | 20.76 | 19.79 | 17.19 |
|   | 7.96 | 9.82 | 8.76 | 6.84 |
| 7 | 8.57 | 1.28 | 1.41 | 2.40 |
|   | 8.44 | 12.08 | 12.63 | 13.05 |
|   | 8.27 | 61.50 | 55.33 | 60.70 |
|   | 8.08 | 17.55 | 19.48 | 17.43 |
|   | 7.94 | 5.93 | 8.92 | 4.25 |
| 8 | 8.55 | 1.32 | 0.90 |  |
|   | 8.43 | 11.51 | 12.47 | 10.09 |
|   | 8.24 | 62.99 | 54.09 | 63.81 |
|   | 8.05 | 15.43 | 22.71 | 20.91 |
|   | 7.90 | 8.75 | 9.83 | 5.19 |
| 9 | 8.59 | 1.35 |  | 1.63 |
|   | 8.45 | 11.59 | 13.67 | 11.40 |
|   | 8.28 | 63.60 | 52.70 | 63.11 |
|   | 8.06 | 17.98 | 24.08 | 18.57 |
|   | 7.94 | 2.28 | 7.05 | 5.29 |
| 10 | 8.57 | 1.56 | 2.50 | 2.08 |
|   | 8.45 | 13.22 | 11.93 | 12.90 |
|   | 8.28 | 61.86 | 55.12 | 61.87 |
|   | 8.08 | 17.87 | 20.99 | 18.74 |
|   | 7.97 | 5.50 | 4.71 | 4.41 |
| 11 | 8.59 | 1.43 | 1.19 |  |
|   | 8.45 | 12.25 | 11.42 | 9.85 |
|   | 8.28 | 58.83 | 59.88 | 64.13 |
|   | 8.08 | 18.18 | 22.06 | 17.46 |
|   | 7.97 | 9.61 | 5.45 | 6.97 |
| 12 | 8.56 | 1.64 | 1.39 | 0.94 |
|   | 8.39 | 15.30 | 13.07 | 15.71 |
|   | 8.21 | 63.76 | 59.71 | 62.92 |
|   | 8.02 | 16.72 | 20.51 | 16.60 |
|   | 7.97 | 2.58 | 4.21 | 3.85 |

Results of Block F

In this block of formulations, the pH values were all slightly lower than the target value of pH 5.2 (Table F-1). In addition, the pH does change by about 0.1 units for most of the formulations when measured at t1. These differences were considered when constructing mathematical models of the data, as discussed below.

The addition of EDTA does appear to improve stability for the worst formulation (Formulation 1). Whether it increases stability in general was less clear, based on the SEC data (Table F-2). The formulations containing high concentrations of Arg or Gly all performed quite well upon storage (Table F-2).

The initial purities by RP HPLC were universally lower than expected for these formulations (Table F-3). Upon storage at t1 and t2, there are some slight differences, with Gly- and Arg-based formulations showing the greatest stability. Based upon the RP HPLC data, EDTA does not appear to be a significant stabilizer (Table F-3). Likewise, the effect of Met appears to be minimal on stability as measured by RP HPLC or SEC, with the exception of the monomer content for the highest Met concentration (Table F-2, Formulation 7).

Analysis by CE-SDS indicates that very little degradation occurs upon storage (usually less than 1% increase in 'Other') (Table F-4). However, there are some formulations that begin with higher 'Other' contents (Formulations 4 through 7, for example). These are all formulations using a high concentration of mannitol (240 mM). The same seems to be true for formulations containing 120 mM mannitol.

As for analysis by cIEF, there is little change in the relative intensities of the main peak, at least in a systematic fashion that would allow one to discern stability trends (Table F-5). In general, the changes are smaller at t2 than at t1.

Block G Formulation Studies

The Block G formulation studies examined a variety of formulations with combinations of Gly and Arg as the primary stabilizers (Table XXXIV). In addition, two other surfactants (Pluronic F-68 and polysorbate 20, PS 20) were evaluated in addition to PS 80. Finally, a range of PS 80 concentrations was evaluated.

TABLE G

BLOCK G STUDY DESIGN

| Form No. | API | citrate | phosphate | succinate | HIS | Gly | Arg | mannitol | NaCl | F68 | PS20 | PS80 |
|---|---|---|---|---|---|---|---|---|---|---|---|---|
| 1 | Adalimumab biosimilar | 8 | 18 | 0 | 0 | 0 | 0 | 65 | 100 | 0 | 0 | 0.1 |
| 2 | Adalimumab biosimilar | 8 | 18 | 0 | 0 | 0 | 0 | 65 | 100 | 0 | 0.1 | 0 |
| 3 | Adalimumab biosimilar | 8 | 18 | 0 | 0 | 0 | 0 | 65 | 100 | 0.1 | 0 | 0 |
| 4 | Adalimumab biosimilar | 0 | 0 | 0 | 10 | 120 | 120 | 0 | 0 | 0 | 0 | 0.1 |

TABLE G-continued

BLOCK G STUDY DESIGN

| Form No. | API | citrate | phosphate | succinate | HIS | Gly | Arg | mannitol | NaCl | F68 | PS20 | PS80 |
|---|---|---|---|---|---|---|---|---|---|---|---|---|
| 5 | Adalimumab biosimilar | 0 | 0 | 0 | 10 | 120 | 120 | 0 | 0 | 0 | 0 | 0.05 |
| 6 | Adalimumab biosimilar | 0 | 0 | 0 | 10 | 120 | 120 | 0 | 0 | 0 | 0 | 0.01 |
| 7 | Adalimumab biosimilar | 0 | 0 | 0 | 10 | 120 | 120 | 0 | 0 | 0 | 0.05 | 0 |
| 8 | Adalimumab biosimilar | 0 | 0 | 0 | 10 | 120 | 120 | 0 | 0 | 0.1 | 0 | 0 |
| 9 | Adalimumab biosimilar | 0 | 0 | 10 | 0 | 120 | 120 | 0 | 0 | 0 | 0 | 0.05 |
| 10 | Adalimumab biosimilar | 0 | 0 | 20 | 0 | 150 | 100 | 0 | 0 | 0 | 0.05 | 0 |
| 11 | Adalimumab biosimilar | 0 | 0 | 0 | 20 | 150 | 100 | 0 | 0 | 0 | 0 | 0.01 |
| 12 | Adalimumab biosimilar | 0 | 0 | 0 | 20 | 120 | 120 | 0 | 0 | 0 | 0.01 | 0 |

TABLE G-1

Measured pH for Block G formulations at t0, t1 (one week, 40° C.), and t2 (two weeks, 40° C.)

| Form No. | citrate | phosphate | succinate | His | Gly | Arg | mannitol | NaCl | F68 | PS20 | PS80 | t0 | t1 | t2 |
|---|---|---|---|---|---|---|---|---|---|---|---|---|---|---|
| 1 | 8 | 18 | 0 | 0 | 0 | 0 | 65 | 100 | 0 | 0 | 0.1 | 5.19 | 5.38 | 5.25 |
| 2 | 8 | 18 | 0 | 0 | 0 | 0 | 65 | 100 | 0 | 0.1 | 0 | 5.23 | 5.28 | 5.24 |
| 3 | 8 | 18 | 0 | 0 | 0 | 0 | 65 | 100 | 0.1 | 0 | 0 | 5.22 | 5.26 | 5.20 |
| 4 | 0 | 0 | 0 | 10 | 120 | 120 | 0 | 0 | 0 | 0 | 0.1 | 5.20 | 5.33 | 5.29 |
| 5 | 0 | 0 | 0 | 10 | 120 | 120 | 0 | 0 | 0 | 0 | 0.05 | 5.23 | 5.34 | 5.29 |
| 6 | 0 | 0 | 0 | 10 | 120 | 120 | 0 | 0 | 0 | 0 | 0.01 | 5.19 | 5.40 | 5.27 |
| 7 | 0 | 0 | 0 | 10 | 120 | 120 | 0 | 0 | 0 | 0.05 | 0 | 5.23 | 5.39 | 5.42 |
| 8 | 0 | 0 | 0 | 10 | 120 | 120 | 0 | 0 | 0.1 | 0 | 0 | 5.19 | 5.38 | 5.41 |
| 9 | 0 | 0 | 10 | 0 | 120 | 120 | 0 | 0 | 0 | 0 | 0.05 | 5.19 | 5.27 | 5.24 |
| 10 | 0 | 0 | 20 | 0 | 150 | 100 | 0 | 0 | 0 | 0.05 | 0 | 5.23 | 5.28 | 5.24 |
| 11 | 0 | 0 | 0 | 20 | 150 | 100 | 0 | 0 | 0 | 0 | 0.01 | 5.23 | 5.33 | 5.27 |
| 12 | 0 | 0 | 0 | 20 | 120 | 120 | 0 | 0 | 0 | 0.01 | 0 | 5.22 | 5.29 | 5.29 |

TABLE G-2

Monomer content by SEC for formulations in Block G at t0, t1 (one week at 40° C.), and t2 (two weeks at 25° C.)

| Form No. | citrate | phosphate | succinate | His | Gly | Arg | mannitol | NaCl | F68 | PS20 | PS80 | t0 | t1 | t2 |
|---|---|---|---|---|---|---|---|---|---|---|---|---|---|---|
| 1 | 8 | 18 | 0 | 0 | 0 | 0 | 65 | 100 | 0 | 0 | 0.1 | 99.17 | 97.45 | 98.09 |
| 2 | 8 | 18 | 0 | 0 | 0 | 0 | 65 | 100 | 0 | 0.1 | 0 | 99.11 | 97.78 | 98.09 |
| 3 | 8 | 18 | 0 | 0 | 0 | 0 | 65 | 100 | 0.1 | 0 | 0 | 98.99 | 97.74 | 97.92 |
| 4 | 0 | 0 | 0 | 10 | 120 | 120 | 0 | 0 | 0 | 0 | 0.1 | 99.12 | 98.67 | 98.68 |
| 5 | 0 | 0 | 0 | 10 | 120 | 120 | 0 | 0 | 0 | 0 | 0.05 | 99.05 | 98.57 | 98.53 |
| 6 | 0 | 0 | 0 | 10 | 120 | 120 | 0 | 0 | 0 | 0 | 0.01 | 99.05 | 98.66 | 98.70 |
| 7 | 0 | 0 | 0 | 10 | 120 | 120 | 0 | 0 | 0 | 0.05 | 0 | 99.04 | 98.63 | 98.50 |
| 8 | 0 | 0 | 0 | 10 | 120 | 120 | 0 | 0 | 0.1 | 0 | 0 | 99.11 | 98.64 | 98.55 |
| 9 | 0 | 0 | 10 | 0 | 120 | 120 | 0 | 0 | 0 | 0 | 0.05 | 99.12 | 98.56 | 98.98 |
| 10 | 0 | 0 | 20 | 0 | 150 | 100 | 0 | 0 | 0 | 0.05 | 0 | 99.10 | 98.49 | 98.88 |
| 11 | 0 | 0 | 0 | 20 | 150 | 100 | 0 | 0 | 0 | 0 | 0.01 | 99.07 | 98.76 | 98.45 |
| 12 | 0 | 0 | 0 | 20 | 120 | 120 | 0 | 0 | 0 | 0.01 | 0 | 99.11 | | 98.48 |

TABLE G-3

Percent purity by RP HPLC for formulations in Block G at t0, t1 (one week at 40° C.), and t2 (two weeks at 25° C.

| Form No. | citrate | phosphate | succinate | HIS | Gly | Arg | mannitol | NaCl | F68 | PS20 | PS80 | t0 | t1 | t2 |
|---|---|---|---|---|---|---|---|---|---|---|---|---|---|---|
| 1 | 8 | 18 | 0 | 0 | 0 | 0 | 65 | 100 | 0 | 0 | 0.1 | 99.74 | 99.66 | 98.93 |
| 2 | 8 | 18 | 0 | 0 | 0 | 0 | 65 | 100 | 0 | 0.1 | 0 | 99.59 | 99.66 | 98.97 |
| 3 | 8 | 18 | 0 | 0 | 0 | 0 | 65 | 100 | 0.1 | 0 | 0 | 99.58 | 99.60 | 99.22 |
| 4 | 0 | 0 | 0 | 10 | 120 | 120 | 0 | 0 | 0 | 0 | 0.1 | 99.62 | 99.62 | 98.99 |

TABLE G-3-continued

Percent purity by RP HPLC for formulations in Block G at t0, t1 (one week at 40° C.), and t2 (two weeks at 25° C.)

| Form No. | citrate | phosphate | succinate | HIS | Gly | Arg | mannitol | NaCl | F68 | PS20 | PS80 | t0 | t1 | t2 |
|---|---|---|---|---|---|---|---|---|---|---|---|---|---|---|
| 5 | 0 | 0 | 0 | 10 | 120 | 120 | 0 | 0 | 0 | 0 | 0.05 | 99.70 | 99.61 | 99.01 |
| 6 | 0 | 0 | 0 | 10 | 120 | 120 | 0 | 0 | 0 | 0 | 0.01 | 99.60 | 99.66 | 99.00 |
| 7 | 0 | 0 | 0 | 10 | 120 | 120 | 0 | 0 | 0 | 0.05 | 0 | 99.71 | 99.65 | 98.99 |
| 8 | 0 | 0 | 0 | 10 | 120 | 120 | 0 | 0.1 | 0 | 0 | 0 | 99.70 | 99.61 | 99.03 |
| 9 | 0 | 0 | 10 | 0 | 120 | 120 | 0 | 0 | 0 | 0.05 | 0 | 99.71 | 99.60 | 99.03 |
| 10 | 0 | 0 | 20 | 0 | 150 | 100 | 0 | 0 | 0 | 0.05 | 0 | 99.72 | 99.60 | 99.02 |
| 11 | 0 | 0 | 0 | 20 | 150 | 100 | 0 | 0 | 0 | 0 | 0.01 | 99.72 | 99.61 | 99.05 |
| 12 | 0 | 0 | 0 | 20 | 120 | 120 | 0 | 0 | 0 | 0.01 | 0 | 99.61 | | 99.04 |

TABLE G-4

Percentage of bands for light chain (LC), heavy chain (HC), non-glycosylated HC, and other species for formulations in Block G at t0, t1 (one week at 40° C.), and t2 (two weeks at 25° C.)

| Form No. | Time | LC | HC | ngHC | Other |
|---|---|---|---|---|---|
| 1 | t0 | 28.55 | 70.77 | 0.50 | 0.17 |
|  | t1 | 29.71 | 69.42 | 0.57 | 0.30 |
|  | t2 | 30.32 | 68.80 | 0.53 | 0.35 |
| 2 | t0 | 37.14 | 62.38 | 0.49 | 0.00 |
|  | t1 | 30.31 | 69.38 | 0.28 | 0.03 |
|  | t2 | 31.60 | 67.87 | 0.53 | 0.00 |
| 3 | t0 | 28.95 | 70.40 | 0.65 | 0.00 |
|  | t1 | 28.17 | 70.26 | 0.58 | 0.99 |
|  | t2 | 27.32 | 71.52 | 0.56 | 0.59 |
| 4 | t0 | 29.56 | 69.02 | 0.65 | 0.77 |
|  | t1 | 32.19 | 66.09 | 0.53 | 1.19 |
|  | t2 | 31.58 | 66.03 | 0.57 | 1.81 |
| 5 | t0 | 36.54 | 62.48 | 0.56 | 0.42 |
|  | t1 | 28.77 | 69.28 | 0.62 | 1.33 |
|  | t2 | 23.76 | 74.49 | 0.60 | 1.16 |
| 6 | t0 | 29.60 | 68.61 | 0.58 | 1.21 |
|  | t1 | 30.37 | 67.42 | 0.59 | 1.61 |
|  | t2 | 32.27 | 66.08 | 0.59 | 1.06 |
| 7 | t0 | 31.90 | 65.50 | 0.63 | 1.97 |
|  | t1 | 31.26 | 66.66 | 0.56 | 1.51 |
|  | t2 | 31.37 | 66.64 | 0.67 | 1.31 |
| 8 | t0 | 31.04 | 67.38 | 0.54 | 1.04 |
|  | t1 | 30.34 | 67.99 | 0.62 | 1.05 |
|  | t2 | 30.21 | 67.63 | 0.68 | 1.48 |
| 9 | t0 | 33.12 | 65.34 | 0.61 | 0.94 |
|  | t1 | 34.01 | 63.97 | 0.56 | 1.46 |
|  | t2 | 34.47 | 63.77 | 0.57 | 1.19 |
| 10 | t0 | 36.78 | 61.61 | 0.54 | 1.07 |
|  | t1 | 39.25 | 58.66 | 0.53 | 1.56 |
|  | t2 | 32.83 | 65.42 | 0.55 | 1.21 |
| 11 | t0 | 36.37 | 61.97 | 0.54 | 1.11 |
|  | t1 |  |  |  |  |
|  | t2 | 34.97 | 63.14 | 0.54 | 1.36 |
| 12 | t0 | 34.26 | 64.16 | 0.52 | 1.05 |
|  | t1 |  |  |  |  |
|  | t2 | 34.90 | 63.35 | 0.56 | 1.19 |

TABLE G-5

Percentage of main bands seen in the cIEF profile of formulations in Block G at t0, t1 (one week at 40° C.), and t2 (two weeks at 25° C.)

| Form No. | pH | t0 | t1 | t2 |
|---|---|---|---|---|
| 1 | 8.53 | 1.24 |  | 1.21 |
|  | 8.36 | 14.30 | 12.69 | 13.67 |
|  | 8.24 | 64.03 | 53.50 | 60.30 |
|  | 8.14 |  |  |  |
|  | 8.01 | 15.77 | 9.32 | 19.12 |
|  | 7.86 | 3.73 | 3.35 | 4.48 |
| 2 | 8.52 | 1.06 | 1.37 | 0.88 |
|  | 8.35 | 13.10 | 13.30 | 12.53 |
|  | 8.16 | 66.28 | 59.68 | 57.99 |
|  | 7.97 | 17.14 | 19.60 | 21.55 |
|  | 7.83 | 2.42 | 4.78 | 4.92 |
| 3 | 8.51 | 0.65 | 0.65 | 1.03 |
|  | 8.34 | 13.31 | 14.00 | 15.31 |
|  | 8.16 | 65.13 | 59.04 | 60.70 |
|  | 8.14 |  |  |  |
|  | 7.98 | 17.26 | 18.90 | 17.56 |
|  | 7.82 | 2.89 | 5.68 | 4.16 |
| 4 | 8.36 | 1.87 | 2.43 | 1.00 |
|  | 8.19 | 7.74 | 10.89 | 11.69 |
|  | 7.99 | 61.91 | 54.27 | 59.10 |
|  | 7.82 | 20.94 | 22.72 | 19.81 |
|  | 7.66 | 6.35 | 7.98 | 6.92 |
| 5 | 8.44 | 1.79 | 0.95 | 071 |
|  | 8.26 | 13.33 | 12.85 | 10.43 |
|  | 8.06 | 61.67 | 59.94 | 60.12 |
|  | 7.88 | 17.49 | 21.08 | 20.82 |
|  | 7.69 | 4.02 | 4.50 | 6.50 |
| 6 | 8.36 | 1.71 | 4.76 |  |
|  | 8.21 | 12.37 | 12.93 | 10.95 |
|  | 8.04 | 62.53 | 54.16 | 56.48 |
|  | 7.87 | 19.24 | 26.08 | 17.97 |
|  | 7.64 | 4.15 | 2.07 | 6.50 |
| 7 | 8.54 | 0.77 | 1.19 | 0.79 |
|  | 8.34 | 7.15 | 12.32 | 13.15 |
|  | 8.17 | 54.73 | 42.64 | 60.58 |
|  | 8.02 | 22.18 | 29.90 | 17.28 |
|  | 7.83 | 7.12 | 11.47 | 4.77 |
|  | 7.69 | 1.41 | 2.48 | 2.11 |
| 8 | 8.55 |  | 1.04 | 2.11 |
|  | 8.39 | 7.28 | 10.69 | 14.82 |
|  | 8.23 | 64.01 | 57.42 | 55.68 |
|  | 8.05 | 20.81 | 23.86 | 23.76 |
|  | 7.96 | 6.79 | 5.37 | 5.74 |
| 9 | 8.54 |  |  |  |
|  | 8.48 | 10.99 | 7.91 |  |
|  | 8.31 | 53.85 | 61.43 |  |
|  | 8.17 | 31.58 | 23.83 |  |
|  | 7.99 |  | 8.82 |  |
|  | 7.85 | 3.58 | 3.27 |  |
| 10 | 8.50 | 0.95 | 2.16 |  |
|  | 8.36 | 9.10 | 10.65 | 15.79 |
|  | 8.18 | 59.02 | 55.35 | 58.56 |
|  | 8.02 | 23.76 | 24.79 | 25.66 |
|  | 7.87 | 5.63 | 7.05 |  |
| 11 | 8.58 |  | 2.08 | 1.68 |
|  | 8.40 | 9.74 | 10.05 | 9.67 |
|  | 8.21 | 62.70 | 56.96 | 57.36 |
|  | 8.05 | 21.39 | 24.14 | 25.18 |
|  | 7.99 | 5.24 | 6.77 | 6.11 |

TABLE G-5-continued

Percentage of main bands seen in the cIEF profile of formulations in Block G at t0, t1 (one week at 40° C.), and t2 (two weeks at 25° C.

| Form No. | pH | t0 | t1 | t2 |
|---|---|---|---|---|
| 12 | 8.54 | 1.67 | | |
| | 8.37 | 15.99 | | |
| | 8.22 | 63.18 | | |
| | 8.02 | 15.41 | | |
| | 7.82 | 3.75 | | |

TABLE G-6

Block G study design for F/T and agitation studies

| Form No. | API | citrate | phosphate | succinate | HIS | Gly | Arg | mannitol | NaCl | F68 | PS20 | PS80 |
|---|---|---|---|---|---|---|---|---|---|---|---|---|
| 1 | Adalimumab biosimilar | 8 | 18 | 0 | 0 | 0 | 0 | 65 | 100 | 0 | 0 | 0.1 |
| 2 | Adalimumab biosimilar | 8 | 18 | 0 | 0 | 0 | 0 | 65 | 100 | 0 | 0.1 | 0 |
| 3 | Adalimumab biosimilar | 8 | 18 | 0 | 0 | 0 | 0 | 65 | 100 | 0.1 | 0 | 0 |
| 4 | Adalimumab biosimilar | 0 | 0 | 0 | 10 | 120 | 120 | 0 | 0 | 0 | 0 | 0.1 |
| 5 | Adalimumab biosimilar | 0 | 0 | 0 | 10 | 120 | 120 | 0 | 0 | 0 | 0 | 0.05 |
| 6 | Adalimumab biosimilar | 0 | 0 | 0 | 10 | 120 | 120 | 0 | 0 | 0 | 0 | 0.01 |
| 7 | Adalimumab biosimilar | 0 | 0 | 0 | 10 | 120 | 120 | 0 | 0 | 0 | 0.05 | 0 |
| 8 | Adalimumab biosimilar | 0 | 0 | 0 | 10 | 120 | 120 | 0 | 0 | 0.1 | 0 | 0 |
| 9 | Adalimumab biosimilar | 0 | 0 | 10 | 0 | 120 | 120 | 0 | 0 | 0 | 0 | 0.05 |
| 10 | Adalimumab biosimilar | 0 | 0 | 20 | 0 | 150 | 100 | 0 | 0 | 0 | 0.05 | 0 |
| 11 | Adalimumab biosimilar | 0 | 0 | 0 | 20 | 150 | 100 | 0 | 0 | 0 | 0 | 0.01 |
| 12 | Adalimumab biosimilar | 0 | 0 | 0 | 20 | 120 | 120 | 0 | 0 | 0 | 0.01 | 0 |

TABLE G-7

Monomer content by SEC for select formulations in Block G that were untreated (Q, quiescent), underwent 5 F/T cycles or subjected to agitation for 24 hours

| Form No. | citrate | phosphate | succinate | HIS | Gly | Arg | mannitol | NaCl | F68 | PS20 | PS80 | Q | F/T | agit |
|---|---|---|---|---|---|---|---|---|---|---|---|---|---|---|
| 1 | 8 | 18 | 0 | 0 | 0 | 0 | 65 | 100 | 0 | 0 | 0.1 | 99.15 | 99.03 | 99.14 |
| 4 | 0 | 0 | 0 | 10 | 120 | 120 | 0 | 0 | 0 | 0 | 0.1 | 99.21 | 99.11 | 99.18 |
| 8 | 0 | 0 | 0 | 10 | 120 | 120 | 0 | 0 | 0.1 | 0 | 0 | 99.18 | 99.14 | 99.17 |
| 11 | 0 | 0 | 0 | 20 | 150 | 100 | 0 | 0 | 0 | 0 | 0.01 | 99.16 | 99.09 | 99.13 |
| 12 | 0 | 0 | 0 | 20 | 120 | 120 | 0 | 0 | 0 | 0.01 | 0 | | 99.10 | |

TABLE G-8

Percent purity by RP HPLC for select formulations in Block G that were untreated (Q, quiescent), underwent 5 F/T cycles or subjected to agitation for 24 hours

| Form No. | citrate | phosphate | succinate | HIS | Gly | Arg | mannitol | NaCl | F68 | PS20 | PS80 | Q | F/T | agit |
|---|---|---|---|---|---|---|---|---|---|---|---|---|---|---|
| 1 | 8 | 18 | 0 | 0 | 0 | 0 | 65 | 100 | 0 | 0 | 0.1 | 99.60 | 99.72 | 99.76 |
| 4 | 0 | 0 | 0 | 10 | 120 | 120 | 0 | 0 | 0 | 0 | 0.1 | 99.56 | 99.70 | 99.59 |
| 8 | 0 | 0 | 0 | 10 | 120 | 120 | 0 | 0 | 0.1 | 0 | 0 | 99.58 | 99.57 | 99.73 |
| 11 | 0 | 0 | 0 | 20 | 150 | 100 | 0 | 0 | 0 | 0 | 0.01 | 99.72 | 99.59 | 99.65 |
| 12 | 0 | 0 | 0 | 20 | 120 | 120 | 0 | 0 | 0 | 0.01 | 0 | 99.75 | 99.56 | |

Results of Block G

All of the pH values were close to the target values (Table G-1), with relatively small changes occurring upon storage. There appears to be some preference in terms of polysorbates over F-68 in terms of stability, as measured by SEC (Table G-2). However, the differences are relatively small. It does appear that succinate formulations (Formulations 9 and 10) fared reasonably well as far as monomer content retained.

The RP HPLC data are all very close, making any determination of stability differences virtually impossible (Table G-3). These data will only be interpretable when examined in the larger context of all of the blocks of screening studies.

The CE-SDS results suggest that PS 20 is the best stabilizer at 0.1% concentration for the Humira® formulation (Formulations 1 through 3) (Table G-4). Otherwise, the differences appear to be too small and variable to make any general conclusions.

As seen before, the results for cIEF data are variable enough to make interpretation difficult (Table G-5). It does appear that the changes are smaller in the Gly/Arg formulations than for formulations using other stabilizers, like mannitol. Still, overall, the stability by cIEF looks to be quite good for many of the formulations in this study.

Block G (F/T and Agitation) Studies.

For a liquid formulation, it is important to evaluate the sensitivity to interfacial stress. Two kinds of stress studies were selected. The first is agitation at 150 rpm on an orbital shaker for 24 hours at 2-8° C. The second is five successive cycles of freezing and thawing (F/T), where this cycle should generate increasing amounts of damage protein, if the protein is sensitive to interfacial damage. Four formulations from Block G were selected for assessment, and they are highlighted in blue bold text Table G-6.

Upon repeated F/T cycling, there is a very small decrease in monomer content for all of the formulations tested (Table G-7). Thus, it seems like there is little interfacial sensitivity form this stress and that the presence of PS 80 is not critical for protection. As for agitated samples, the losses are even smaller. The trends in the RP HPLC data are essentially the same (Table G-8). There are little, if any, losses in purity upon exposure to interfacial stress.

Block H Formulation Studies

The Block H formulations focused on three aspects of the adalimumab formulation: (1) higher protein concentrations, (2) formulations with no buffers present (other than the protein), and (3) the use of various buffer combinations beside citrate-phosphate (See Table H).

TABLE H

BLOCK H STUDY DESIGN

| Form No. | API | protein | citrate | phosphate | succinate | HIS | ACETATE | Gly | Arg | mannitol | NaCl | PS80 |
|---|---|---|---|---|---|---|---|---|---|---|---|---|
| 1 | *** | 100 | 8 | 18 | 0 | 0 | 0 | 0 | 0 | 65 | 100 | 0.1 |
| 2 | *** | 100 | 0 | 0 | 0 | 10 | 0 | 120 | 120 | 0 | 0 | 0.1 |
| 3 | *** | 50 | 0 | 0 | 0 | 0 | 0 | 0 | 0 | 65 | 100 | 0.1 |
| 4 | *** | 50 | 0 | 0 | 0 | 0 | 0 | 120 | 120 | 0 | 0 | 0.1 |
| 5 | *** | 50 | 0 | 0 | 0 | 0 | 0 | 120 | 120 | 0 | 0 | 0 |
| 6 | *** | 50 | 0 | 0 | 0 | 10 | 10 | 0 | 0 | 65 | 100 | 0.1 |
| 7 | *** | 50 | 0 | 0 | 10 | 10 | 0 | 0 | 0 | 65 | 100 | 0.1 |
| 8 | *** | 50 | 0 | 10 | 0 | 10 | 0 | 0 | 0 | 65 | 100 | 0.1 |
| 9 | *** | 50 | 0 | 0 | 10 | 0 | 10 | 0 | 0 | 65 | 100 | 0.1 |
| 10 | *** | 50 | 10 | 0 | 10 | 0 | 0 | 0 | 0 | 65 | 100 | 0.1 |
| 11 | *** | 50 | 10 | 0 | 0 | 10 | 0 | 0 | 0 | 65 | 100 | 0.1 |
| 12 | *** | 50 | 0 | 0 | 10 | 10 | 0 | 120 | 100 | 0 | 0 | 0.1 |

*** denotes proprietary adalimumab biosimilar

TABLE H-1

Measured pH for Block H formulations at t0, t1 (one week, 40° C.), and t2 (two weeks, 40° C.)

| Form No. | protein | Citrate | Phosphate | Succinate | Histidine | acetate | Gly | Arg | Mannitol | NaCl | PS80 | t0 | t1 | t2 |
|---|---|---|---|---|---|---|---|---|---|---|---|---|---|---|
| 1 | 100 | 8 | 18 | 0 | 0 | 0 | 0 | 0 | 65 | 100 | 0.1 | 5.19 | 5.30 | 5.29 |
| 2 | 100 | 0 | 0 | 0 | 10 | 0 | 120 | 120 | 0 | 0 | 0.1 | 5.20 | 5.19 | 5.15 |
| 3 | 50 | 0 | 0 | 0 | 0 | 0 | 0 | 0 | 65 | 100 | 0.1 | 5.21 | 5.23 | 5.21 |
| 4 | 50 | 0 | 0 | 0 | 0 | 0 | 120 | 120 | 0 | 0 | 0.1 | 5.21 | 5.41 | 5.46 |
| 5 | 50 | 0 | 0 | 0 | 0 | 0 | 120 | 120 | 0 | 0 | 0 | 5.21 | 5.30 | 5.39 |
| 6 | 50 | 0 | 0 | 0 | 10 | 10 | 0 | 0 | 65 | 100 | 0.1 | 5.20 | 5.28 | 5.28 |
| 7 | 50 | 0 | 0 | 10 | 10 | 0 | 0 | 0 | 65 | 100 | 0.1 | 5.21 | 5.24 | 5.24 |
| 8 | 50 | 0 | 10 | 0 | 10 | 0 | 0 | 0 | 65 | 100 | 0.1 | 5.20 | 5.17 | 5.16 |
| 9 | 50 | 0 | 0 | 10 | 0 | 10 | 0 | 0 | 65 | 100 | 0.1 | 5.21 | 5.24 | 5.29 |
| 10 | 50 | 10 | 0 | 10 | 0 | 0 | 0 | 0 | 65 | 100 | 0.1 | 5.20 | 5.24 | 5.26 |
| 11 | 50 | 10 | 0 | 0 | 10 | 0 | 0 | 0 | 65 | 100 | 0.1 | 5.21 | 5.24 | 5.26 |
| 12 | 50 | 0 | 0 | 10 | 10 | 0 | 120 | 100 | 0 | 0 | 0.1 | 5.21 | 5.26 | 5.29 |

TABLE H-2

Monomer content by SEC for formulations in Block H at t0, t1 (one week at 40° C.), and t2 (two weeks at 25° C.)

| Form No. | protein | Citrate | Phosphate | Succinate | Histidine | acetate | Gly | Arg | mannitol | NaCl | PS80 | t0 | t1 | t2 |
|---|---|---|---|---|---|---|---|---|---|---|---|---|---|---|
| 1 | 100 | 8 | 18 | 0 | 0 | 0 | 0 | 0 | 65 | 100 | 0.1 | 99.25 | 98.36 | 98.42 |
| 2 | 100 | 0 | 0 | 0 | 10 | 0 | 120 | 120 | 0 | 0 | 0.1 | 99.19 | 98.88 | 98.47 |
| 3 | 50 | 0 | 0 | 0 | 0 | 0 | 0 | 0 | 65 | 100 | 0.1 | 99.06 | 98.81 | 98.74 |
| 4 | 50 | 0 | 0 | 0 | 0 | 0 | 120 | 120 | 0 | 0 | 0.1 | 99.19 | 99.06 | 98.99 |
| 5 | 50 | 0 | 0 | 0 | 0 | 0 | 120 | 120 | 0 | 0 | 0 | 99.26 | 99.03 | 98.96 |
| 6 | 50 | 0 | 0 | 0 | 10 | 10 | 0 | 0 | 65 | 100 | 0.1 | 99.26 | 98.92 | 98.86 |
| 7 | 50 | 0 | 0 | 10 | 10 | 0 | 0 | 0 | 65 | 100 | 0.1 | 99.14 | 98.98 | 98.93 |
| 8 | 50 | 0 | 10 | 0 | 10 | 0 | 0 | 0 | 65 | 100 | 0.1 | 99.11 | 98.93 | 98.66 |
| 9 | 50 | 0 | 0 | 10 | 0 | 10 | 0 | 0 | 65 | 100 | 0.1 | 99.16 | 98.79 | 98.63 |
| 10 | 50 | 10 | 0 | 10 | 0 | 0 | 0 | 0 | 65 | 100 | 0.1 | 99.10 | 98.79 | 98.49 |
| 11 | 50 | 10 | 0 | 0 | 10 | 0 | 0 | 0 | 65 | 100 | 0.1 | 99.21 | 98.93 | 98.18 |
| 12 | 50 | 0 | 0 | 10 | 10 | 0 | 120 | 100 | 0 | 0 | 0.1 | 99.30 | 99.22 | 98.65 |

TABLE H-3

Percent purity by RP HPLC for formulations in Block F at t0, t1 (one week at 40° C.), and t2 (two weeks at 25° C.)

| Form No. | protein | citrate | phosphate | succinate | histidine | acetate | Gly | Arg | mannitol | NaCl | PS80 | t0 | t1 | t2 |
|---|---|---|---|---|---|---|---|---|---|---|---|---|---|---|
| 1 | 100 | 8 | 18 | 0 | 0 | 0 | 0 | 0 | 65 | 100 | 0.1 | 99.36 | 99.64 | 99.64 |
| 2 | 100 | 0 | 0 | 0 | 10 | 0 | 120 | 120 | 0 | 0 | 0.1 | 99.37 | 99.68 | 99.74 |
| 3 | 50 | 0 | 0 | 0 | 0 | 0 | 0 | 0 | 65 | 100 | 0.1 | 99.45 | 99.47 | 99.70 |
| 4 | 50 | 0 | 0 | 0 | 0 | 0 | 120 | 120 | 0 | 0 | 0.1 | 99.50 | 99.69 | 99.59 |
| 5 | 50 | 0 | 0 | 0 | 0 | 0 | 120 | 120 | 0 | 0 | 0 | 99.47 | 99.71 | 99.56 |
| 6 | 50 | 0 | 0 | 0 | 10 | 10 | 0 | 0 | 65 | 100 | 0.1 | 99.48 | 99.56 | 99.72 |
| 7 | 50 | 0 | 0 | 10 | 10 | 0 | 0 | 0 | 65 | 100 | 0.1 | 99.43 | 99.45 | 99.72 |
| 8 | 50 | 0 | 10 | 0 | 10 | 0 | 0 | 0 | 65 | 100 | 0.1 | 99.43 | 99.51 | 99.72 |
| 9 | 50 | 0 | 0 | 10 | 0 | 10 | 0 | 0 | 65 | 100 | 0.1 | 99.47 | 99.55 | 99.72 |
| 10 | 50 | 10 | 0 | 10 | 0 | 0 | 0 | 0 | 65 | 100 | 0.1 | 99.48 | 99.53 | 99.67 |
| 11 | 50 | 10 | 0 | 0 | 10 | 0 | 0 | 0 | 65 | 100 | 0.1 | 99.45 | 99.69 | 99.60 |
| 12 | 50 | 0 | 0 | 10 | 10 | 0 | 120 | 100 | 0 | 0 | 0.1 | 99.44 | 99.54 | 99.72 |

TABLE H-4

Percentage of bands for light chain (LC), heavy chain (HC), non-glycosylated HC, and other species for formulations in Block H at t0, t1 (one week at 40° C.), and t2 (two weeks at 25° C.)

| Form No. | Time | LC | HC | ngHC | Other |
|---|---|---|---|---|---|
| 1 | t0 | 32.87 | 65.48 | 0.54 | 1.11 |
|   | t1 | 28.08 | 70.09 | 0.58 | 1.25 |
|   | t2 | 52.57 | 47.43 | 0.00 | 0.00 |
| 2 | t0 | 36.20 | 62.40 | 0.55 | 0.86 |
|   | t1 | 29.64 | 68.68 | 0.57 | 1.11 |
|   | t2 | 43.09 | 55.23 | 0.57 | 1.10 |
| 3 | t0 | 34.70 | 63.55 | 0.57 | 1.18 |
|   | t1 | 28.24 | 69.72 | 0.61 | 1.57 |
|   | t2 | 34.25 | 63.97 | 0.67 | 1.11 |
| 4 | t0 | 41.04 | 57.61 | 0.51 | 0.84 |
|   | t1 | 27.58 | 70.65 | 0.62 | 1.15 |
|   | t2 | 34.14 | 64.01 | 0.60 | 1.26 |
| 5 | t0 | 37.64 | 60.77 | 0.50 | 1.09 |
|   | t1 | 28.07 | 70.02 | 0.61 | 1.30 |
|   | t2 | 37.67 | 60.76 | 0.55 | 1.02 |
| 6 | t0 | 31.64 | 66.46 | 0.55 | 1.34 |
|   | t1 | 27.67 | 70.19 | 0.50 | 1.64 |
|   | t2 | 34.07 | 63.49 | 0.62 | 1.81 |
| 7 | t0 | 30.38 | 69.10 | 0.53 | 0.00 |
|   | t1 | 27.14 | 70.55 | 0.62 | 1.69 |
|   | t2 | 46.41 | 51.21 | 0.00 | 2.38 |
| 8 | t0 | 28.46 | 71.19 | 0.35 | 0.00 |
|   | t1 | 30.05 | 68.71 | 0.55 | 0.69 |
|   | t2 | 34.14 | 63.97 | 0.63 | 1.25 |
| 9 | t0 | 27.74 | 70.63 | 0.60 | 1.03 |
|   | t1 | 27.48 | 70.48 | 0.61 | 1.43 |
|   | t2 | 36.56 | 61.59 | 0.49 | 1.36 |
| 10 | t0 |  |  |  |  |
|   | t1 | 27.69 | 70.46 | 0.60 | 1.24 |
|   | t2 |  |  |  |  |
| 11 | t0 | 27.64 | 70.83 | 0.57 | 1.13 |
|   | t1 | 31.85 | 66.08 | 0.61 | 1.46 |
|   | t2 | 38.58 | 59.26 | 0.52 | 1.64 |
| 12 | t0 | 29.48 | 68.55 | 0.58 | 1.40 |
|   | t1 | 29.53 | 68.68 | 0.58 | 1.40 |
|   | t2 | 30.64 | 68.20 | 0.70 | 0.46 |

TABLE H-5

Percentage of main bands seen in the cIEF profile of formulations in Block H at t0, t1 (one week at 40° C.), and t2 (two weeks at 25° C.)

| Form No. | pH | t0 | t1 | t2 |
|---|---|---|---|---|
| 1 | 8.55 | 1.20 | 1.17 | 1.21 |
|   | 8.39 | 9.57 | 5.57 | 8.23 |

TABLE H-5-continued

Percentage of main bands seen in the cIEF profile of formulations in Block H at t0, t1 (one week at 40° C.), and t2 (two weeks at 25° C.)

| Form No. | pH | t0 | t1 | t2 |
|---|---|---|---|---|
|  | 8.23 | 46.84 | 38.18 | 39.78 |
|  | 7.99 | 13.67 | 12.64 | 11.62 |
|  | 7.81 | 6.93 | 4.61 | 3.70 |
| 2 | 8.43 | 1.17 | 1.06 | 1.38 |
|  | 8.26 | 8.97 | 8.15 | 8.38 |
|  | 8.09 | 45.46 | 40.27 | 39.95 |
|  | 7.87 | 13.37 | 16.45 | 6.77 |
|  | 7.72 | 5.47 | 5.39 | 9.55 |
|  | 7.56 | 1.64 | 1.52 | 3.33 |
| 3 | 8.36 | 0.80 | 0.74 | 0.61 |
|  | 8.16 | 6.02 | 6.03 | 7.30 |
|  | 7.98 | 35.60 | 35.58 | 37.24 |
|  | 7.83 | 11.75 | 14.10 | 13.15 |
|  | 7.64 | 2.17 | 4.78 | 2.00 |
|  | 7.51 | 1.23 | 1.81 |  |
| 4 | 8.40 | 0.82 | 0.74 | 0.30 |
|  | 8.22 | 7.87 | 7.38 | 6.29 |
|  | 8.04 | 42.46 | 34.42 | 35.89 |
|  | 7.89 | 14.44 | 13.71 | 11.34 |
|  | 7.71 | 3.18 | 3.31 | 2.69 |
|  | 7.56 | 0.98 | 0.95 |  |
| 5 | 8.42 | 0.82 |  | 1.02 |
|  | 8.25 | 7.22 |  | 5.09 |
|  | 8.07 | 34.68 |  | 28.99 |
|  | 7.91 | 2.67 |  | 3.63 |
|  | 7.86 | 10.63 |  | 7.83 |
|  | 7.72 | 2.52 |  | 2.05 |
| 6 | 8.42 | 1.17 | 1.28 | 1.22 |
|  | 8.23 | 9.88 | 8.56 | 7.90 |
|  | 8.09 | 45.26 | 40.45 | 40.80 |
|  | 7.94 | 13.23 | 16.50 | 13.28 |
| 7 | 8.59 | 1.79 | 1.45 | 1.90 |
|  | 8.45 | 11.74 | 11.32 | 11.51 |
|  | 8.28 | 59.90 | 61.63 | 56.22 |
|  | 8.05 | 20.34 | 19.49 | 22.98 |
|  | 7.92 | 6.24 | 6.11 | 7.39 |
| 8 | 8.58 | 1.59 | 2.94 | 1.38 |
|  | 8.44 | 11.86 | 12.83 | 12.12 |
|  | 8.26 | 61.08 | 60.20 | 63.05 |
|  | 8.05 | 20.21 | 24.03 | 23.45 |
|  | 7.88 | 5.25 |  | 6.55 |
| 9 | 8.61 | 1.22 | 1.42 | 1.21 |
|  | 8.48 | 12.47 | 12.36 | 11.00 |
|  | 8.33 | 56.64 | 54.59 | 55.34 |
|  | 8.10 | 23.37 | 23.81 | 25.31 |
|  | 7.94 | 6.30 | 7.83 |  |

Results of Block H

The pH stability of these formulations was acceptable (<0.1 units), except for Formulations 4 and 5. These are the buffer-free formulations using Gly and Arg as the stabilizers (Table H-1). There was also a slight rise in pH for Formulation 1 (the Humira® formulation at 100 mg/ml protein concentration).

Stability of Block H formulations was monitored using SEC and RP HPLC. There is little loss in monomer content, with Formulation 1 appearing to be the least stable by SEC (Table H-2). At 100 mg/ml of adalimumab biosimilar API the histidine-buffered formulation containing Gly and Arg appears to be quite stable. In general, the best buffer combination appears to be His-succinate (Formulations 7 and 12). Buffer-free formulations with Gly and Arg show acceptable stability as well (Table H-2). The RP HPLC data indicate that the buffer-free formulations (4 and 5) may not do quite as well as shown by SEC (Table H-3), with measurable decreases in purity, but are believed to be satisfactory for obtaining a formulation having long term stability.

The CE-SDS data detect the least change in Formulation 12, which is a His-succinate formulation (Table H-4). The largest change at t1 occurs with Formulation 7, which is also a His-succinate formulation, but using mannitol and NaCl as the tonicity modifiers.

PLS Modeling

PLS Method

The data for the adalimumab formulations in Blocks A through H were analyzed together using a chemometric method termed partial least squares (PLS).

Detailed descriptions of PLS modeling have been published. See, for example, Katz, M. H. *Multivariate Analysis: A Practice Guide for Clinicians*. Cambridge University Press, New York, pp. 158-162 (1999); Stahle, L., Wold, K., Multivariate data analysis and experimental design in biomedical research. *Prog. Med. Chem.* 1988, 25: 291-338; Wold S. PLS-regression: a basic tool of chemometrics. *Chemom. Intell. Lab. Syst.* 2001, 58: 109-130; and Martens, H.; Martens, M. *Multivariate Analysis of Quality: An Introduction*, Wiley and Sons, Chichester, UK (2001).

For any large matrix of values, where there are a reasonable number of samples (together forming the so-called X-matrix), mathematical models can be constructed that explain the largest amount of variance in the dependent variable(s) of interest (the Y-matrix). The best single description of the relationship between the variation in the X-matrix and the endpoint (the Y matrix) is called the first principal component, PC1. The next important (in terms of describing the variance in the Y-matrix) component is called the second principal component, PC2, and so on. Quite often, only one or two PCs are required to explain most of the variance in the Y-matrix. Each of these PCs contains some contribution from each of the variables in the X-matrix. If a variable within the X-matrix contributes heavily to the construction of a given PC, then it is ranked as being significant. In fact, regression coefficients can be calculated for each variable in the X-matrix for a given model, where a model is the composite of a certain number of PCs in order to provide an adequate description of the Y-matrix. In summary, PLS takes information from the X-matrix, calculates the desired number of PCs, and constructs a suitable model. The model that includes all of the samples is termed a calibration model [1,2]. The overall coefficient of determination ($r^2$) indicates the quality of the model. All PLS calculations were conducted using Unscrambler® software (CAMO, Corvallis, Oreg.). A PLS analysis done with a single variable in the Y-matrix is termed PLS1 analysis. Building a model that fits multiple variables in the Y-matrix is called PLS2 analysis.

A full cross validation was performed on all calibration models using standard techniques. Briefly, one sample is removed at a time, the data set is recalibrated, and a new model is constructed. This process is repeated until all of the calibration samples are removed once and quantified as a validation model. Therefore, the first set, containing all samples is referred to as the calibration set and the one after cross-validation as the validation set. The jack-knife algorithm (See, Martens et al) was used to determine statistical significance for any factor used in constructing the PLS models described above.

PLS Modeling of Adalimumab Formulations (Blocks B, C and D)

See FIGS. 3 Through 12

Note: The PLS surface graphs depicted in FIGS. 3 through 12 are based on the data obtained from Blocks B, C and D. The following is a discussion of the findings reflected in the PLS surface plots shown in FIGS. 3 through 12.

Figure 3:
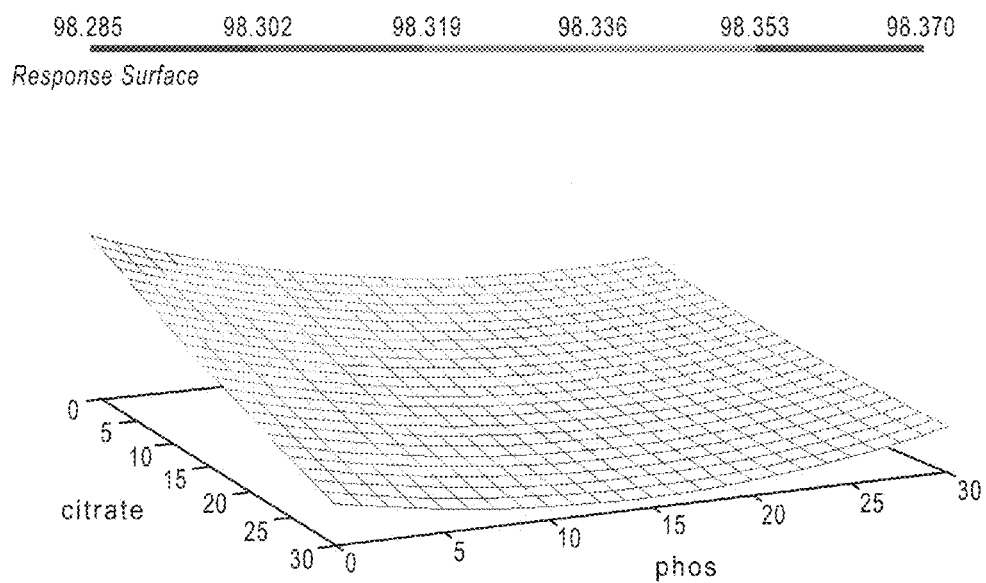
FIG. 3 is a graph of a partial least squares (PLS) model 1 demonstrating effect of citrate/phosphate on stability.

PLS Model 1—FIG. 3.

FIG. 3 contains a depiction of the monomer content at t1 (model 1) as a function of citrate and phosphate concentrations. The pH has been fixed at 5.2. The model indicated that phosphate and citrate by themselves were weak destabilizers (not to statistical significance), along with tartrate and maleate. By comparison, succinate, which is structurally similar to citrate, tartrate and maleate, was a weak stabilizer. The only buffer found to be a significant stabilizer was histidine. None of these findings could have been predicted based on the literature or examination of the chemical structure of each buffer. The model also indicated that when citrate and phosphate buffer are used together, the formulation is least stable. If one only uses a single buffer, especially phosphate, stability improves. This is surprising, as phosphate has little or no buffer capacity at pH 5.2, while citrate buffer does. None of this behavior could have been predicted based on what was known in the art.

Figure 4:
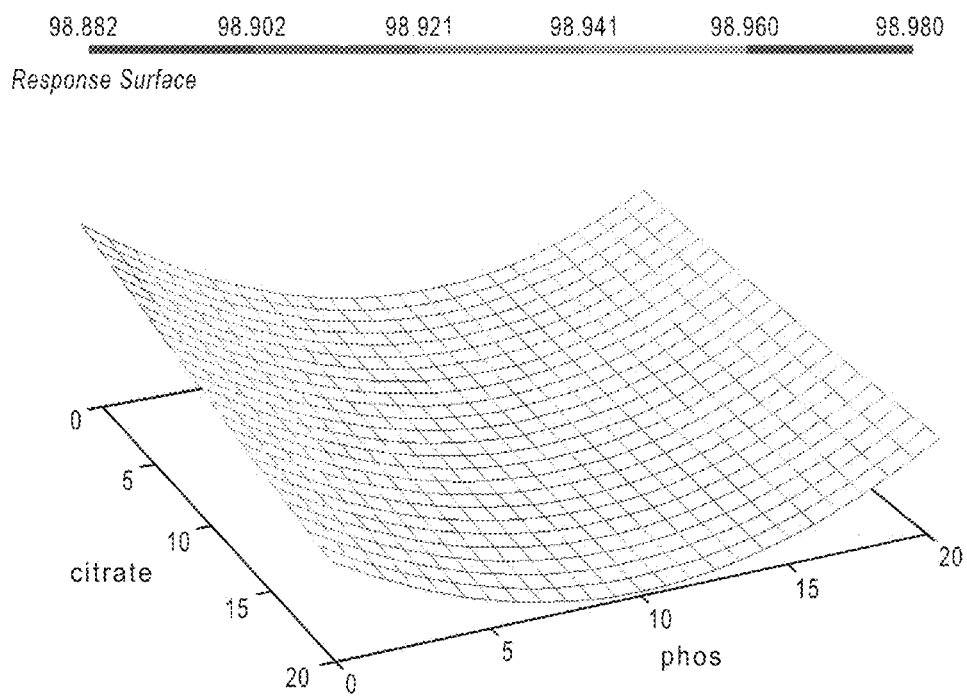
FIG. 4 is a graph of a PLS model 2 demonstrating effect of citrate/phosphate on stability.

PLS Model 2—FIG. 4.

FIG. 4 contains a depiction of the monomer content at t2 (model 2). Likewise, a model was constructed using the monomer content by SEC at t2 as the endpoint. This model also demonstrated that the stability is lowest when citrate and phosphate are used together. The lowest stability was shown when citrate is above 10 mM and phosphate is between 5 and 15 mM. Stability improves when the citrate concentration is lowered and/or phosphate concentration is lowered or raised. These findings suggest that a single buffer composition is preferred. The same trend in buffer stabilization is seen as with PLS Model 1, with citrate and phosphate being weak stabilizers (not statistically significant), while histidine is a strong stabilizer (statistically significant).

Figure 5:
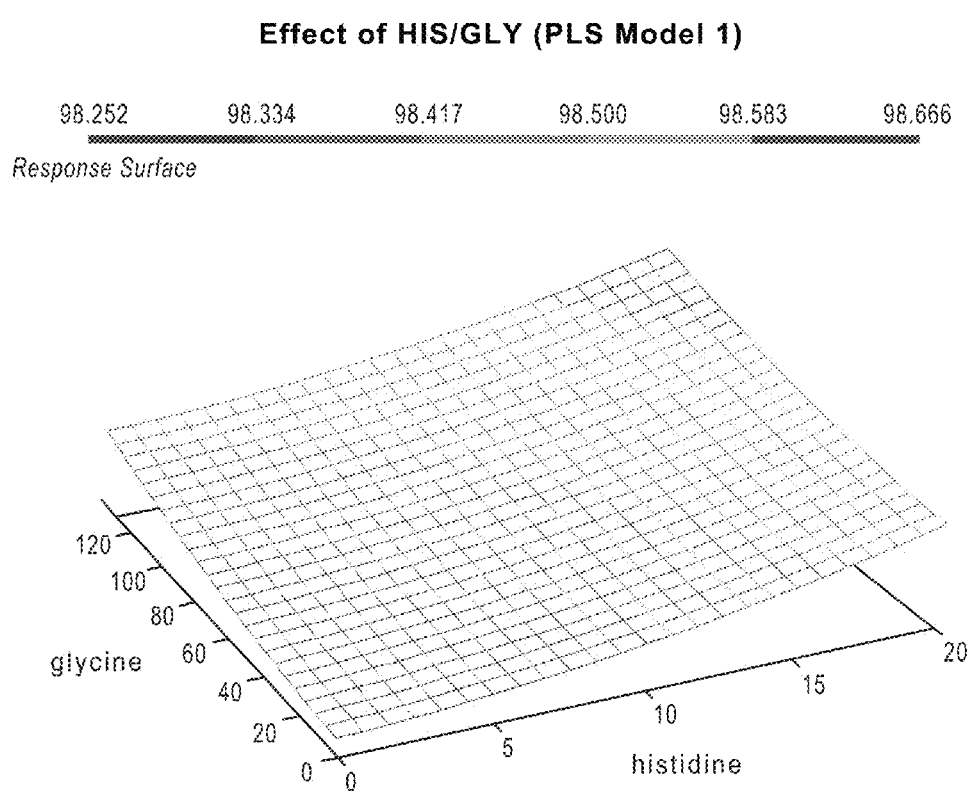
FIG. 5 is a graph of a PLS model 1 demonstrating effect of histidine/glycine on stability.

PLS Model 1—FIG. 5.

FIG. 5 is a PLS model 1 showing the effect of histidine and glycine on the stability of formulations. It contains a depiction of the monomer content at t1 (model 1). This model indicated that the combination of histidine and glycine yielded very good stability results. Both histidine (His) and glycine (Gly) were determined to be stabilizers. The lowest stability on the response surface (shown in blue) is when there is the lowest concentration of His and Gly. The effect of His on stability is greater, with 20 mM His providing comparable stabilization to 120 mM Gly (note the opposite corners of the graph). The model indicates that there will be an additive benefit to stability by using both excipients, with the highest stability occurring when the His concentration is 20 mM and the Gly concentration is 120 mM.

Figure 6:
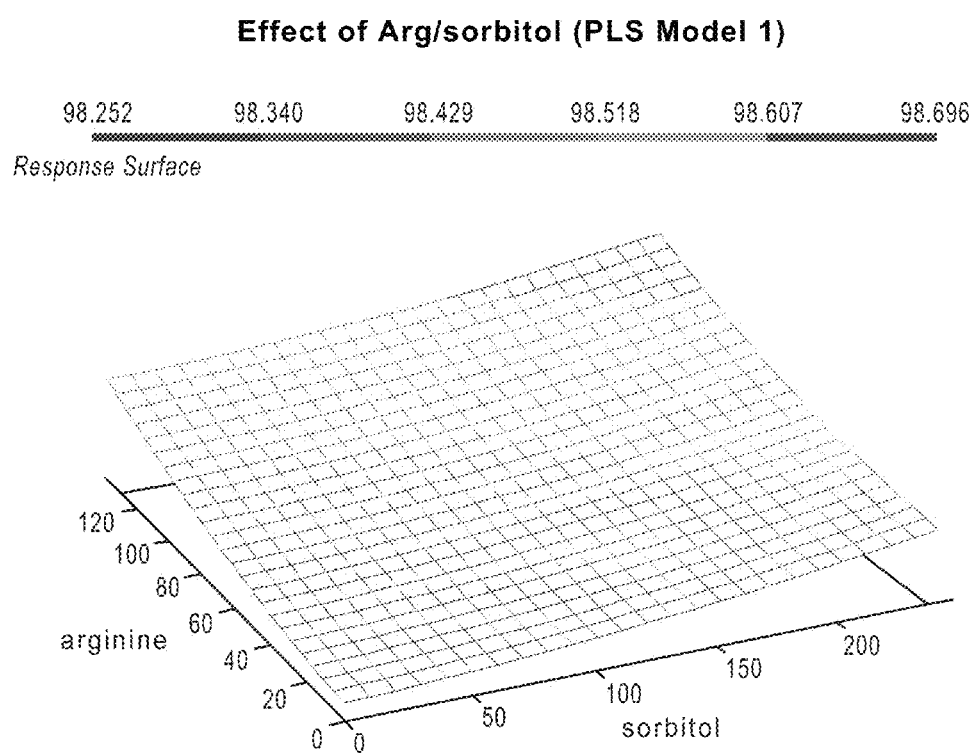
FIG. 6 is a graph of a PLS model 1 demonstrating effect of arginine/sorbitol on stability.

PLS Model 1—FIG. 6.

FIG. 6 is a PLS model 1 showing the effect of arginine and sorbitol on the stability of formulations. It contains a depiction of the monomer content at t1 (model 1). This model indicated that arginine was a good stabilizer, while sorbitol was a poor stabilizer. Likewise, arginine (Arg) provides a degree of stabilization that is similar to that found for Gly. The poorest stability as indicated by this model is when the Arg concentration is low and the sorbitol concentration is low (the blue area of the graph). As the concentrations of each excipient are increased, the monomer content at t1 is increased. The effect of sorbitol is roughly linear with concentration, while the effect of Arg appears to be increasing more rapidly once the concentration exceeds 60 mM. Even though sorbitol is predicted to increase the stability of adalimumab in terms of retained monomer content, its ability to increase stability is less than that found for Gly and Arg (on a molar basis).

Figure 7:
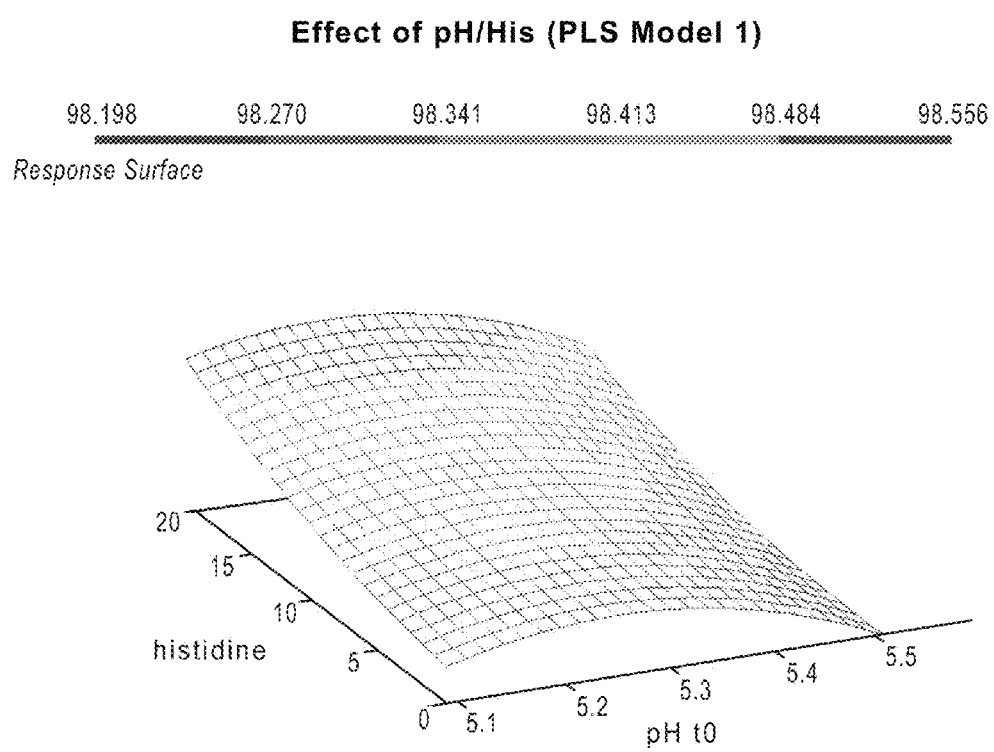
FIG. 7 is a graph of a PLS model 1 demonstrating effect of pH/histidine on stability.

PLS Model 1—FIG. 7.

FIG. 7 is a PLS model 1 showing the effect of pH and histidine on the stability of formulations. It contains a depiction of the monomer content at t1 (model 1). This model indicated that histidine appears to be the best buffer, while pH should preferably be at 5 or higher for best stability.

Figure 8:
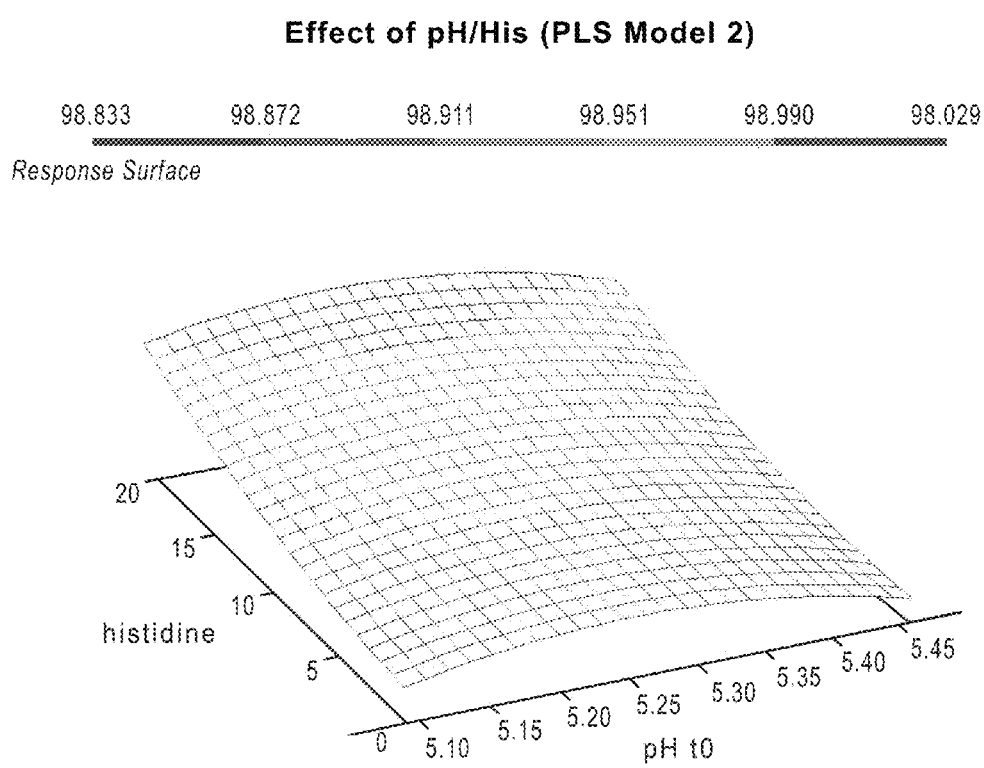
FIG. 8 is a graph of a PLS model 2 demonstrating effect of pH/histidine on stability.

PLS Model 2—FIG. 8.

FIG. 8 is a PLS model 2 showing the effect of pH and histidine on the stability of formulations. It contains a depiction of the monomer content at t2 (model 2). This model indicated that histidine appears to be the best buffer, while pH should preferably be at 5 or higher for best stability. The results indicate that the optimal pH is near 5.2. Of all of the buffers that were examined, histidine provides the greatest degree of stabilization. This response surface illustrates two important points. First, the stability appears to be maximal near pH 5.2, falling off at a higher and lower pH. Second, histidine is shown to provide a significant increase in stability. When histidine is used at 20 mM, it provides a marked increase in stability over lower buffer concentrations. In fact, the effect appears to be non-linear, with more stabilization occurring from 10 to 20 mM than from 0 to 10 mM. Further, the loss in stability is more abrupt at higher pH than at lower pH.

Figure 9:
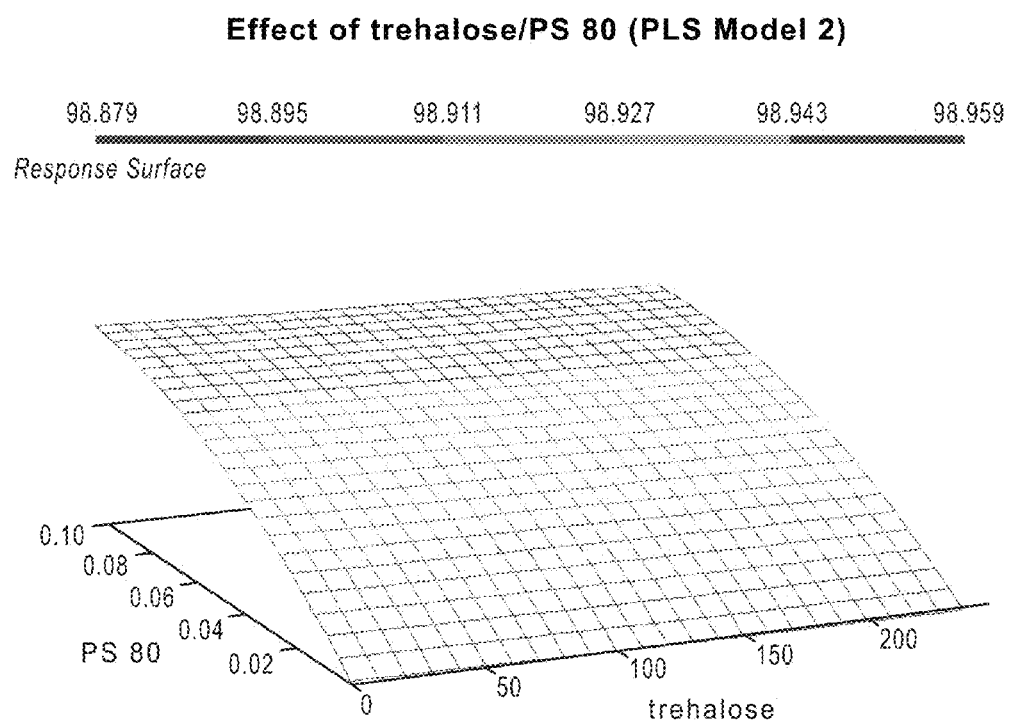
FIG. 9 is a graph of a PLS model 2 demonstrating effect of trehalose/PS80 on stability.

PLS Model 2—FIG. 9.

FIG. 9 is a PLS model 2 showing the effect of trehalose and PS80 on the stability of formulations. It contains a depiction of the monomer content at t2. This model indicated that trehalose appears to be a weak stabilizer, while PS80 improves thermal stability. The response surface shown in FIG. 9 indicates that PS 80 is a potent stabilizer for protecting adalimumab against thermal stress, with a concentration of 0.1% providing maximal stability. The concentration of PS 80 has not been varied other than at 0 and 0.1%. By comparison, this model shows that the stabilization effect of trehalose is quite small, certainly less than what was seen with sorbitol.

Figure 10:
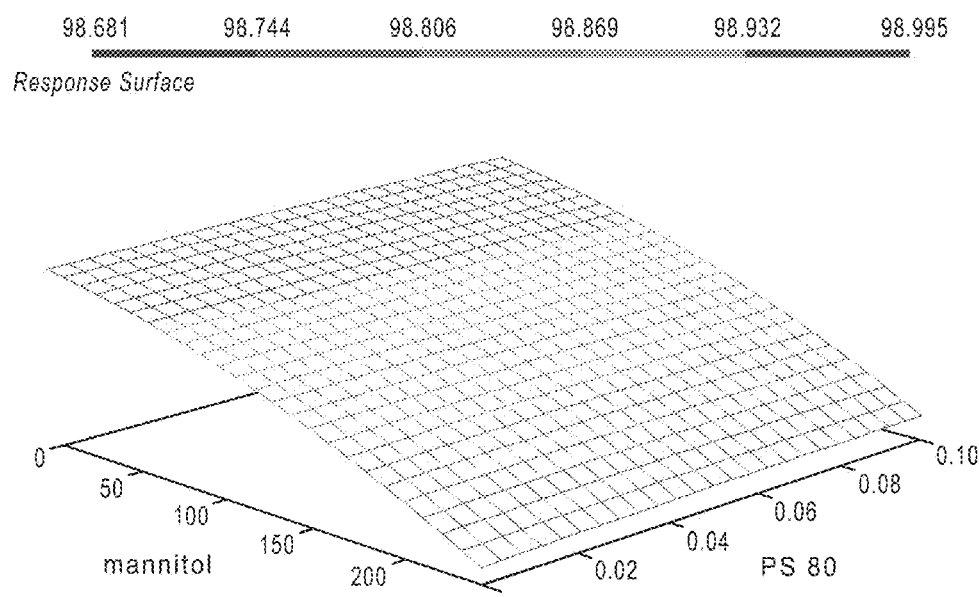
FIG. 10 is a graph of a PLS model 2 demonstrating effect of mannitol/PS80 on stability.

PLS Model 2—FIG. 10.

FIG. 10 is a PLS model 2 showing the effect of mannitol and PS80 on the stability of formulations. It contains a depiction of the monomer content at t2 (model 2). This model indicated that mannitol appears to be a destabilizer, while PS80 improves thermal stability. The PLS model using monomer content by SEC at t2 allows one to examine the relative effects of any of the factors included in the model. As the mannitol concentration increases, the overall stability decreases. By comparison, the impact of PS80 on the stability is rather small.

Figure 11:
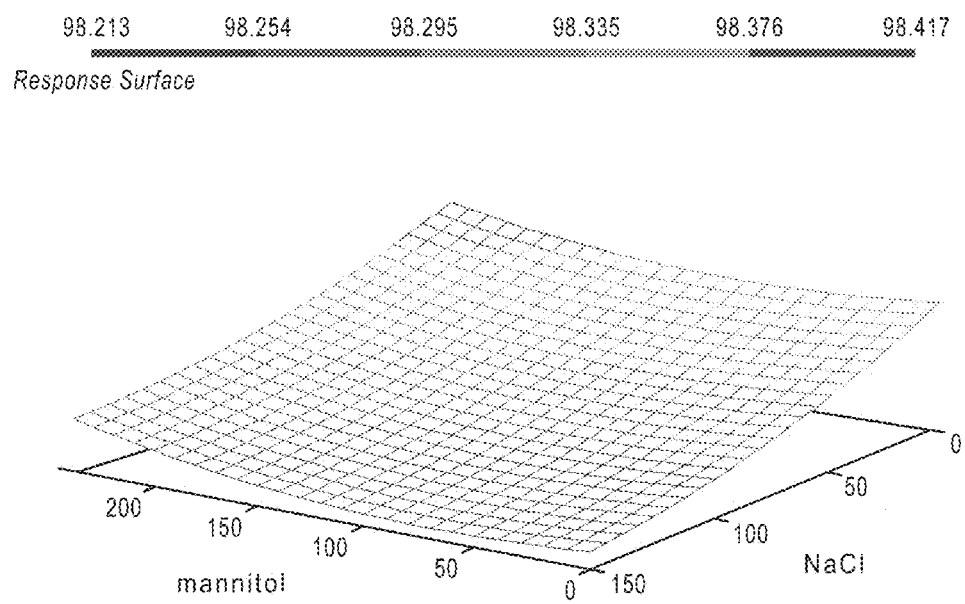
FIG. 11 is a graph of a PLS model 1 demonstrating effect of mannitol/NaCl on stability.

PLS Model 1—FIG. 11.

FIG. 11 is a PLS model 1 showing the effect of mannitol and NaCl on the stability of formulations. It contains a depiction of the monomer content at t1 (model 1). This model indicated that mannitol and NaCl both appear to be destabilizers. The stability, as indicated by the monomer content at t1, is lowest when the mannitol concentration is anywhere below 150 mM. Likewise, addition of NaCl also diminishes the stability of adalimumab.

Figure 12:
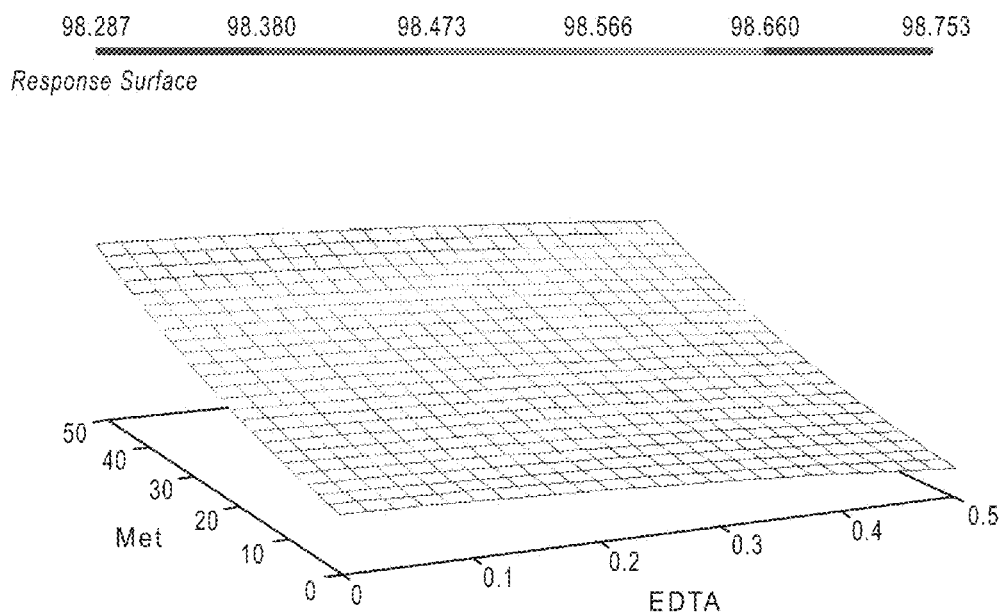
FIG. 12 is a graph of a PLS model 1 demonstrating effect of EDTA/methionine on stability.

PLS Model 1—FIG. 12.

FIG. 12 is a PLS model 1 showing the effect of EDTA and methionine on the stability of formulations. It contains a depiction of the monomer content at t1. In the case of EDTA, the stability decreases slightly as the concentration of this additive increases. In contrast, addition, of Met appears to improve stability.

PLS Modeling of Adalimumab Formulations for Blocks B Through G

See FIGS. 13 Through 28

The First PLS Model ("PLS Model A)

The first PLS model (PLS Model A) used difference in monomer content at t1 as the endpoint. The model employed three PCs and had a correlation coefficient for the calibration set of 0.83 and a r-value of 0.67 for the validation set. It was a quadratic model including pH-buffer and buffer-buffer interaction terms.

TABLE J

PLS "MODEL A" COEFFICIENTS

| Factor | r-value |
| --- | --- |
| pH t0 | 0.041 |
| protein | −0.025 |
| citrate | +0.123 |
| phos | +0.267 |
| succinate | −0.089 |
| histidine | −0.174 |
| acetate | −0.053 |
| glycine | −0.190 |
| arginine | −0.128 |
| sorbitol | −0.003 |
| trehalose | +0.020 |
| mannitol | −0.104 |
| NaCl | +0.250 |
| F68 | +0.018 |
| PS 20 | +0.021 |
| PS 80 | −0.152 |
| EDTA | +0.112 |
| Met | −0.062 |

Note:
Overall correlation coefficients for each linear factor includes in the first PLS model (PLS Model A) using the difference in monomer content by SEC at t1 as the endpoint. Factors deemed to be statistically significant are highlighted in bold text.

The model quality is acceptable, considering the correlation coefficients of the calibration and validation sets. The overall correlation coefficients for the various factors included in the model are summarized in Table J. Note that the quadratic and interaction terms are not listed here. As the endpoint is the difference in monomer content, one wishes to minimize this value. Thus, stabilizers exhibit negative correlation coefficients, while destabilizers have positive r-values. Of the stabilizers, His, Gly, Arg, and PS 80 are the most potent, although mannitol and succinate also have a stabilizing effect (Table J). Meanwhile, there are some significant destabilizers, such as NaCl, citrate, and phosphate. Keep in mind that these models are a composite of all of the stability data gathered across the various blocks of formulations, A through H, and individual formulations could vary from the model. While the table of correlation coefficients is helpful to gauge the effects of various factors, they do not capture the non-linear and interaction effects, so it is helpful to view response surfaces to examine the effects of various parameters in greater detail, as shown in the response surfaces that are reproduced in FIGS. 13 through 28.

Figure 13:
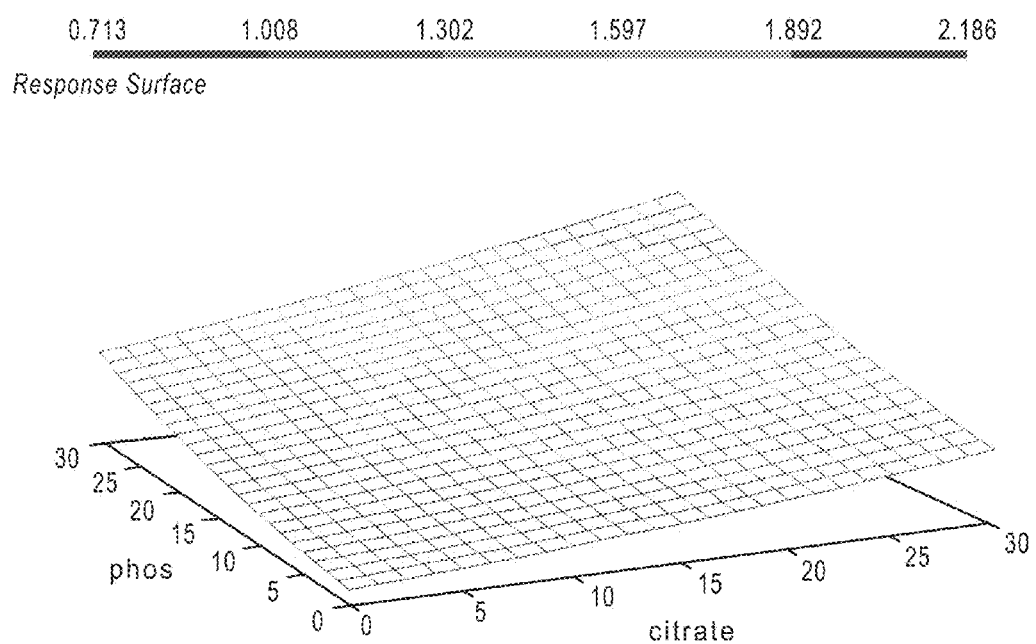
FIG. 13 is a graph of a PLS model A demonstrating effect of citrate and phosphate on stability.
Figure 14:
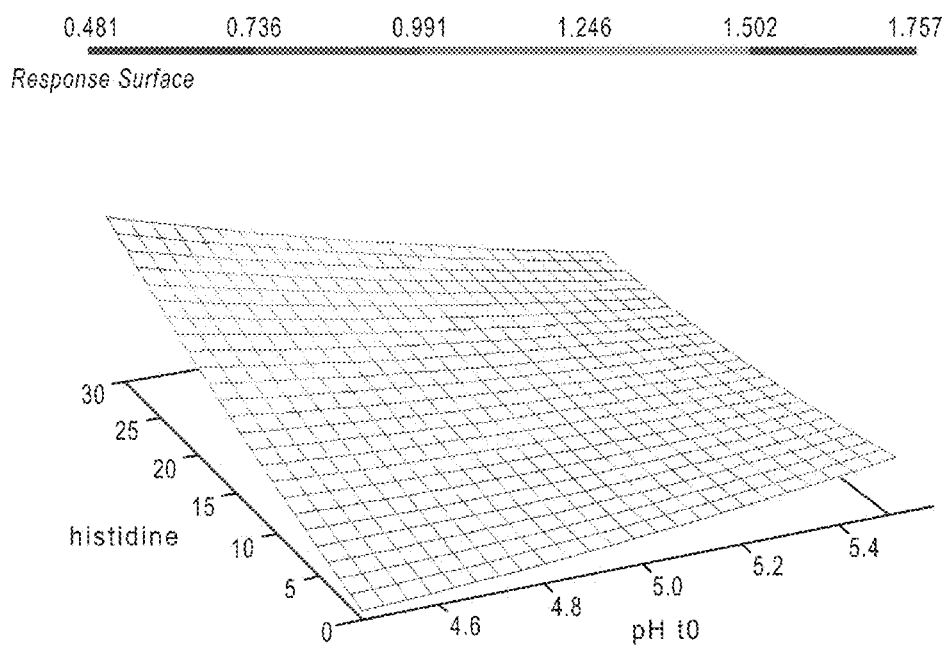
FIG. 14 is a graph of a PLS model A demonstrating effect of pH and histidine buffer on stability.

Discussion of PLS Model A—FIGS. 13 and 14.

The Krause '583 patent describes the citrate-phosphate buffer system as being integral to product stability. Our studies show this not to be the case. The poorest stability would occur when these two buffers were used in combination and the effect would get worse as the buffer concentrations increase, according to this model (FIG. 13). The response surface indicates that the phosphate and citrate are equally destabilizing, contrary to some earlier observations, but the quantitative nature of these surfaces must be considered with some care as they include data from all of the formulations from Blocks B through H.

The effect of pH and His is shown in FIG. 14. It shows that His is destabilizing at low pH, where it is clearly outside of the buffer capacity of His. Again, this result is a function of all pH observations in this study, not just those involving His (although this could be done). According to this response surface, the optimal pH may be nearer to 5.4 than 5.2, although the surface is relatively flat through this region, indicating a shallow response surface from pH 5 to 5.4 (FIG. 14).

Figure 15:
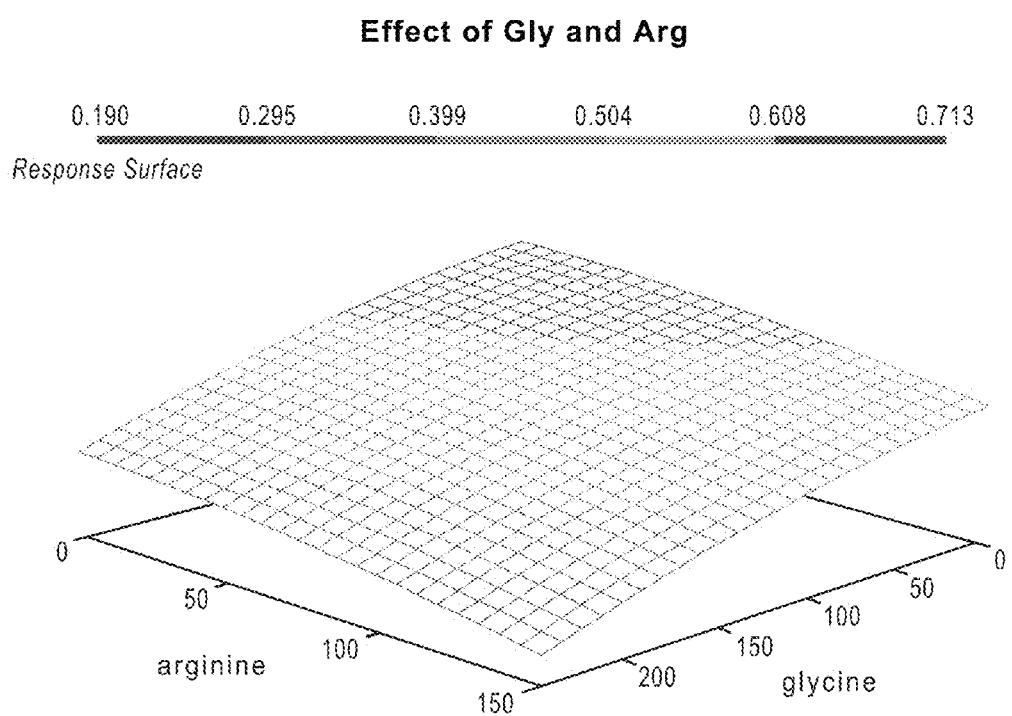
FIG. 15 is a graph of a PLS model A demonstrating effect of glycine and arginine on stability.

Discussion of PLS Model A—FIG. 15

The response surface for Gly and Arg is shown in FIG. 15. The studies repeatedly show that these two amino acids can be potent stabilizers of adalimumab. Note that the minimum difference in monomer content (i.e., the blue part of the surface) is reached at 100 mM Arg, but at 200 mM Gly, suggesting that Arg may be the better stabilizer for adalimumab at pH 5.2.

Figure 16:
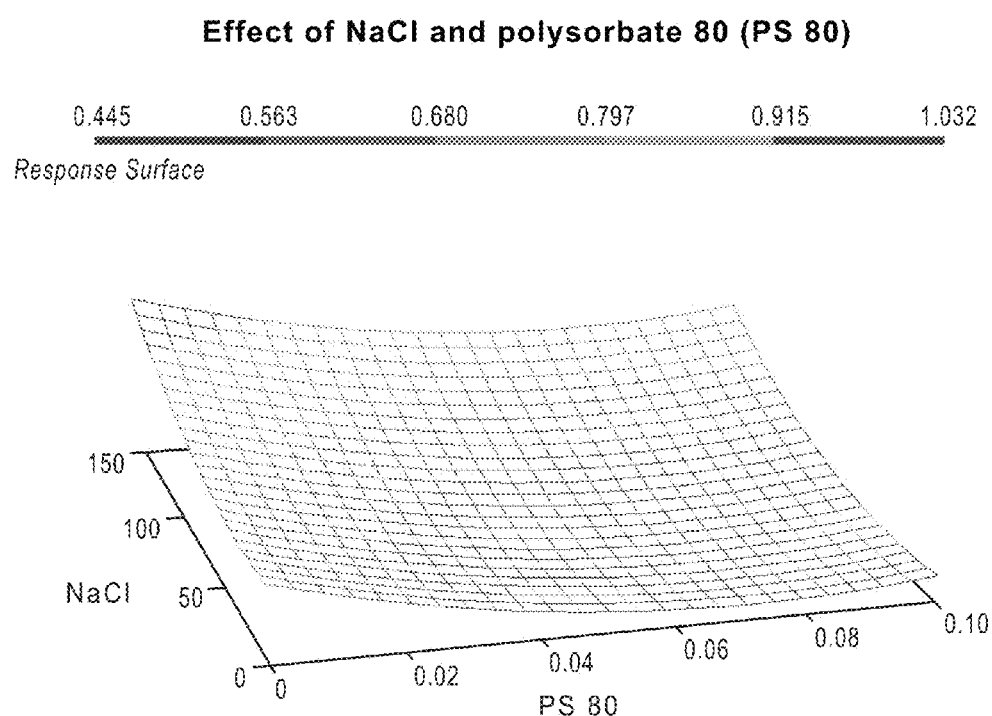
FIG. 16 is a graph of a PLS model A demonstrating effect of NaCl and polysorbate 80 (PS 80) on stability.

Discussion of PLS Model A—FIG. 16

The final response surface shown for PLS Model A is for the effect of NaCl and PS 80 (FIG. 16). It shows that the stability of adalimumab decreases upon addition of NaCl, especially above 100 mM. Meanwhile, PS 20 provides significant stability when used above 0.04%.

The Second PLS Model (PLS Model B)

The second PLS model (PLS Model B) used the monomer content at t1 and at t2 as the endpoints. The model employed four PCs and had a correlation coefficient for the calibration set of 0.82 and a r-value of 0.67 for the validation set. It was a quadratic model including pH-buffer and buffer-buffer interaction terms. In terms of model quality, this is comparable to the first PLS Model A described above.

TABLE K (L)

PLS "MODEL B" CORRELATION COEFFICIENTS

| Factor | r-value |
| --- | --- |
| pH | −0.086 |
| protein | +0.030 |
| citrate | −0.079 |
| phos | −0.157 |
| succinate | +0.060 |
| histidine | +0.185 |
| acetate | +0.063 |
| glycine | +0.126 |
| arginine | +0.150 |
| sorbitol | +0.025 |
| trehalose | +0.006 |
| mannitol | +0.014 |
| NaCl | −0.215 |
| F68 | −0.044 |
| PS 20 | −0.028 |
| PS 80 | +0.227 |
| EDTA | −0.097 |
| Met | +0.096 |

The endpoints for PLS Model B are the total monomer contents at both t1 and t2. Therefore, one will wish to maximize these values. This means that stabilizers with have positive correlation coefficients and destabilizers will display negative r-values (Table K). As with the previous model, citrate, phosphate, and NaCl are significant destabilizers. On the other hand, His, Gly Arg, and PS 20 are potent stabilizers. In this model, trehalose, sorbitol and mannitol have very little effect. The primary differences are that pH is now a significant factor and that EDTA is a significant destabilizer, while Met appears to be a stabilizer as well.

Figure 17:
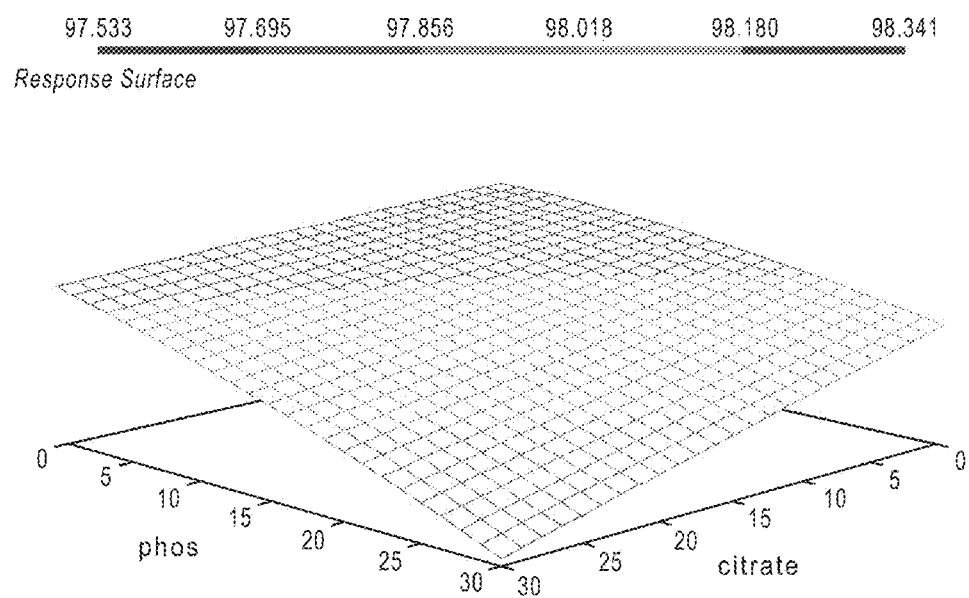
FIG. 17 is a graph of a PLS model B demonstrating effect of citrate and phosphate on stability.

Discussion of PLS Model B—FIG. 17

This model suggests that addition of citrate has little effect on stability if phosphate is absent (view the back edge of the response surface of FIG. 5). On the other hand, added phosphate does decrease monomer content (view the right hand edge) and the combination is even more destabilizing (FIG. 5). Thus, the citrate-phosphate buffer combination is not effective at stabilizing adalimumab, contrary to what is taught by the '583 patent. The destabilizing effect of phosphate is about three-fold greater than for citrate according to this model.

Figure 18:
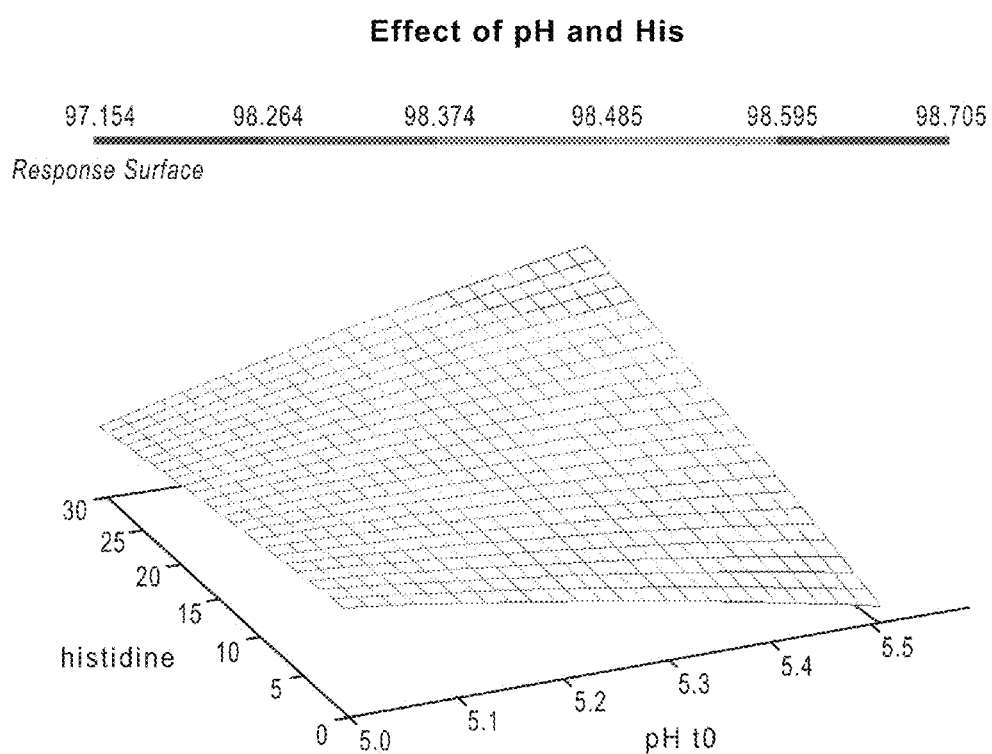
FIG. 18 is a graph of a PLS model B demonstrating effect of pH and histidine buffer on stability.

Discussion of PLS Model B—FIG. 18

The use of His at low pH has little or detrimental effects (FIG. 18[6\]). However, when employed at pH 5.2 or above, the His provides a significant increase in stability (as measured by monomer content by SEC).

Figure 19:
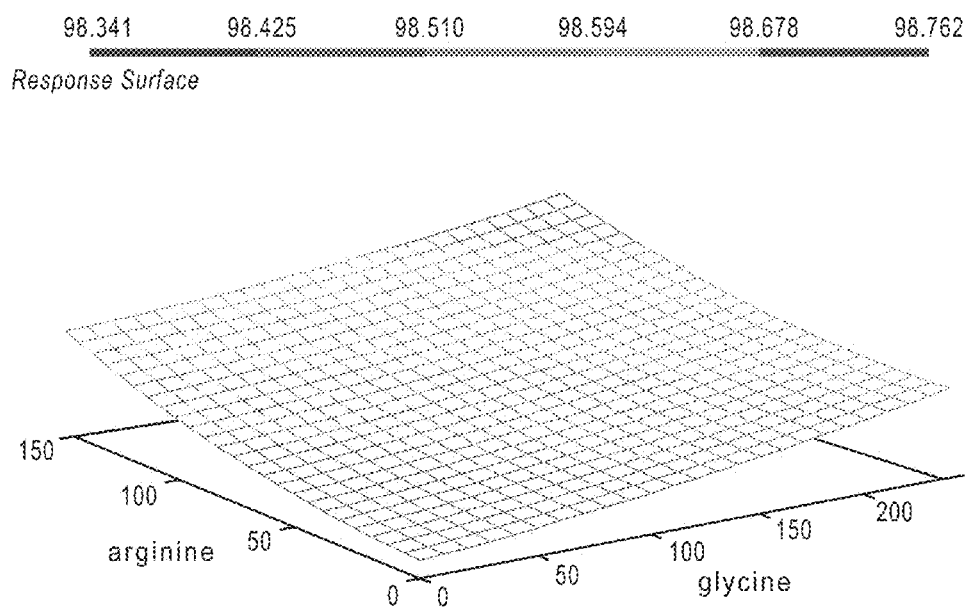
FIG. 19 is a graph of a PLS model B demonstrating effect arginine and glycine on stability.

Discussion of PLS Model B—FIG. 19

The response surface for Gly and Arg is shown in FIG. 19. Including both stabilizers at high concentrations would be beneficial for stability, but impractical for tonicity reasons. It does appear that Arg is the more potent stabilizer in this model compared to Gly, where a 75 mM concentration of Arg has the same effect as ~120 mM Gly. The model indicates either one alone would work well, or that a combination would be effective as well.

Figure 20:
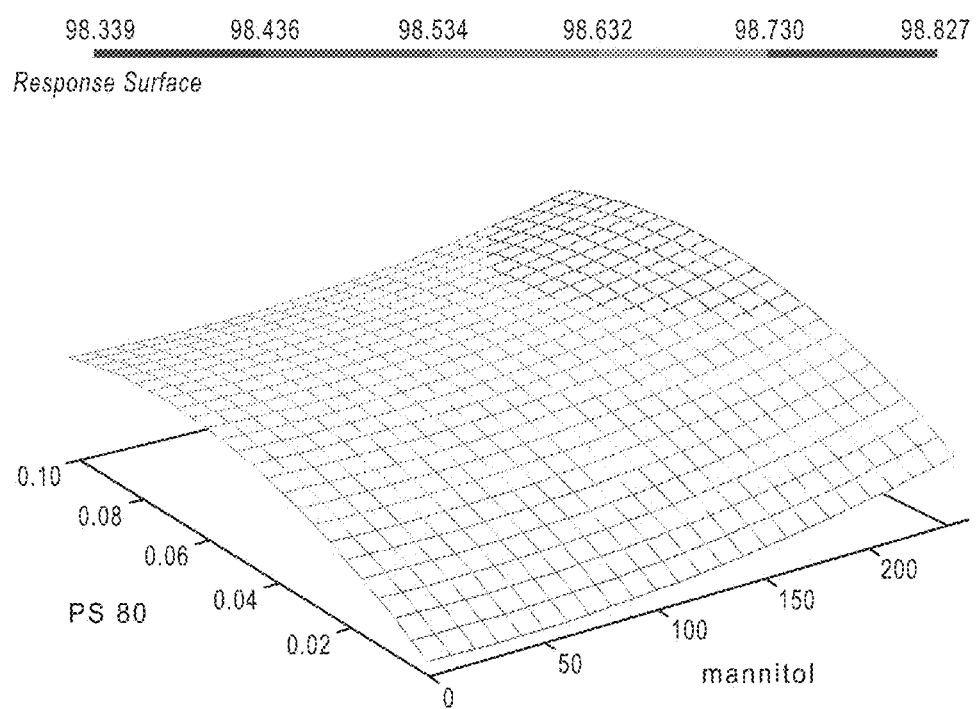
FIG. 20 is a graph of a PLS model B demonstrating effect of PS80 and mannitol on stability.

Discussion of PLS Model B—FIG. 20

The PLS model B shows a modest effect of mannitol on stability, whereas PS 80 is an effective stabilizer above concentrations near 0.05% (FIG. 20). Thus, one could conclude from this data that a stable formulation could be comprised of 240 mM mannitol and 0.1% PS 80 at pH 5.2.

Figure 21:
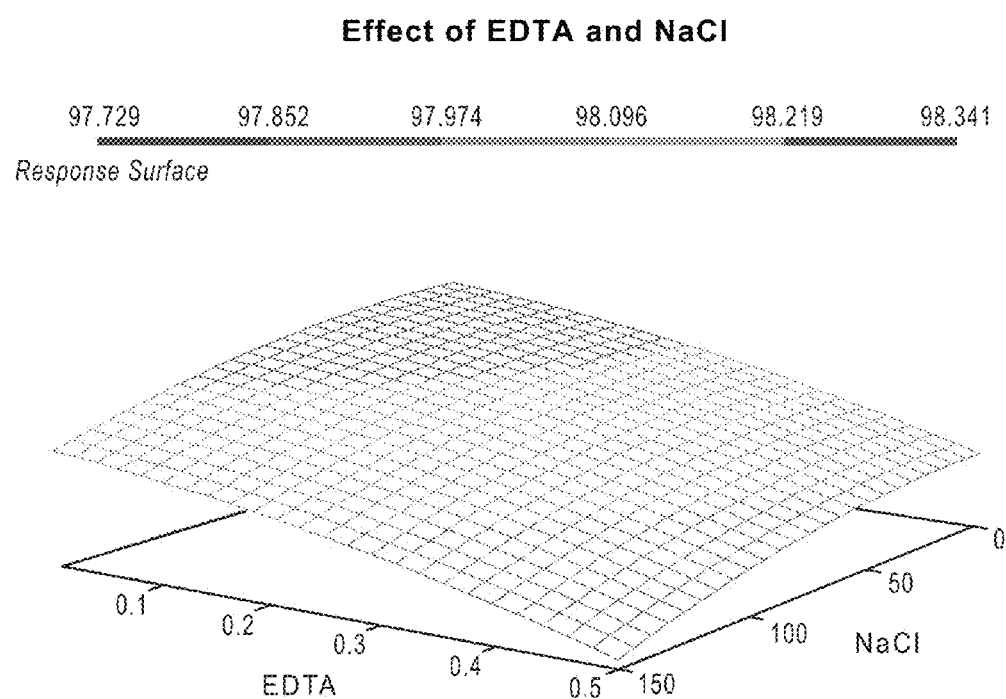
FIG. 21 is a graph of a PLS model B demonstrating effect of EDTA and NaCl on stability.

Discussion of PLS Model B—FIG. 21

Throughout the project, it appears that NaCl is a destabilizer of adalimumab, especially when the concentration reach 100 mM or above, as shown in this response surface (FIG. 21). While only a few formulations were tested that included EDTA, it appears that this excipient is destabilizing, unless the concentration were ~0.1%. We also note that the effect of Met was favorable with respect to stability, but it did not prove to be a significant effect, probably because relatively few examples were evaluated.

Figure 22:
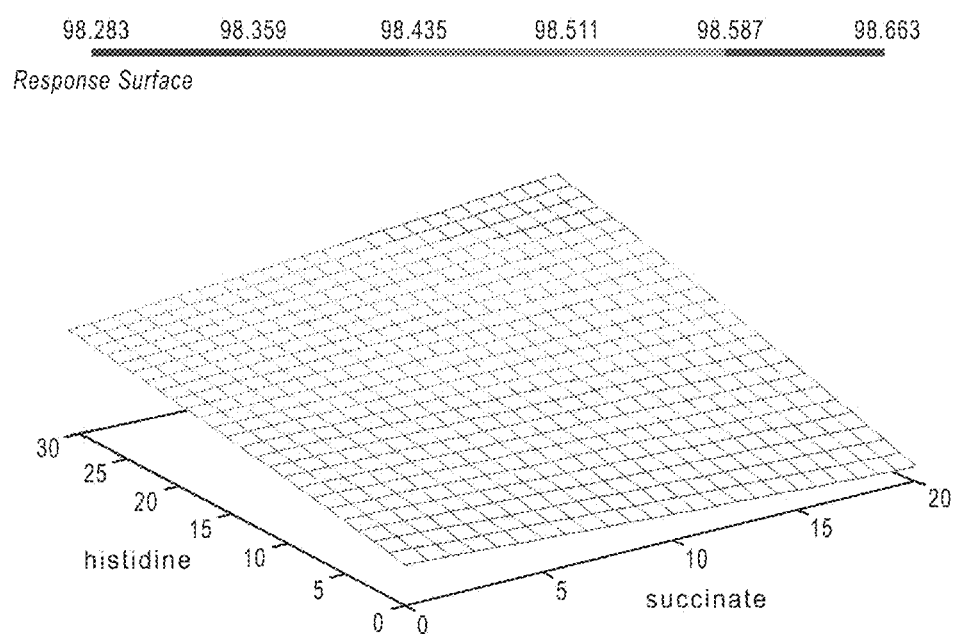
FIG. 22 is a graph of a PLS model B demonstrating effect of succinate buffer and histidine buffer on stability.

Discussion of PLS Model B—FIG. 22

The final response surface from the PLS Model B to be considered is the effect of succinate and His (FIG. 22). The model did include all relevant buffer-buffer interactions. This surface shows that succinate has little or even deleterious effects on its own (see the front edge of the plot). However, in conjunction with His it proves to increase the overall stability (e.g., note that back edge of the surface). Therefore, a His-succinate buffer system appear to be the most favorable of all of the buffer combinations tested to date.

The Third PLS Model (PLS Model C)

The third PLS model C used the difference in percent purity by RP HPLC at t1 as the endpoint. The model employed two PCs and had a correlation coefficient for the calibration set of 0.86 and a r-value of 0.67 for the validation set. It was a quadratic model including pH-buffer and buffer-buffer interaction terms. In terms of model quality, this is very similar to the previous model.

TABLE L

PLS "MODEL C" CORRELATION COEFFICIENTS

| Factor | r-value |
| --- | --- |
| pH | −0.115 |
| protein | −0.139 |
| citrate | +0.014 |
| phosphate | +0.084 |
| succinate | −0.051 |
| histidine | −0.075 |
| acetate | +0.159 |
| glycine | −0.096 |
| arginine | −0.045 |
| sorbitol | +0.029 |
| trehalose | +0.020 |
| mannitol | −0.060 |
| NaCl | +0.068 |
| F68 | −0.047 |
| PS 20 | −0.067 |
| PS 80 | −0.028 |
| EDTA | +0.099 |
| Met | −0.015 |

PLS Model C demonstrates that RP HPLC is stability-indicating, even though the sensitivity may be less than for SEC. The model finds that both phosphate and citrate are destabilizing, with the effect of phosphate being statistically significant (Table LI). Likewise, acetate is a strong destabilizer as is EDTA. Both Gly and Arg are shown to be stabilizers, but the effects are not deemed to be statistically significant. Only His was found to be a significant stabilizer (along with protein concentration).

Figure 23:
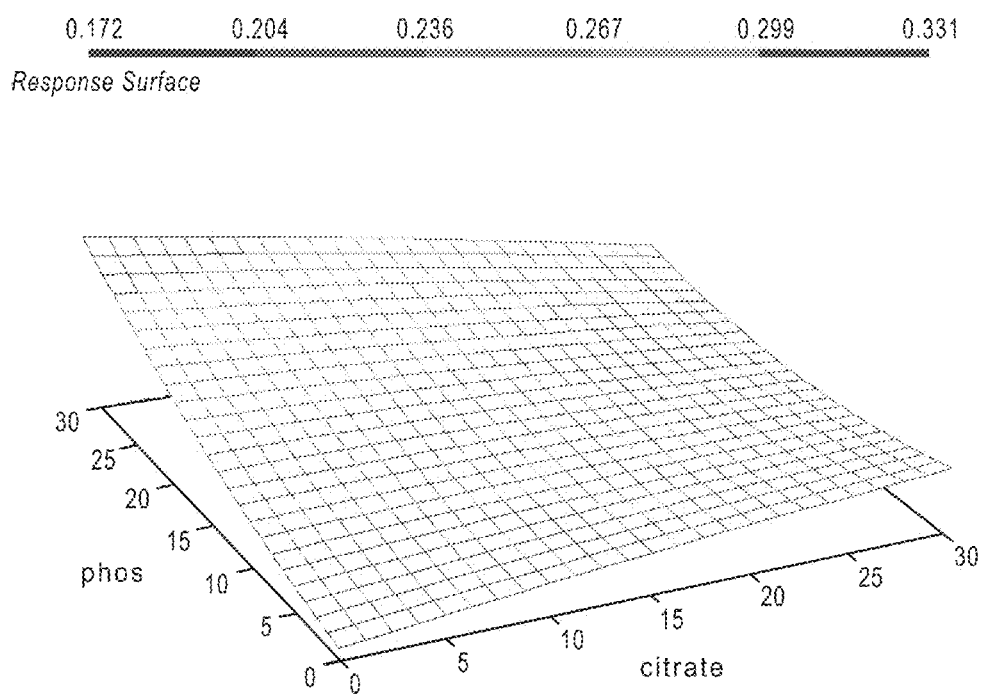
FIG. 23 is a graph of a PLS model C demonstrating effect of citrate and phosphate on stability.

Discussion of PLS Model C—FIG. 23

The response surface for citrate and phosphate at pH 5.2 is shown in FIG. 23. Both buffers are destabilizing (follow the front and left-hand edges of the plot). Above concentrations of ~10 mM, the combination becomes quite destabilizing. Overall, phosphate is predicted to be more destabilizing according to this model (FIG. 11).

Figure 24:
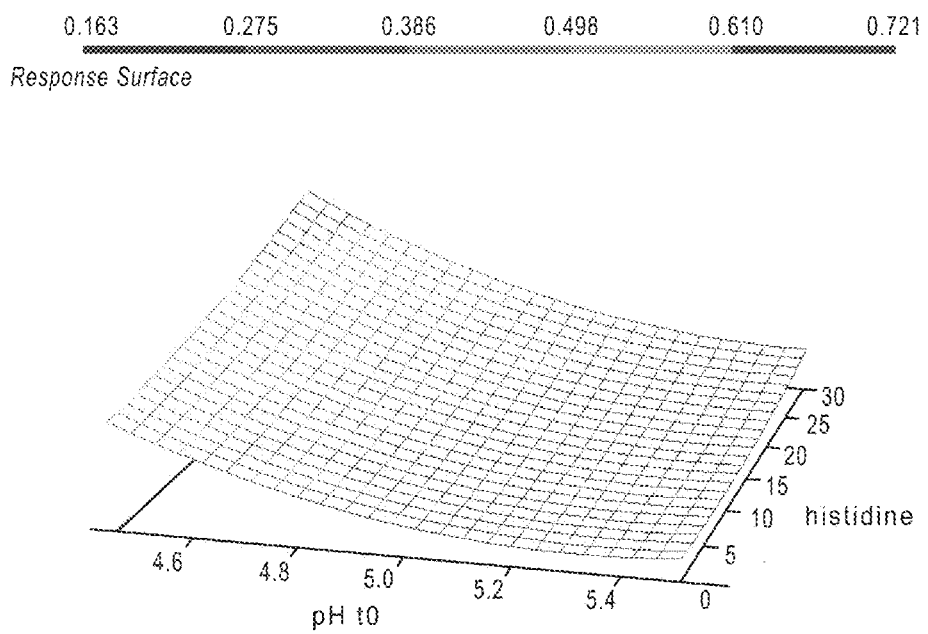
FIG. 24 is a graph of a PLS model C demonstrating effect of pH and histidine buffer on stability.

Discussion of PLS Model C—FIG. 24

As seen in previous models, the stability of adalimumab decreases as the pH is reduced to less than 5.0 (FIG. 12). In this model the stabilizing effect of His is seen across all pH values, but is most pronounced when the pH is lower.

Figure 25:
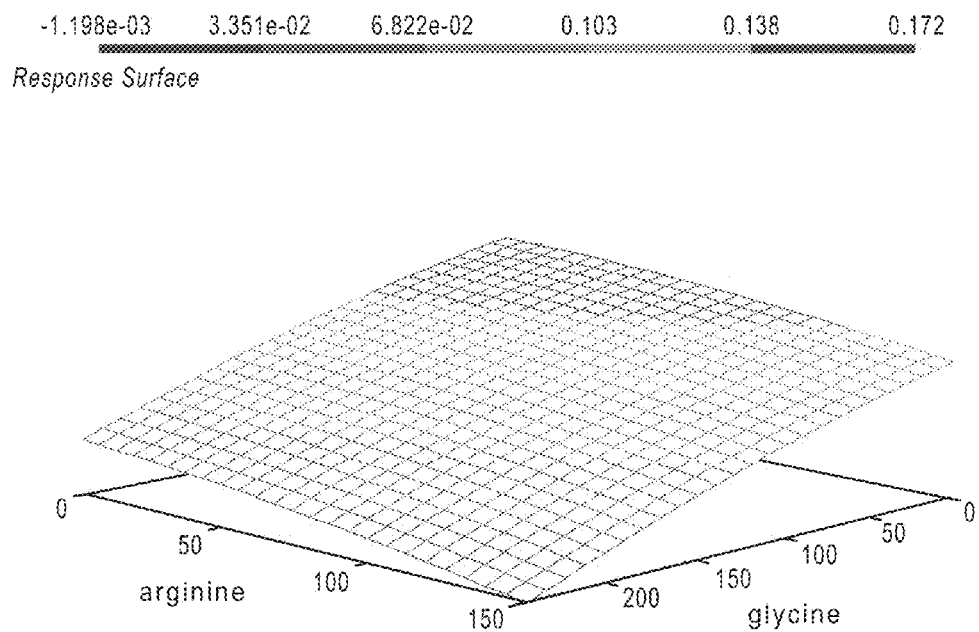
FIG. 25 is a graph of a PLS model C demonstrating effect of arginine and glycine on stability.

Discussion of PLS Model C—FIG. 25

The effects of Gly and Arg are seen in FIG. 25. Both excipients decrease loss of purity as the concentration increases and they are predicted to be roughly equipotent, as judged by the slopes along the edges of the response surface. Otherwise, it appears that it takes less Arg (75 mM) to achieve optimal loss of purity (the blue region of the graph) than for Gly (~200 mM).

Figure 26:
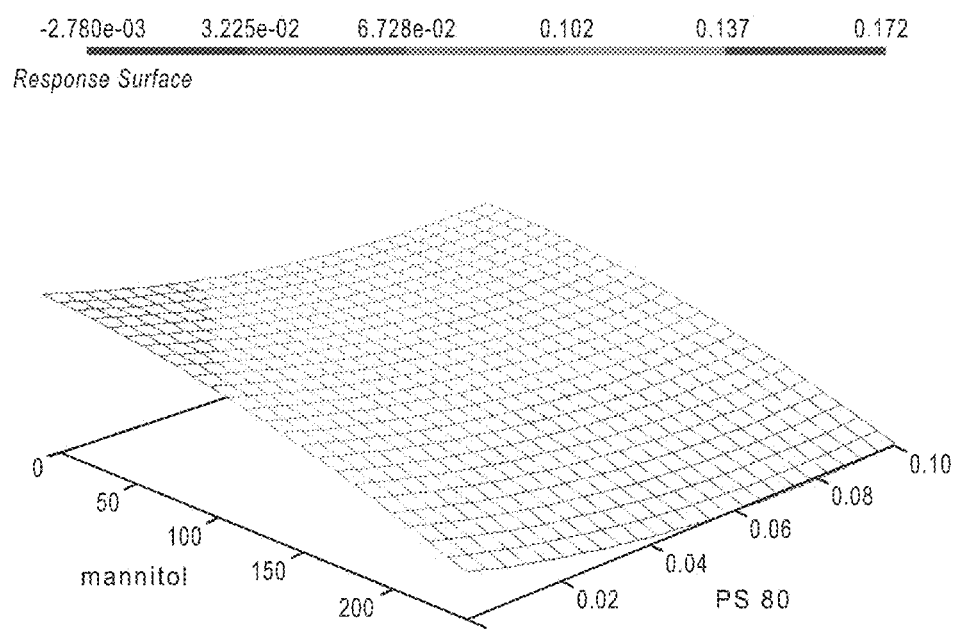
FIG. 26 is a graph of a PLS model C demonstrating effect of mannitol and PS 80 on stability.

Discussion of PLS Model C—FIG. 26

The effect of mannitol and PS 80 is seen in the response surface in FIG. 26. It is clear that chemical stability is greatly improved by adding PS 80, especially at concentrations above 0.04%. Meanwhile, mannitol is also stabilizing, but even 240 mM mannitol has less effect than a small about of the surfactant.

Figure 27:
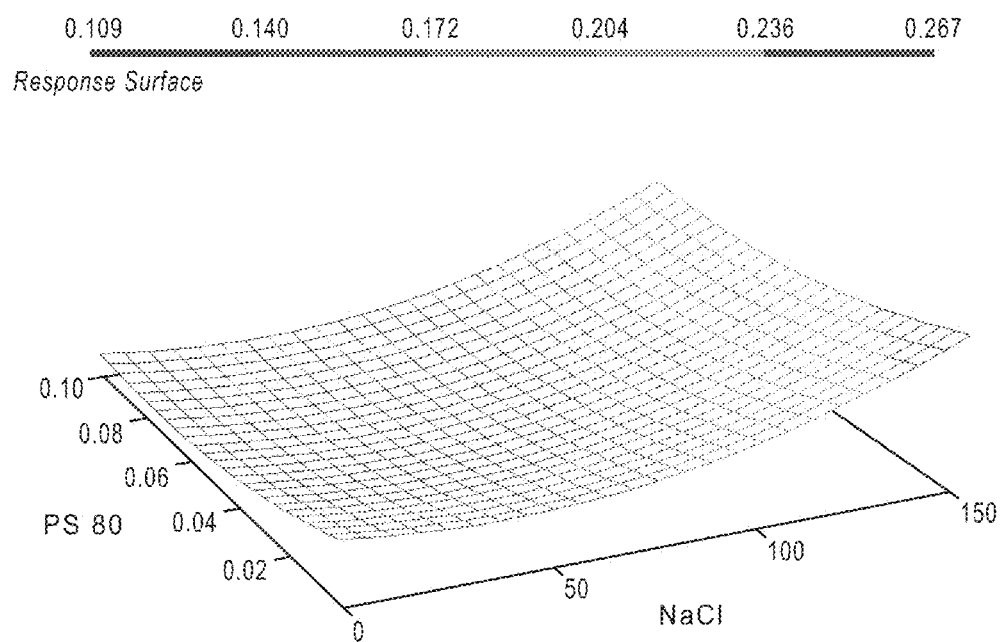
FIG. 27 is a graph of a PLS model C demonstrating effect of PS 80 and NaCl on stability.

Discussion of PLS Model C—FIG. 27

While mannitol is believed to be a stabilizer in the Humira® formulation, NaCl is clearly a destabilizer, both in this model (See FIG. 27), and in previous PLS models. The effect is substantial when the NaCl concentration exceeds 75 mM or so.

Figure 28:
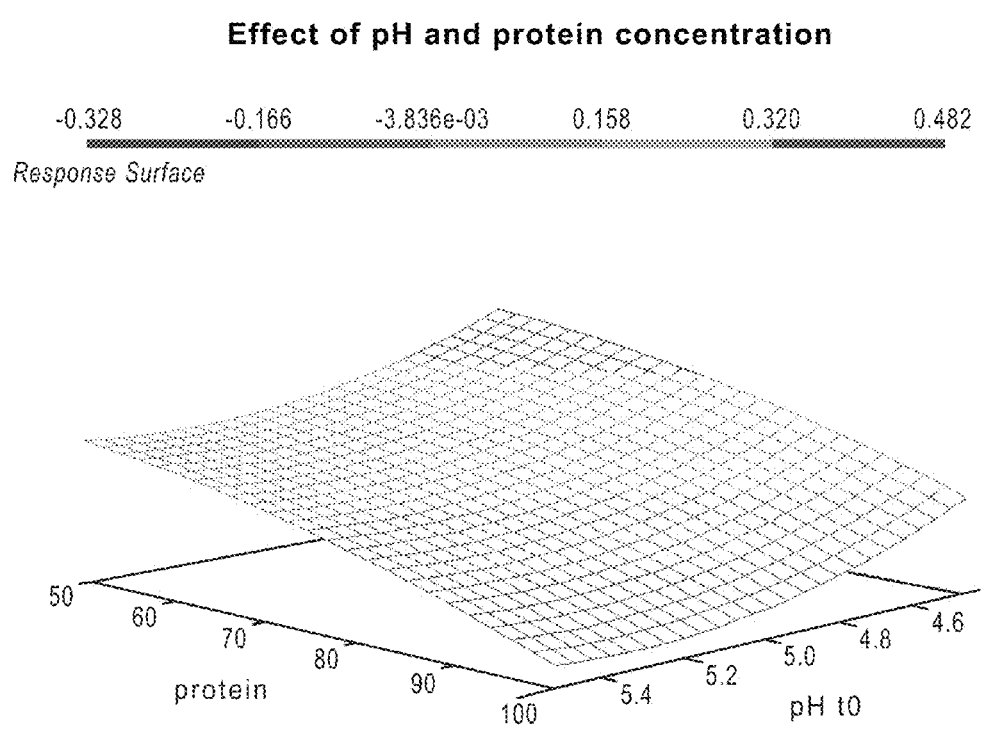
FIG. 28 is a graph of a PLS model C demonstrating effect of pH and protein concentration on stability.

Discussion of PLS Model C—FIG. 28

The final response surface from PLS Model C is seen in FIG. 28 describing the effects of pH and protein concentration. As seen before, the stability is best when the pH is above 4.8 or 5.0. As for the protein effect, this model predicts that the stability, based on RP HPLC, is better at higher protein concentrations. A similar trend, albeit a fairly weak one, was seen for the SEC data (monomer content at t1 and t2). Therefore, it may be possible to achieve similar stability profiles at concentrations at 100 mg/ml as one could obtain at 50 mg/ml.

Summary of Findings for Blocks A Through H

The formulation studies in Blocks A through H evaluated adalimumab formulations stored at elevated temperature and held for either one week at 40° C. or for two weeks at 25° C. The stability was monitored using SEC, RP HPLC, cIEF and CE-SDS.

The optimal pH appears to be 5.2±0.2. Of all of the buffer compositions tested, the citrate-phosphate combination is inferior to nearly any other buffer system evaluated, hence an important aspect of the present invention is the avoidance of this combined buffer system altogether. The best single buffer appears to be His, while a His-succinate buffer also offers very good stability. Even buffer-free systems, which rely on the ability of the protein to buffer the formulation, appear to have acceptable stability profiles under accelerated stress conditions.

Of all of the stabilizers/tonicity modifiers evaluated, both Arg and Gly elicit very good stabilization of adalimumab. They both work better than mannitol. Mannitol does appear to be a stabilizer, however we have discovered that if used it should be at the highest possible concentrations, but in any event exceeding about 150 mM, ad most preferably at or exceeding about 200 mM. By comparison, NaCl is clearly a destabilizer, especially when the concentrations exceed 75-100 mM; hence, NaCl, if present should be controlled to levels below about 75 mM. Other polyols, such as sorbitol and trehalose, appear to work about as well as mannitol and therefore may be substituted for mannitol if desired.

Surprisingly, polysorbate 80 (PS 80) provides significant protection against thermal stress. While the mechanism of stabilization is not known, it appears that other surfactants tested (PS 20 and F-68), do not appear to be nearly as effective as PS 80. Hence the selection of PS80 versus PS 20 is a preferred feature of the present invention. Formulations according to the present invention preferably contain at least 0.04% (w/v) PS 80.

Based on the findings in the formulation studies of Blocks A through H, the following are particularly preferred adalimumab formulations according to the present invention.

TABLE M

SELECTED FORMULATIONS

| Form No | pH | His (mM) | succinate (mM) | Gly (mM) | Arg (mM) | mannitol (mM) | NaCl (mM) | PS 80 (wt %) |
|---|---|---|---|---|---|---|---|---|
| A | 5.2 | 30 | 0 | 240 | 0 | 0 | 0 | 0.1 |
| B | 5.2 | 30 | 0 | 240 | 0 | 0 | 0 | 0.02 |
| C | 5.2 | 30 | 0 | 0 | 0 | 240 | 0 | 0.1 |
| D | 5.2 | 30 | 15 | 0 | 0 | 220 | 0 | 0.1 |
| E | 5.2 | 30 | 0 | 90 | 0 | 150 | 0 | 0.1 |
| F | 5.2 | 30 | 0 | 240 | 0 | 0 | 0 | 0 |
| G | 5.2 | 20 | 0 | 0 | 0 | 240 | 0 | 0 |
| H | 5.4 | 30 | 0 | 240 | 0 | 0 | 0 | 0.02 |
| I | 5.2 | 30 | 0 | 120 | 80 | 0 | 0 | 0.1 |
| J | 5.2 | 30 | 15 | 90 | 80 | 0 | 0 | 0.1 |
| K | 5.2 | 30 | 0 | 0 | 0 | 240 | 0 | 0.1 |
| L | 5.2 | 30 | 0 | 0 | 50 | 160 | 0 | 0.1 |
| M | 5.2 | 30 | 0 | 90 | 100 | 0 | 0 | 0.1 |
| N | 5.2 | 20 | 0 | 120 | 90 | 0 | 0 | 0.1 |
| O | 5.4 | 30 | 0 | 120 | 80 | 0 | 0 | 0.1 |
| P | 5.2 | 30 | 0 | 120 | 0 | 0 | 50 | 0.01 |
| Q | 5.2 | 30 | 0 | 0 | 0 | 240 | 0 | 0.02 |

Additional Components of the Provided Pharmaceutical Compositions

The formulations of the invention may also include other buffers (unless they are specifically excluded in the description of the specific embodiments of the invention), tonicity modifiers, excipients, pharmaceutically acceptable carriers and other commonly used inactive ingredients of the pharmaceutical compositions.

A tonicity modifier is a molecule that contributes to the osmolality of a solution. The osmolality of a pharmaceutical composition is preferably adjusted to maximize the active ingredient's stability and/or to minimize discomfort to the patient upon administration. It is generally preferred that a pharmaceutical composition be isotonic with serum, i.e., having the same or similar osmolality, which is achieved by addition of a tonicity modifier.

In a preferred embodiment, the osmolality of the provided formulations is from about 180 to about 420 mOsM. However, it is to be understood that the osmolality can be either higher or lower as specific conditions require.

Examples of tonicity modifiers suitable for modifying osmolality include, but are not limited to amino acids (not including arginine) (e.g., cysteine, histidine and glycine), salts (e.g., sodium chloride or potassium chloride) and/or sugars/polyols (e.g., sucrose, sorbitol, maltose, and lactose).

In a preferred embodiment, the concentration of the tonicity modifier in the formulation is preferably between about 1 mM to about 1 M, more preferably about 10 mM to about 200 mM. Tonicity modifiers are well known in the art and are manufactured by known methods and available from commercial suppliers.

Suitable tonicity modifiers may be present in the compositions of the invention unless they are specifically excluded in the description of the specific embodiments of the invention.

Excipients, also referred to as chemical additives, co-solutes, or co-solvents, that stabilize the polypeptide while in solution (also in dried or frozen forms) can also be added to a pharmaceutical composition. Excipients are well known in the art and are manufactured by known methods and available from commercial suppliers.

Examples of suitable excipients include but are not limited to sugars/polyols such as: sucrose, lactose, glycerol, xylitol, sorbitol, mannitol, maltose, inositol, trehalose, glucose; polymers such as: serum albumin (bovine serum albumin (BSA), human SA or recombinant HA), dextran, PVA, hydroxypropyl methylcellulose (HPMC), polyethyleneimine, gelatin, polyvinylpyrrolidone (PVP), hydroxyethylcellulose (HEC); non-aqueous solvents such as: polyhydric alcohols, (e.g., PEG, ethylene glycol and glycerol) dimethylsulfoxide (DMSO) and dimethylformamide (DMF); amino acids such as: proline, L-serine, sodium glutamic acid, alanine, glycine, lysine hydrochloride, sarcosine and gamma-aminobutyric acid; surfactants such as: Tween®-80 (polysorbate 80), Tween®-20 (polysorbate 20), SDS, polysorbates, poloxamers; and miscellaneous excipients such as: potassium phosphate, sodium acetate, ammonium sulfate, magnesium sulfate, sodium sulfate, trimethylamine N-oxide, betaine, CHAPS, monolaurate, 2-O-beta-mannoglycerate or any combination of the above.

Suitable excipients may be present in the compositions of the invention unless they are specifically excluded in the description of the specific embodiments of the invention.

The concentration of one or more excipients in a formulation of the invention is/are preferably between about 0.001 to 5 weight percent, more preferably about 0.1 to 2 weight percent.

Methods of Treatment

In another embodiment, the invention provides a method of treating a mammal comprising administering a therapeutically effective amount of the pharmaceutical compositions of the invention to a mammal, wherein the mammal has a disease or disorder that can be beneficially treated with adalimumab.

In a preferred embodiment, the mammal is a human.

Diseases or disorders that can be treated with the provided compositions include but are not limited to rheumatoid arthritis, psoriatic arthritis, ankylosing spondylitis, Wegener's disease (granulomatosis), Crohn's disease (or inflammatory bowel disease), chronic obstructive pulmonary disease (COPD), Hepatitis C, endometriosis, asthma, cachexia, psoriasis, and atopic dermatitis. Additional diseases or disorders that can be treated with the compositions of the present invention include those described in U.S. Pat. Nos. 6,090,382 and 8,216,583 the relevant portions of which are incorporated herein by reference.

The provided pharmaceutical compositions may be administered to a subject in need of treatment by injection systemically, such as by intravenous injection; or by injection or application to the relevant site, such as by direct injection, or direct application to the site when the site is exposed in surgery; or by topical application.

In one embodiment, the invention provides a method of treatment and/or prevention of rheumatoid arthritis comprises administering to a mammal in need thereof a therapeutically effective amount of one of the provided adalimumab compositions.

The therapeutically effective amount of the adalimumab in the provided compositions will depend on the condition to be treated, the severity of the condition, prior therapy, and the patient's clinical history and response to the therapeutic agent. The proper dose can be adjusted according to the judgment of the attending physician such that it can be administered to the patient one time or over a series of administrations.

In one embodiment, the effective adalimumab amount per adult dose is from about 1-500 mg/m$^2$, or from about 1-200 mg/m$^2$, or from about 1-40 mg/m$^2$ or about 5-25 mg/m$^2$.

Alternatively, a flat dose may be administered, whose amount may range from 2-500 mg/dose, 2-100 mg/dose or from about 10-80 mg/dose.

If the dose is to be administered more than one time per week, an exemplary dose range is the same as the foregoing described dose ranges or lower and preferably administered two or more times per week at a per dose range of 25-100 mg/dose.

In another embodiment, an acceptable dose for administration by injection contains 80-100 mg/dose, or alternatively, containing 80 mg per dose.

The dose can be administered weekly, biweekly, or separated by several weeks (for example 2 to 8).

In one embodiment, adalimumab is administered at 40 mg by a single subcutaneous (SC) injection.

In some instances, an improvement in a patient's condition will be obtained by administering a dose of up to about 100 mg of the pharmaceutical composition one to three times per week over a period of at least three weeks. Treatment for longer periods may be necessary to induce the desired degree of improvement. For incurable chronic conditions the regimen may be continued indefinitely. For pediatric patients (ages 4-17), a suitable regimen may involve administering a dose of 0.4 mg/kg to 5 mg/kg of adalimumab, one or more times per week.

In another embodiment, the pharmaceutical formulations of the invention may be prepared in a bulk formulation, and as such, the components of the pharmaceutical composition are adjusted to be higher than would be required for administration and diluted appropriately prior to administration.

The pharmaceutical compositions can be administered as a sole therapeutic or in combination with additional therapies as needed. Thus, in one embodiment, the provided methods of treatment and/or prevention are used in combination with administering a therapeutically effective amount of another active agent. The other active agent may be administered before, during, or after administering the pharmaceutical compositions of the present invention. Another active agent may be administered either as a part of the provided compositions, or alternatively, as a separate formulation.

Administration of the provided pharmaceutical compositions can be achieved in various ways, including parenteral, oral, buccal, nasal, rectal, intraperitoneal, intradermal, transdermal, subcutaneous, intravenous, intra-arterial, intracardiac, intraventricular, intracranial, intratracheal, intrathecal administration, intramuscular injection, intravitreous injection, and topical application.

The pharmaceutical compositions of this invention are particularly useful for parenteral administration, i.e., subcutaneously, intramuscularly, intravenously, intraperitoneal, intracerobrospinal, intra-articular, intrasynovial, and/or intrathecal. Parenteral administration can be by bolus injection or continuous infusion. Pharmaceutical compositions for injection may be presented in unit dosage form, e.g., in ampoules or in multi-dose containers, with an added preservative. In addition, a number of recent drug delivery approaches have been developed and the pharmaceutical compositions of the present invention are suitable for administration using these new methods, e.g., Inject-Ease®, Genject®, injector pens such as GenPen®, and needleless devices such as MediJector® and BioJector®. The present pharmaceutical composition can also be adapted for yet to be discovered administration methods. See also Langer, 1990, Science, 249:1527-1533.

The provided pharmaceutical compositions can also be formulated as a depot preparation. Such long acting formulations may be administered by implantation (for example subcutaneously or intramuscularly) or by intramuscular injection. Thus, for example, the formulations may be modified with suitable polymeric or hydrophobic materials (for example as an emulsion in an acceptable oil) or ion exchange resins, or as sparingly soluble derivatives, for example, as a sparingly soluble salt.

The pharmaceutical compositions may, if desired, be presented in a vial, pack or dispenser device which may contain one or more unit dosage forms containing the active ingredient. In one embodiment the dispenser device can comprise a syringe having a single dose of the liquid formulation ready for injection. The syringe can be accompanied by instructions for administration.

In another embodiment, the present invention is directed to a kit or container, which contains an aqueous pharmaceutical composition of the invention. The concentration of the polypeptide in the aqueous pharmaceutical composition can vary over a wide range, but is generally within the range of from about 0.05 to about 20,000 micrograms per milliliter (μg/ml) of aqueous formulation. The kit can also be accompanied by instructions for use.

In addition to the formulations referenced in the formulation studies of Blocks A through H, the following additional examples are provided as further embodiments of the invention, as are the representative embodiments which are included in Appendices A through C which are to be understood as part of this specification.

EXAMPLE 1

Stabilized Adalimumab Formulation (Simile Buffer) Containing Polyol; without Surfactant A stable aqueous pharmaceutical composition containing adalimumab, using a single buffer, and substantially free of a surfactant may be prepared as follows:

Each solid formulation component may be weighed to the amount required for a given volume of formulation buffer. These components may then be combined into a beaker or vessel capable of carrying and measuring the given volume of formulation buffer. A volume of deionized water equal to approximately ¾ of the target given formulation buffer may be added to the beaker, and the components may be solubilized through use of a magnetic stir bar. The pH of the buffer may be adjusted to the target formulation pH using 1 molar sodium hydroxide and/or 1 molar hydrogen chloride. The final formulation buffer volume may then be raised to the target volume through the addition of deionized water. The solution may then be mixed with a magnetic stir bar after final water addition. Adalimumab solution may then be placed in dialysis material housing (such as Thermo Scientific Slide-A-Lyzer MINI Dialysis Unit 10,000 MWCO), which may then be placed in contact with the desired formulation buffer for 12 hours at 4° C. Formulation buffer volume to protein solution volume ratio should be no less than 1000:1. The dialysis housing and protein solution it contains may then be placed in a second, equal volume of formulation buffer for an additional 12 hours at 4° C.

Resulting adalimumab solution may then be removed from the dialysis material housing, and the concentration of adalimumab may then be determined using ultraviolet spectroscopy. Adalimumab concentration may then be adjusted to the desired level using centrifugation (such as Amicon Ultra 10,000 MWCO Centrifugal Concentrators) and/or dilution with formulation buffer.

A sample composition of the invention is represented in Table 1 below:

TABLE 1

| Ingredient | concentration |
|---|---|
| Adalimumab (active ingredient) | 50 mg/ml |
| Mannitol (inactive ingredient) | 4% |
| Citrate (pH 5.2) (single buffer) | 15 mM |

The composition disclosed in Table 1 does not contain a combination of citrate and phosphate buffer. It also does not require the presence of a surfactant.

EXAMPLE 2

Stabilized Adalimumab Formulation (Single Buffer) without Polyol or Surfactant

| Ingredient | concentration |
|---|---|
| Adalimumab (active ingredient) | 50 mg/ml |
| Citrate (pH 5.2) | 15 mM |
| Glycine (inactive ingredient) | 100 mM |

EXAMPLE 3

Stabilized Adalimumab Formulation (Single Buffer) Containing Polyol without Surfactant

| Ingredient | concentration |
|---|---|
| Adalimumab (active ingredient) | 50 mg/ml |
| Mannitol (inactive ingredient) | 4% |
| Citrate (pH 5.2) | 15 mM |

The compositions of examples 2 and 3 have long term stability and do not contain a combination of citrate and phosphate buffer, and do not require the presence of a surfactant.

EXAMPLE 4

Stabilized Adalimumab Formulation (Simile Buffer) Containing Surfactant; without Polyol

| 4A | |
|---|---|
| Ingredient | concentration |
| Adalimumab (active ingredient) | 50 mg/ml |
| (No polyol ingredient) | — |
| Histidine Buffer (pH 5.2) (sole buffer) | 20 mM |
| Glycine (stabilizer) | 50 mM |
| Arginine (stabilizer) | 130 mM |
| Polysorbate 80 | 0.1 (wt %) (w/v) |

4B

| Ingredient | concentration |
| --- | --- |
| Adalimumab (active ingredient) (No polyol ingredient) | 50 mg/ml — |
| Histidine Buffer (pH 5.2) (sole buffer) | 20 mM |
| Glycine (stabilizer) | 120 mM |
| Arginine (stabilizer) | 100 mM |
| Polysorbate 80 | 0.1 (wt %) (w/v) |

4C

| Ingredient | concentration |
| --- | --- |
| Adalimumab (active ingredient) (No polyol ingredient) | 50 mg/ml — |
| Histidine Buffer (pH 5.2) (sole buffer) | 10 mM |
| Glycine (stabilizer) | 50 mM |
| Arginine (stabilizer) | 130 mM |
| Polysorbate 80 | 0.1 (wt %) (w/v) |

4D

| Ingredient | concentration |
| --- | --- |
| Adalimumab (active ingredient) (No polyol ingredient) | 50 mg/ml — |
| Succinate Buffer (pH 5.2) (sole buffer) | 20 mM |
| Glycine (stabilizer) | 50 mM |
| Arginine (stabilizer) | 130 mM |
| Polysorbate 80 | 0.1 (wt %) (w/v) |

4E

| Ingredient | concentration |
| --- | --- |
| Adalimumab (active ingredient) (No polyol ingredient) | 50 mg/ml — |
| Succinate Buffer (pH 5.2) (sole buffer) | 20 mM |
| Glycine (stabilizer) | 120 mM |
| Arginine (stabilizer) | 100 mM |
| Polysorbate 80 | 0.1 (wt %) (w/v) |

4F

| Ingredient | concentration |
| --- | --- |
| Adalimumab (active ingredient) (No polyol ingredient) | 50 mg/ml — |
| Succinate Buffer (pH 5.2) (sole buffer) | 10 mM |
| Glycine (stabilizer) | 50 mM |
| Arginine (stabilizer) | 130 mM |
| Polysorbate 80 | 0.1 (wt %) (w/v) |

The compositions disclosed in Examples 4(a) through 4(f) above will afford stability without need for polyol and without need for a combined buffer system. Insofar as the present invention has discovered that the citrate/phosphate buffer combination required in U.S. Pat. No. 8,216,583 is not required for stabilization of adalimumab formulations according to the present invention, persons skilled in the art may appreciate, in practicing examples 4(a) through 4(f), that additional buffers may be employed in combination with the histidine and succinate buffers disclosed herein (e.g., acetate, citrate, maleate, tartrate, and phosphate buffers); provided the formulation does not use a buffer combination of citrate and phosphate.

EXAMPLE 5

Stabilized Adalimumab Formulation (Simile Buffer) Containing Surfactant; and Polyol

5A

| Ingredient | Concentration |
| --- | --- |
| Adalimumab (active ingredient) | 50 mg/ml |
| Sorbitol | 65 mM |
| Histidine Buffer (pH 5.2) (sole buffer) | 20 mM |
| Arginine (stabilizer) | 130 mM |
| Polysorbate 80 | 0.1 (wt %) (w/v) |

5B

| Ingredient | Concentration |
| --- | --- |
| Adalimumab (active ingredient) | 50 mg/ml |
| Sorbitol | 65 mM |
| Succinate Buffer (pH 5.2) (sole buffer) | 20 mM |
| Arginine (stabilizer) | 130 mM |
| Polysorbate 80 | 0.1 (wt %) (w/v) |

The foregoing description of the exemplary embodiments of the invention in the block studies A through H, in the examples above, and in the Appendices A through C, are presented only for the purposes of illustration and description and is not intended to be exhaustive or to limit the invention to the precise forms disclosed. Many modifications and variations are possible in light of the above teaching.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

APPENDIX A

Further Representative Embodiments

Disclosed in Priority Application U.S. Ser. No. 61/698,138

A. A stable aqueous pharmaceutical composition comprising adalimumab, a polyol, a surfactant, and a buffer selected from the group consisting of citrate, phosphate, succinate, histidine, tartrate and maleate, wherein said composition has a pH of about 5 to about 6, and wherein said buffer does not comprise both of citrate and phosphate.

B. A stable aqueous pharmaceutical composition comprising adalimumab, a polyol, and a surfactant, wherein said composition has a pH of about 5 to about 6, and wherein said composition is substantially free of a buffer.

C. The composition of any of embodiments A-B, wherein said adalimumab is at a concentration from about 20 to about 150 mg/ml.

D. The composition of any of embodiments A-C, wherein said adalimumab is at a concentration from about 20 to about 100 mg/ml.
E. The composition of any of embodiments A-D, wherein said adalimumab is at a concentration from about 30 to about 50 mg/ml.
F. The composition of any of embodiments A-E, wherein said buffer is at a concentration from about 5 mM to about 50 mM.
G. The composition of any of embodiments A-F, wherein said buffer is at a concentration from about 5 mM to about 20 mM.
H. The composition of any of embodiments A-G, wherein said buffer is at a concentration from about 10 mM to about 20 mM.
I. The composition of any of embodiments A-G, wherein said surfactant is a polysorbate.
J. The composition of embodiment I, wherein said polysorbate is polysorbate 80.
K. The composition of any of embodiments A-J, wherein said polyol is a sugar alcohol.
L. The composition of embodiment K, wherein said sugar alcohol is selected from the group consisting of mannitol, sorbitol and trehalose.
M. The composition of embodiment L, wherein said mannitol is at a concentration from about 1 to 10% weight by volume of the total composition.
N. The composition of any of embodiments L-M, wherein said mannitol is at a concentration from about 2 to 6% weight by volume of the total composition.
O. The composition of any of embodiments L-N, wherein said mannitol is at a concentration from about 3 to 5% weight by volume of the total composition.
P. The composition of any of embodiments A-O further comprising a stabilizer selected from the group consisting of an amino acid, a salt, ethylenediaminetetraacetic acid (EDTA) and a metal ion.
Q. The composition of embodiment P, wherein said amino acid is selected from the group consisting of glycine, alanine, glutamate, arginine and methionine.
R. The composition of embodiment P, wherein said salt is selected from the group consisting of sodium chloride and sodium sulfate.
S. The composition of embodiment P, wherein said metal ion is selected from zinc, magnesium and calcium.
T. A stable aqueous pharmaceutical composition comprising adalimumab at a concentration from about 20 and about 150 mg/ml, mannitol at a concentration from about 1 to 10% weight by volume, polysorbate 80 at a concentration from about 1 to 50 µM, and citrate at a concentration from about 5 mM and about 50 mM, wherein said composition has a pH of about 5 to about 5.5, and wherein said composition is substantially free of phosphate.
U. A stable aqueous pharmaceutical composition comprising adalimumab, a polyol, and a buffer selected from the group consisting of citrate, phosphate, succinate, histidine, tartrate and maleate, wherein said composition has a pH of about 5 to about 6, and wherein said composition is substantially free of a surfactant.
V. The composition of embodiment U, wherein said adalimumab is at a concentration from about 20 and about 150 mg/ml.
W. The composition of any of embodiments U-V, wherein said adalimumab is at a concentration from about 20 and about 100 mg/ml.
X. The composition of any of embodiments U-V, wherein said adalimumab is at a concentration from about 20 and about 40 mg/ml.
Y. The composition of any of embodiments U-Y, wherein said buffer is at a concentration from about 5 mM and about 50 mM.
Z. The composition of any of embodiments U-Y, wherein said buffer is at a concentration from about 5 mM and about 20 mM.
AA. The composition of any of embodiments U-Z, wherein said buffer is at a concentration from about 10 mM and about 20 mM.
BB. The composition of any of embodiments U-AA, wherein said polyol is a sugar alcohol.
CC. The composition of embodiment BB, wherein said sugar alcohol is selected from the group consisting of mannitol, sorbitol and trehalose.
DD. The composition of embodiment CC, wherein said mannitol is at a concentration from about 1 to 10% weight by volume of the total composition.
EE. The composition of any of embodiments CC-DD, wherein said mannitol is at a concentration from about 2 to 6% weight by volume of the total composition.
FF. The composition of any of embodiments CC-EE, wherein said mannitol is at a concentration from about 3 to 5% weight by volume of the total composition.
GG. The composition of any of embodiments CC-FF further comprising a stabilizer selected from the group consisting of an amino acid, a salt, ethylenediaminetetraacetic acid (EDTA) and a metal ion.
HH. The composition of embodiment GG, wherein said amino acid is selected from the group consisting of glycine, alanine, glutamate, arginine and methionine.
II. The composition of embodiment GG, wherein said salt is selected from the group consisting of sodium chloride and sodium sulfate.
JJ. The composition of embodiment GG, wherein said metal ion is selected from zinc, magnesium and calcium.
KK. A stable aqueous pharmaceutical composition comprising adalimumab at a concentration from about 20 and about 150 mg/ml, mannitol at a concentration from about 1 to 10% weight by volume, and citrate at a concentration from about 5 mM and about 50 mM, wherein said composition has a pH of about 5 to about 5.5, and wherein said composition is substantially free of a surfactant.
LL. A stable aqueous pharmaceutical composition comprising adalimumab, a buffer, a stabilizer selected from the group consisting of an amino acid, a salt, ethylenediaminetetraacetic acid (EDTA) and a metal ion, and wherein said composition has a pH of about 5 to about 6, and wherein said composition is substantially free of a polyol.
MM. The composition of embodiment LL, wherein said adalimumab is at a concentration from about 20 and about 150 mg/ml.
NN. The composition of any of embodiments LL-MM, wherein said adalimumab is at a concentration from about 20 and about 100 mg/ml.
OO. The composition of any of embodiments LL-NN, wherein said adalimumab is at a concentration from about 20 and about 40 mg/ml.
PP. The composition of any of embodiments LL-OO, wherein said buffer is at a concentration from about 5 mM and about 50 mM.

QQ. The composition of any of embodiments LL-PP, wherein said buffer is at a concentration from about 5 mM and about 20 mM.

RR. The composition of any of embodiments LL-QQ, wherein said buffer is at a concentration from about 10 mM and about 20 mM.

SS. The composition of embodiment LL, wherein said stabilizer is selected from the group consisting of an amino acid, a salt, EDTA and a metal ion.

TT. The composition of embodiment SS, wherein said amino acid is selected from the group consisting of glycine, alanine and arginine.

UU. The composition of embodiment SS wherein said salt is selected from the group consisting of sodium chloride and sodium sulfate.

VV. The composition of embodiment TT, wherein said glycine is at a concentration from about 20 to about 200 mM.

WW. The composition of embodiment W, wherein said glycine is at a concentration from about 50 to about 200 mM.

XX. The composition of embodiment SS, wherein said arginine is at a concentration from about 1 to about 250 mM.

YY. The composition of embodiment XX, wherein said arginine is at a concentration from about 20 to about 200 mM.

ZZ. The composition of embodiment YY, wherein said arginine is at a concentration from about 20 to about 100 mM.

AAA. The composition of embodiment UU, wherein said sodium chloride is at a concentration from about 5 to about 150 mM.

BBB. The composition of embodiment AAA, wherein said sodium chloride is at a concentration from about 20 to about 140 mM.

CCC. The composition of embodiment BBB, wherein said sodium chloride is at a concentration from about 75 to about 125 mM.

DDD. The composition of embodiment UU, wherein said sodium sulfate is at a concentration from about 5 to about 150 mM.

EEE. The composition of embodiment UU, wherein said sodium chloride is at a concentration from about 20 to about 120 mM.

FFF. The composition of embodiment EEE, wherein said sodium chloride is at a concentration from about 60 to about 100 mM.

GGG. The composition of any of embodiments LL-FF further comprising a surfactant.

HHH. The composition of embodiment GGG, wherein said surfactant is a polysorbate.

III. The composition of embodiment HHH, wherein said polysorbate is polysorbate 80.

JJJ. A stable aqueous pharmaceutical composition comprising adalimumab at a concentration from about 20 and about 150 mg/ml, glycine at a concentration from about 20 to about 200 mM, citrate at a concentration from about 5 mM and about 50 mM, wherein said composition has a pH of about 5 to about 5.5, and wherein said composition is substantially free of a polyol.

KKK. A stable aqueous pharmaceutical composition comprising adalimumab at a concentration from about 20 and about 150 mg/ml, arginine at a concentration from about 1 to about 250 mM, citrate at a concentration from about 5 mM and about 50 mM, wherein said composition has a pH from about 5 to about 5.5, and wherein said composition is substantially free of a polyol.

LLL. A stable aqueous pharmaceutical composition comprising adalimumab at a concentration from about 20 and about 150 mg/ml, sodium chloride at a concentration from about 5 to about 150 mM, citrate at a concentration from about 5 mM and about 50 mM, wherein said composition has a pH of about 5 to about 5.5, and wherein said composition is substantially free of a polyol.

MMM. A stable aqueous pharmaceutical composition comprising adalimumab at a concentration from about 20 and about 150 mg/ml, sodium chloride at a concentration from about 5 to about 150 mM, polysorbate 80 at a concentration from about 1 to 50 µM, citrate at a concentration from about 5 mM and about 50 mM, wherein said composition has a pH of about 5 to about 5.5, and wherein said composition is substantially free of a polyol.

NNN. A stable aqueous pharmaceutical composition comprising adalimumab, a polyol, a surfactant, a stabilizer selected from the group consisting of an amino acid, a salt, ethylenediaminetetraacetic acid (EDTA) and a metal ion, and a buffer selected from the group consisting of citrate, phosphate, succinate, tartrate and maleate, wherein said composition has a pH from about 5 to about 6.

OOO. The composition of embodiment NNN, wherein the buffer does not comprise a combination of citrate and phosphate.

PPP. The composition of embodiment NNN, wherein said adalimumab is at a concentration from about 20 and about 150 mg/ml.

QQQ. The composition of any of embodiments NNN-PPP, wherein said adalimumab is at a concentration from about 20 and about 100 mg/ml.

RRR. The composition of any of embodiments NNN-QQQ, wherein said adalimumab is at a concentration from about 20 and about 40 mg/ml.

SSS. The composition of any of embodiments NNN-RRR, wherein said buffer is at a concentration from about 5 mM and about 50 mM.

TTT. The composition of any of embodiments NNN-SSS, wherein said buffer is at a concentration from about 5 mM and about 20 mM.

UUU. The composition of any of embodiments NNN-TTT, wherein said buffer is at a concentration from about 10 mM and about 20 mM.

VVV. The composition of any of embodiments NNN-UUU, wherein said surfactant is a polysorbate.

WWW. The composition of embodiment VVV, wherein said polysorbate is polysorbate 80.

XXX. The composition of any of embodiments NNN-WWW, wherein said polyol is a sugar alcohol.

YYY. The composition of embodiment XXX, wherein said sugar alcohol is selected from the group consisting of mannitol, sorbitol and trehalose.

ZZZ. The composition of embodiment XXX, wherein said mannitol is at a concentration from about 1 to 10% weight by volume of the total composition.

AAAA. The composition of any of embodiments XXX-ZZZ, wherein said mannitol is at a concentration from about 2 to 6% weight by volume of the total composition.

BBBB. The composition of any of embodiments YYY-AAAA, wherein said mannitol is at a concentration from about 3 to 5% weight by volume of the total composition.

CCCC. The composition of any of embodiments NNN-BBBB, wherein said stabilizer is EDTA.

DDDD. The composition of embodiment CCCC, wherein said EDTA is at a concentration from about 0.01% to about 0.5%.

EEEE. The composition of embodiment DDDD, wherein said EDTA is at a concentration from about 0.05% to about 0.25%.

FFFF. The composition of embodiment EEEE, wherein said EDTA is at a concentration from about 0.08% to about 0.2%.

GGGG. The composition of any of embodiments NNN-BBBB, wherein said stabilizer is methionine.

HHHH. The composition of embodiment GGGG, wherein said methionine is at a concentration from about 1 to about 10 mg/ml.

IIII. The composition of embodiment GGGG, wherein said methionine is at a concentration from about 1 to about 5 mg/ml.

JJJJ. A stable aqueous pharmaceutical composition comprising adalimumab at a concentration from about 20 and about 150 mg/ml, polysorbate 80 at a concentration from about 1 to about 50 µM, mannitol at a concentration from about 1 to 10% weight by volume, EDTA at a concentration from about 0.01% to about 0.5%, citrate at a concentration from about 5 mM and about 50 mM, and wherein said composition has a pH of about 5 to about 5.5.

KKKK. A stable aqueous pharmaceutical composition comprising adalimumab at a concentration from about 20 and about 150 mg/ml, polysorbate 80 at a concentration from about 1 to about 50 µM, mannitol at a concentration from about 1 to 10% weight by volume, methionine at a concentration from about 1 to about 10 mg/ml, citrate at a concentration from about 5 mM and about 50 mM, and wherein said composition has a pH of about 5 to about 5.5.

LLLL. A stable aqueous pharmaceutical composition comprising adalimumab, a polyol, and a buffer selected from the group consisting of citrate, phosphate, succinate, tartrate and maleate, wherein said composition has a pH of about 3.5.

MMMM. The composition of embodiment LLLL, wherein said adalimumab is at a concentration from about 20 and about 150 mg/ml.

NNNN. The composition of any of embodiments LLLL-MMMM, wherein said adalimumab is at a concentration from about 20 and about 100 mg/ml.

OOOO. The composition of any of embodiments LLLL-NNNN, wherein said adalimumab is at a concentration from about 20 and about 40 mg/ml.

PPPP. The composition of any of embodiments LLLL-OOOO, wherein said buffer is at a concentration from about 5 mM and about 50 mM.

QQQQ. The composition of any of embodiments LLLL-PPPP, wherein said buffer is at a concentration from about 5 mM and about 20 mM.

RRRR. The composition of any of embodiments LLLL-QQQQ, wherein said buffer is at a concentration from about 10 mM and about 20 mM.

SSSS. The composition of any of embodiments LLLL-RRRR, wherein said polyol is a sugar alcohol.

TTTT. The composition of embodiment SSSS, wherein said sugar alcohol is selected from the group consisting of mannitol, sorbitol and trehalose.

UUUU. The composition of embodiment TTTT, wherein said mannitol is at a concentration from about 1 to about 10% weight by volume of the total composition.

VVVV. The composition of any of embodiments TTTT-UUUU, wherein said mannitol is at a concentration from about 2 to about 6% weight by volume of the total composition.

WWWW. The composition of any of embodiments TTTT-VVVV, wherein said mannitol is at a concentration from about 3 to about 5% weight by volume of the total composition.

XXXX. The composition of any of embodiments LLLL-WWWW further comprising a stabilizer selected from the group consisting of an amino acid, a salt, ethylenediaminetetraacetic acid (EDTA) and a metal ion.

YYYY. The composition of embodiment XXXX, wherein said amino acid is selected from the group consisting of glycine, alanine, glutamate, arginine and methionine.

ZZZZ. The composition of embodiment XXXX, wherein said salt is selected from the group consisting of sodium chloride and sodium sulfate.

AAAAA. The composition of embodiment XXXX, wherein said metal ion is selected from zinc, magnesium and calcium.

BBBBB. The composition of any of embodiments TTTT-AAAAA further comprising a surfactant.

CCCCC. The composition of embodiment BBBBB, wherein said surfactant is a polysorbate.

DDDDD. The composition of embodiment CCCCC, wherein said polysorbate is polysorbate 80.

APPENDIX B

Further Representative Embodiments

Disclosed in Priority Application U.S. Ser. No. 61/770,421

A. A stable aqueous pharmaceutical composition comprising adalimumab, a polyol, a surfactant, and a buffer selected from the group consisting of citrate, phosphate, succinate, histidine, tartrate and maleate, wherein said composition has a pH of about 5 to about 6, and wherein said buffer does not comprise both of citrate and phosphate.

B. A stable aqueous pharmaceutical composition comprising adalimumab, a polyol, and a surfactant, wherein said composition has a pH of about 5 to about 6, and wherein said composition is substantially free of a buffer.

C. The composition of any of embodiments A-B, wherein said adalimumab is at a concentration from about 20 to about 150 mg/ml.

D. The composition of any of embodiments A-C, wherein said adalimumab is at a concentration from about 20 to about 100 mg/ml.

E. The composition of any of embodiments A-D, wherein said adalimumab is at a concentration from about 30 to about 50 mg/ml.

F. The composition of any of embodiments A-E, wherein said buffer is at a concentration from about 5 mM to about 50 mM.

G. The composition of any of embodiments A-F, wherein said buffer is at a concentration from about 5 mM to about 20 mM.

H. The composition of any of embodiments A-G, wherein said buffer is at a concentration from about 10 mM to about 20 mM.

I. The composition of any of embodiments A-H, wherein said surfactant is a polysorbate.

J. The composition of embodiment I, wherein said polysorbate is polysorbate 80.

K. The composition of any of embodiments A-J, wherein said polyol is a sugar alcohol.

L. The composition of embodiment K, wherein said sugar alcohol is selected from the group consisting of mannitol, sorbitol and trehalose.

M. The composition of embodiment L, wherein said mannitol is at a concentration from about 1 to 10% weight by volume of the total composition.

N. The composition of any of embodiments L-M, wherein said mannitol is at a concentration from about 2 to 6% weight by volume of the total composition.

O. The composition of any of embodiments L-N, wherein said mannitol is at a concentration from about 3 to 5% weight by volume of the total composition.

P. The composition of any of embodiments A-O further comprising a stabilizer selected from the group consisting of an amino acid, a salt, ethylenediaminetetraacetic acid (EDTA) and a metal ion.

Q. The composition of embodiment P, wherein said amino acid is selected from the group consisting of glycine, alanine, glutamate, arginine and methionine.

R. The composition of embodiment P, wherein said salt is selected from the group consisting of sodium chloride and sodium sulfate.

S. The composition of embodiment P, wherein said metal ion is selected from zinc, magnesium and calcium.

T. A stable aqueous pharmaceutical composition comprising adalimumab at a concentration from about 20 and about 150 mg/ml, mannitol at a concentration from about 1 to 10% weight by volume, polysorbate 80 at a concentration from about 1 to 50 μM, and citrate at a concentration from about 5 mM and about 50 mM, wherein said composition has a pH of about 5 to about 5.5, and wherein said composition is substantially free of phosphate.

U. A stable aqueous pharmaceutical composition comprising adalimumab, a polyol, and a buffer selected from the group consisting of citrate, phosphate, succinate, histidine, tartrate and maleate, wherein said composition has a pH of about 5 to about 6, and wherein said composition is substantially free of a surfactant.

V. The composition of embodiment U, wherein said adalimumab is at a concentration from about 20 and about 150 mg/ml.

W. The composition of any of embodiments U-V, wherein said adalimumab is at a concentration from about 20 and about 100 mg/ml.

X. The composition of any of embodiments U-W, wherein said adalimumab is at a concentration from about 20 and about 40 mg/ml.

Y. The composition of any of embodiments U-X, wherein said buffer is at a concentration from about 5 mM and about 50 mM.

Z. The composition of any of embodiments U-Y, wherein said buffer is at a concentration from about 5 mM and about 20 mM.

AA. The composition of any of embodiments U-Z, wherein said buffer is at a concentration from about 10 mM and about 20 mM.

BB. The composition of any of embodiments U-AA, wherein said polyol is a sugar alcohol.

CC. The composition of embodiment BB, wherein said sugar alcohol is selected from the group consisting of mannitol, sorbitol and trehalose.

DD. The composition of embodiment CC, wherein said mannitol is at a concentration from about 1 to 10% weight by volume of the total composition.

EE. The composition of any of embodiments CC-DD, wherein said mannitol is at a concentration from about 2 to 6% weight by volume of the total composition.

FF. The composition of any of embodiments CC-EE, wherein said mannitol is at a concentration from about 3 to 5% weight by volume of the total composition.

GG. The composition of any of embodiments U-FF further comprising a stabilizer selected from the group consisting of an amino acid, a salt, ethylenediaminetetraacetic acid (EDTA) and a metal ion.

HH. The composition of embodiment GG, wherein said amino acid is selected from the group consisting of glycine, alanine, glutamate, arginine and methionine.

II. The composition of embodiment GG, wherein said salt is selected from the group consisting of sodium chloride and sodium sulfate.

JJ. The composition of embodiment GG, wherein said metal ion is selected from zinc, magnesium and calcium.

KK. A stable aqueous pharmaceutical composition comprising adalimumab at a concentration from about 20 and about 150 mg/ml, mannitol at a concentration from about 1 to 10% weight by volume, and citrate at a concentration from about 5 mM and about 50 mM, wherein said composition has a pH of about 5 to about 5.5, and wherein said composition is substantially free of a surfactant.

LL. A stable aqueous pharmaceutical composition comprising adalimumab, a buffer, a stabilizer selected from the group consisting of an amino acid, a salt, ethylenediaminetetraacetic acid (EDTA) and a metal ion, and wherein said composition has a pH of about 5 to about 6, and wherein said composition is substantially free of a polyol.

MM. The composition of embodiment LL, wherein said adalimumab is at a concentration from about 20 and about 150 mg/ml.

NN. The composition of any of embodiments LL-MM, wherein said adalimumab is at a concentration from about 20 and about 100 mg/ml.

OO. The composition of any of embodiments LL-NN, wherein said adalimumab is at a concentration from about 20 and about 40 mg/ml.

PP. The composition of any of embodiments LL-OO, wherein said buffer is at a concentration from about 5 mM and about 50 mM.

QQ. The composition of any of embodiments LL-PP, wherein said buffer is at a concentration from about 5 mM and about 20 mM.

RR. The composition of any of embodiments LL-QQ, wherein said buffer is at a concentration from about 10 mM and about 20 mM.

SS. The composition of embodiment LL, wherein said stabilizer is selected from the group consisting of an amino acid, a salt, EDTA and a metal ion.

TT. The composition of embodiment TT, wherein said amino acid is selected from the group consisting of glycine, alanine and arginine.

UU. The composition of embodiment TT, wherein said salt is selected from the group consisting of sodium chloride and sodium sulfate.

VV. The composition of embodiment TT, wherein said glycine is at a concentration from about 20 to about 200 mM.

WW. The composition of embodiment W, wherein said glycine is at a concentration from about 50 to about 200 mM.

XX. The composition of embodiment TT, wherein said arginine is at a concentration from about 1 to about 250 mM.

YY. The composition of embodiment XX, wherein said arginine is at a concentration from about 20 to about 200 mM.

ZZ. The composition of embodiment YY, wherein said arginine is at a concentration from about 20 to about 100 mM.

AAA. The composition of embodiment UU, wherein said sodium chloride is at a concentration from about 5 to about 150 mM.

BBB. The composition of embodiment AAA, wherein said sodium chloride is at a concentration from about 20 to about 140 mM.

CCC. The composition of embodiment AAA, wherein said sodium chloride is at a concentration from about 75 to about 125 mM.

DDD. The composition of embodiment UU, wherein said sodium sulfate is at a concentration from about 5 to about 150 mM.

EEE. The composition of embodiment UU, wherein said sodium chloride is at a concentration from about 20 to about 120 mM.

FFF. The composition of embodiment EEE, wherein said sodium chloride is at a concentration from about 60 to about 100 mM.

GGG. The composition of any of embodiments LL-FF further comprising a surfactant.

HHH. The composition of embodiment GGG, wherein said surfactant is a polysorbate.

III. The composition of embodiment HHH, wherein said polysorbate is polysorbate 80.

JJJ. A stable aqueous pharmaceutical composition comprising adalimumab at a concentration from about 20 and about 150 mg/ml, glycine at a concentration from about 20 to about 200 mM, citrate at a concentration from about 5 mM and about 50 mM, wherein said composition has a pH of about 5 to about 5.5, and wherein said composition is substantially free of a polyol.

KKK. A stable aqueous pharmaceutical composition comprising adalimumab at a concentration from about 20 and about 150 mg/ml, arginine at a concentration from about 1 to about 250 mM, citrate at a concentration from about 5 mM and about 50 mM, wherein said composition has a pH from about 5 to about 5.5, and wherein said composition is substantially free of a polyol.

LLL. A stable aqueous pharmaceutical composition comprising adalimumab at a concentration from about 20 and about 150 mg/ml, sodium chloride at a concentration from about 5 to about 150 mM, citrate at a concentration from about 5 mM and about 50 mM, wherein said composition has a pH of about 5 to about 5.5, and wherein said composition is substantially free of a polyol.

MMM. A stable aqueous pharmaceutical composition comprising adalimumab at a concentration from about 20 and about 150 mg/ml, sodium chloride at a concentration from about 5 to about 150 mM, polysorbate 80 at a concentration from about 1 to 50 µM, citrate at a concentration from about 5 mM and about 50 mM, wherein said composition has a pH of about 5 to about 5.5, and wherein said composition is substantially free of a polyol.

NNN. A stable aqueous pharmaceutical composition comprising adalimumab, a polyol, a surfactant, a stabilizer selected from the group consisting of an amino acid, a salt, ethylenediaminetetraacetic acid (EDTA) and a metal ion, and a buffer selected from the group consisting of citrate, phosphate, succinate, tartrate and maleate, wherein said composition has a pH from about 5 to about 6.

OOO. The composition of embodiment NNN, wherein the buffer does not comprise a combination of citrate and phosphate.

PPP. The composition of embodiment NNN, wherein said adalimumab is at a concentration from about 20 and about 150 mg/ml.

QQQ. The composition of any of embodiments NNN-PPP, wherein said adalimumab is at a concentration from about 20 and about 100 mg/ml.

RRR. The composition of any of embodiments NNN-QQQ, wherein said adalimumab is at a concentration from about 20 and about 40 mg/ml.

SSS. The composition of any of embodiments NNN-RRR, wherein said buffer is at a concentration from about 5 mM and about 50 mM.

TTT. The composition of any of embodiments NNN-SSS, wherein said buffer is at a concentration from about 5 mM and about 20 mM.

UUU. The composition of any of embodiments NNN-TTT, wherein said buffer is at a concentration from about 10 mM and about 20 mM.

VVV. The composition of any of embodiments NNN-UUU, wherein said surfactant is a polysorbate.

WWW. The composition of embodiment VVV, wherein said polysorbate is polysorbate 80.

XXX. The composition of any of embodiments NNN-WWW, wherein said polyol is a sugar alcohol.

YYY. The composition of embodiment XXX, wherein said sugar alcohol is selected from the group consisting of mannitol, sorbitol and trehalose.

ZZZ. The composition of embodiment YYY, wherein said mannitol is at a concentration from about 1 to 10% weight by volume of the total composition.

AAAA. The composition of any of embodiments YYY-ZZZ, wherein said mannitol is at a concentration from about 2 to 6% weight by volume of the total composition.

BBBB. The composition of any of embodiments YYY-AAAA, wherein said mannitol is at a concentration from about 3 to 5% weight by volume of the total composition.

CCCC. The composition of any of embodiments NNN-BBBB, wherein said stabilizer is EDTA.

DDDD. The composition of embodiment CCCC, wherein said EDTA is at a concentration from about 0.01% to about 0.5%.

EEEE. The composition of embodiment DDDD, wherein said EDTA is at a concentration from about 0.05% to about 0.25%.

FFFF. The composition of embodiment EEEE, wherein said EDTA is at a concentration from about 0.08% to about 0.2%.

GGGG. The composition of any of embodiments NNN-BBBB, wherein said stabilizer is methionine.

HHHH. The composition of embodiment GGGG, wherein said methionine is at a concentration from about 1 to about 10 mg/ml.

IIII. The composition of embodiment GGGG, wherein said methionine is at a concentration from about 1 to about 5 mg/ml.

JJJJ. A stable aqueous pharmaceutical composition comprising adalimumab at a concentration from about 20 and about 150 mg/ml, polysorbate 80 at a concentration from about 1 to about 50 µM, mannitol at a concentration from about 1 to 10% weight by volume, EDTA at a concentration from about 0.01% to about 0.5%, citrate at a concentration from about 5 mM and about 50 mM, and wherein said composition has a pH of about 5 to about 5.5.

KKKK. A stable aqueous pharmaceutical composition comprising adalimumab at a concentration from about 20 and about 150 mg/ml, polysorbate 80 at a concentration from about 1 to about 50 µM, mannitol at a concentration from about 1 to 10% weight by volume, methionine at a concentration from about 1 to about 10 mg/ml, citrate at a concentration from about 5 mM and about 50 mM, and wherein said composition has a pH of about 5 to about 5.5.

LLLL. A stable aqueous pharmaceutical composition comprising adalimumab, a polyol, and a buffer selected from the group consisting of citrate, phosphate, succinate, tartrate and maleate, wherein said composition has a pH of about 3.5.

MMMM. The composition of embodiment LLLL, wherein said adalimumab is at a concentration from about 20 and about 150 mg/ml.

NNNN. The composition of any of embodiments LLLL-MMMM, wherein said adalimumab is at a concentration from about 20 and about 100 mg/ml.

OOOO. The composition of any of embodiments LLLL-NNNN, wherein said adalimumab is at a concentration from about 20 and about 40 mg/ml.

PPPP. The composition of any of embodiments LLLL-OOOO, wherein said buffer is at a concentration from about 5 mM and about 50 mM.

QQQQ. The composition of any of embodiments LLLL-PPPP, wherein said buffer is at a concentration from about 5 mM and about 20 mM.

RRRR. The composition of any of embodiments LLLL-QQQQ, wherein said buffer is at a concentration from about 10 mM and about 20 mM.

SSSS. The composition of any of embodiments LLLL-RRRR, wherein said polyol is a sugar alcohol.

TTTT. The composition of embodiment SSSS, wherein said sugar alcohol is selected from the group consisting of mannitol, sorbitol and trehalose.

UUUU. The composition of embodiment TTTT, wherein said mannitol is at a concentration from about 1 to about 10% weight by volume of the total composition.

VVVV. The composition of any of embodiments TTTT-UUUU, wherein said mannitol is at a concentration from about 2 to about 6% weight by volume of the total composition.

WWWW. The composition of any of embodiments TTTT-VVVV, wherein said mannitol is at a concentration from about 3 to about 5% weight by volume of the total composition.

XXXX. The composition of any of embodiments LLLL-WWWW further comprising a stabilizer selected from the group consisting of an amino acid, a salt, ethylenediaminetetraacetic acid (EDTA) and a metal ion.

YYYY. The composition of embodiment XXXX, wherein said amino acid is selected from the group consisting of glycine, alanine, glutamate, arginine and methionine.

ZZZZ. The composition of embodiment XXXX, wherein said salt is selected from the group consisting of sodium chloride and sodium sulfate.

AAAAA. The composition of embodiment XXXX, wherein said metal ion is selected from zinc, magnesium and calcium.

BBBBB. The composition of any of embodiments LLLL-AAAAA further comprising a surfactant.

CCCCC. The composition of embodiment BBBBB, wherein said surfactant is a polysorbate.

DDDDD. The composition of embodiment CCCCC, wherein said polysorbate is polysorbate 80.

EEEEE. A stable aqueous pharmaceutical composition comprising adalimumab at a concentration from about 20 and about 150 mg/ml, polysorbate 80 at a concentration from about 1 to about 50 µM; polyol selected from sorbitol, mannitol or trehalose at a concentration from about 1 to about 10% weight by volume, and at least one amino acid stabilizer selected from the group consisting of (a) arginine at a concentration from about 1 to about 250 mg/ml and (b) glycine at a concentration of about 20 to 200 mg/ml, and histidine buffer or succinate buffer at a concentration from about 5 mM and about 50 mM, and wherein said composition has a pH of about 5 to about 5.5.

FFFFF. The composition of embodiment EEEEE wherein the polyol is sorbitol, and the composition is free or substantially free of any citrate/phosphate buffer combination, and the formulation comprises arginine or glycine, but not both.

GGGGG. A stable aqueous pharmaceutical composition comprising adalimumab at a concentration from about 20 and about 150 mg/ml, polysorbate 80 at a concentration from about 1 to about 50 µM, arginine at a concentration from about 1 to about 250 mg/ml, glycine at a concentration of about 20 to 200 mg/ml, and histidine buffer or succinate buffer at a concentration from about 5 mM and about 50 mM, and wherein said composition has a pH of about 5 to about 5.5 and said composition is free or substantially free of polyol.

HHHHH. The composition of embodiment GGGGG wherein the composition is free or substantially free of any citrate/phosphate buffer combination.

APPENDIX C

Further Representative Embodiments

Disclosed in Priority Application U.S. Ser. No. 61/769,581

A. A stable aqueous pharmaceutical composition comprising adalimumab and a single buffer.

B. The composition of embodiment A, wherein said single buffer is selected from the group consisting of succinate, histidine, citrate, phosphate, tartrate and maleate.

C. The composition of any of the preceding embodiments, wherein said composition has a pH of about 5 to about 6.
D. The composition of any of the preceding embodiments, wherein said adalimumab contained in said pharmaceutical compositions does not lose more than 20% of its activity relative to activity of the composition at the beginning of storage.
E. The composition of any of the preceding embodiments, further comprising a surfactant.
F. The composition of embodiment E, wherein said surfactant is a polysorbate.
G. The composition of embodiment F wherein said polysorbate is polysorbate 80.
H. The composition of any of the preceding embodiments, further comprising a polyol.
I. The composition of embodiment H, wherein said polyol is a sugar alcohol.
J. The composition of embodiment I, wherein said sugar alcohol is sorbitol.
K. The composition of any of the preceding embodiments, further comprising a sugar.
L. The composition of embodiment K, wherein said sugar is selected from the group consisting of sucrose and trehalose.
M. The composition of any of the preceding embodiments, wherein said adalimumab is at a concentration from about 20 to about 150 mg/ml.
N. The composition of any of the preceding embodiments, wherein said buffer is at a concentration from about 5 mM to about 50 mM.
O. The composition of any of embodiments A-N further comprising a stabilizer selected from the group consisting of an amino acid, a salt, ethylenediaminetetraacetic acid (EDTA) and a metal ion.
P. The composition of embodiment O, wherein said amino acid is selected from the group consisting of glycine, alanine, glutamate, arginine and methionine.
Q. The composition of embodiment O, wherein said metal ion is selected from zinc, magnesium and calcium.
R. A stable aqueous pharmaceutical composition comprising adalimumab at a concentration from about 20 and about 150 mg/ml, polysorbate 80 at a concentration from about 0.01% w/v to 0.5% w/v by weight of the total formulation, and succinate at a concentration from about 5 mM and about 50 mM, wherein said composition has a pH of about 5 to about 5.5, and wherein said composition is substantially free of any other buffers.
S. A stable aqueous pharmaceutical composition comprising adalimumab at a concentration from about 20 and about 150 mg/ml, polysorbate 80 at a concentration from about 0.01% w/v to 0.5% w/v by weight of the total formulation, and histidine at a concentration from about 5 mM and about 50 mM, wherein said composition has a pH of about 5 to about 5.5, and wherein said composition is substantially free of any other buffers.
T. A stable aqueous pharmaceutical composition comprising adalimumab at a concentration from about 20 and about 150 mg/ml, polysorbate 80 at a concentration from about 0.01% w/v to 0.5% w/v by weight of the total formulation, and tartrate at a concentration from about 5 mM and about 50 mM, wherein said composition has a pH of about 5 to about 5.5, and wherein said composition is substantially free of any other buffers.
U. A method of treating a mammal comprising administering to said mammal a therapeutically effective amount of the composition of any of preceding embodiments, wherein said mammal has a disease or disorder that can be beneficially treated with adalimumab.
V. The method of embodiment U, wherein said disease or disorder is selected from the group consisting of rheumatoid arthritis, psoriatic arthritis, ankylosing spondylitis, Wegener's disease (granulomatosis), Crohn's disease (or inflammatory bowel disease), chronic obstructive pulmonary disease (COPD), Hepatitis C, endometriosis, asthma, cachexia, psoriasis, and atopic dermatitis.

What is claimed is:

1. A stable aqueous pharmaceutical composition comprising:
   i) adalimumab;
   ii) a buffer; and
   iii) a stabilizer;
   wherein the composition is free of mannitol and has a pH of about 5 to about 6.

2. The composition of claim 1, wherein the composition is free of citrate buffer.

3. The composition of claim 1, wherein the composition further comprises a surfactant.

4. The composition of claim 1, wherein the composition has osmolality of about 180 to 420 mOsM; the composition is suitable for administration to a subject as a single dose; and the dose contains about 40 mg of adalimumab.

5. The composition of claim 1, wherein the composition is free of sodium chloride.

6. The composition of claim 5, wherein the composition further comprises a surfactant.

7. The composition of claim 6, wherein the composition has osmolality of about 180 to 420 mOsM; the composition is suitable for administration to a subject as a single dose; and the dose contains about 40 mg of adalimumab.

8. A stable aqueous pharmaceutical composition comprising adalimumab and a citrate-free buffer, wherein the composition is free of mannitol and has a pH of about 5 to about 6.

9. The composition of claim 8, wherein the composition further comprises a surfactant.

10. The composition of claim 8, wherein the composition has osmolality of about 180 to 420 mOsM; the composition is suitable for administration to a subject as a single dose; and the dose contains about 40 mg of adalimumab.

11. The composition of claim 8, wherein the composition is free of sodium chloride.

12. The composition of claim 11, wherein the composition further comprises a surfactant.

13. The composition of claim 12, wherein the composition has osmolality of about 180 to 420 mOsM; the composition is suitable for administration to a subject as a single dose; and the dose contains about 40 mg of adalimumab.

* * * * *